US011518780B2

(12) United States Patent
Fang

(10) Patent No.: US 11,518,780 B2
(45) Date of Patent: Dec. 6, 2022

(54) SENSITIVE OLIGONUCLEOTIDE SYNTHESIS USING SULFUR-BASED FUNCTIONS AS PROTECTING GROUPS AND LINKERS

(71) Applicant: Shiyue Fang, Houghotn, MI (US)

(72) Inventor: Shiyue Fang, Houghotn, MI (US)

( * ) Notice: Subject to any disclaimer, the term of this patent is extended or adjusted under 35 U.S.C. 154(b) by 164 days.

(21) Appl. No.: 16/946,455

(22) Filed: Jun. 23, 2020

(65) Prior Publication Data

US 2021/0032281 A1    Feb. 4, 2021

Related U.S. Application Data

(60) Provisional application No. 62/880,843, filed on Jul. 31, 2019.

(51) Int. Cl.
 *C07H 19/20*  (2006.01)
 *C07H 21/00*  (2006.01)
 *C07H 19/10*  (2006.01)

(52) U.S. Cl.
 CPC .............. *C07H 19/20* (2013.01); *C07H 19/10* (2013.01); *C07H 21/00* (2013.01)

(58) Field of Classification Search
 None
 See application file for complete search history.

(56) References Cited

U.S. PATENT DOCUMENTS

| | | |
|---|---|---|
| 6,277,982 B1 | 8/2001 | Fraser |
| 6,921,812 B1 | 7/2005 | Prakash |
| 2004/0009938 A1 | 1/2004 | Manoharan |
| 2009/0203132 A1* | 8/2009 | Swayze ................ C07D 207/12 435/375 |

FOREIGN PATENT DOCUMENTS

| | | |
|---|---|---|
| WO | WO2003004603 A2 | 1/2003 |
| WO | WO2007064291 A1 | 6/2007 |

OTHER PUBLICATIONS

Lin, X. (2013). Oligodeoxynucleotide synthesis using protecting groups and a linker cleavable under non-nucleophilic conditions (Doctoral dissertation, Michigan Technological University). (Year: 2013).*
Cieslak, et al. Thermolytic 4-Methylthio-1-butyl Group for Phosphate/Thiophosphate Protection . . . Journal of Organic Chemistry (2004), 69(7), 2509-2515. USA.
Jin, et al. Synthesis of Amine-and Thiol-Modified Nucleoside Phosphoramidites for Site-Specific . . . Journal of Organic Chemistry (2005), 70(11), 4284-4299. USA.
Sun, et al. Sulfonyl-Containing Nucleoside Phosphotriesters and Phosphoramidates as Novel . . . Molecular Pharmaceutics (2006), 3(2), 161-173. USA.
Zhou, et al. High-quality oligo-RNA synthesis using the new 2'-O-TEM protecting group . . . Canadian Journal of Chemistry (2007), 85(4), 293-301. Canada.
Zhou, et al. 2-(4-Tolylsulfonyl)ethoxymethyl (TEM)-a new 2'-OH protecting . . . Organic & Biomolecular Chemistry (2007), 5(2), 333-343. UK.
Ausin, et al. Assessment of heat-sensitive thiophosphate protecting groups in the development . . . Tetrahedron (2010), 66(1), 68-79. USA.
Shiyue Fang, et al. Synthesis of Oligodeoxynucleotides Containing Electrophilic Groups. Organic Letters, 2016, 18, 3870-3873. American Chemical Society. USA.
Shiyue Fang, et al. Incorporation of Sensitive Ester and Chloropurine Groups into Oligodeoxynucleotides through Solid Phase Synthesis. ChemistrySelect 2018, 3, 8857-8862. Euro.
Shiyue Fang, et al. Electrophilic Oligodeoxynucleotide Synthesis using dM-Dmoc for Amino Protection. Beilstein Journal of Organic Chemistry 2019, 15, 1116-1128. Germany.
Shiyue Fang, et al. Sensitive Oligodeoxynucleotide Synthesis Using Dim and Dmoc as Protecting Groups. Journal of Organic Chemistry 2019, 84, 13374-13383. USA.
Douglas, et al. An approach towards thiol mediated labeling in the minor groove of oligonucleotides. Bioorganic & Medicinal Chemistry Letters (1994), 4(8), 995-1000. USA.
Wagner, et al. Nucleotides. Part 50. Aglycon protection by the (2-dansylethoxy) carbonyl . . . Helvetica Chimica Acta (1997), 80(1), 200-212. Switzerland.
Fraser, et al. An efficient method for the synthesis of 2'-O-modified nucleosides via double alkylation using . . . Tetrahedron Letters (2000), 41(10), 1523-1526. USA.
Abramova, et al. Synthesis and properties of photolabile (caged) phosphotriester derivatives . . . Russian Journal of Bioorganic Chemistry (2000), 26(3), 174-182. Springer.
Prakash, et al. 2'-O-[2-(Methylthio)ethyl]-Modified Oligonucleotide: An Analogue of . . . Biochemistry (2002), 41(39), 11642-11648. USA.

(Continued)

*Primary Examiner* — Dale R Miller

(57) ABSTRACT

Embodiments for the synthesis of sensitive oligonucleotides as well as insensitive oligonucleotides are provided. Sulfur-based groups are used for the protection of exo-amino groups of nucleobases, phosphate groups and 2'—OH groups, and as cleavable linker for linking oligonucleotides to a support. Oligonucleotide syntheses are achieved under typical conditions using phosphoramidite chemistry with important modifications. To prevent replacing sulfur-based protecting groups by acyl groups via cap-exchange, special capping agents are used. To retain hydrophobic tag to assist RP HPLC purification, special phosphoramidites are used in the last synthetic cycle. With the sulfur-based groups for protection and linking, oligonucleotide deprotection and cleavage are achieved via oxidation followed by beta-elimination under mild conditions. Therefore, besides for insensitive oligonucleotide synthesis, the embodiments of the invention are capable for the synthesis of oligonucleotide analogs containing sensitive functional groups that cannot survive the harsh conditions used in prior art oligonucleotide synthesis technologies.

15 Claims, 30 Drawing Sheets

(56) References Cited

OTHER PUBLICATIONS

Ferreira, et al. Lewis acid deprotection of silyl-protected oligonucleotides and base-sensitive oligonucleotide analogs. Tetrahedron Letters (2004), 45(33), 6287-6290. USA.

* cited by examiner

Examples of non-canonical natural nucleosides that contain sensitive groups

Deprotection and cleavage of the sulfur-based protecting groups and linkers

Preparation of a solid support that contains a Dmoc linker

Synthesis of dM-Dmoc-CE-phosphoramidites

Synthesis of Dmoc-Dim-phosphoramidites

EtDmoc-EtDim-, PrDmoc-PrDim-, BuDmoc-BuDim-, PnDmoc-PnDim-phosphoramidites

Synthesis of example phosphoramidites with sensitive groups that can be incorporated into the middle of oligonucleotides Synthesis of example phosphoramidites with sensitive groups that can be incorporated onto the 5'-end of oligonucleotides

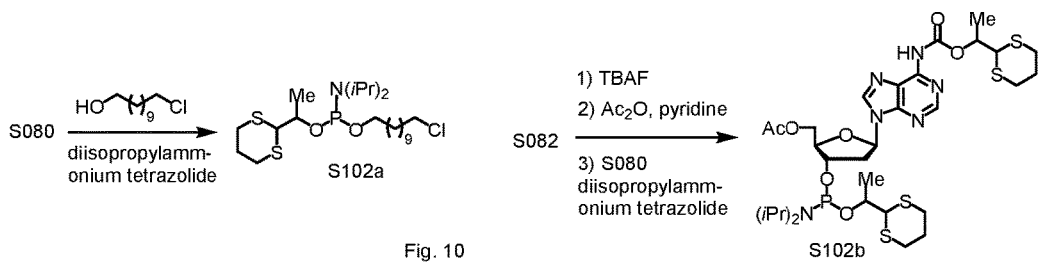

Fig. 10

Preparation of an example support that contains a Dmoc linker and can be used to introduce a sensitive group onto the 3'-end of oligonucleotides

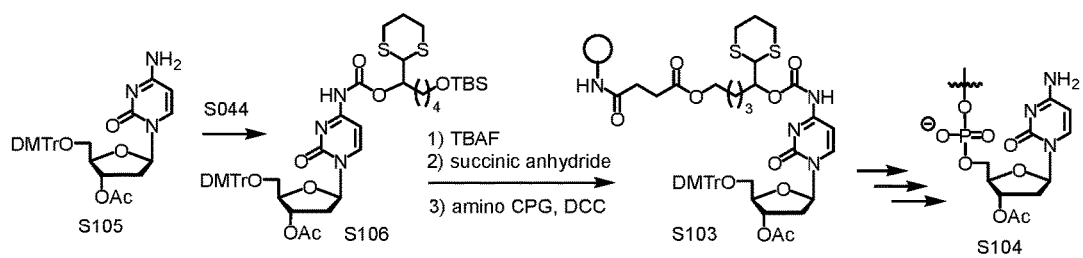

Fig. 11

MeDmoc-MeDim-phosphoramidites and Dmoc linker for oligonucleotide synthesis in the 5' to 3' direction

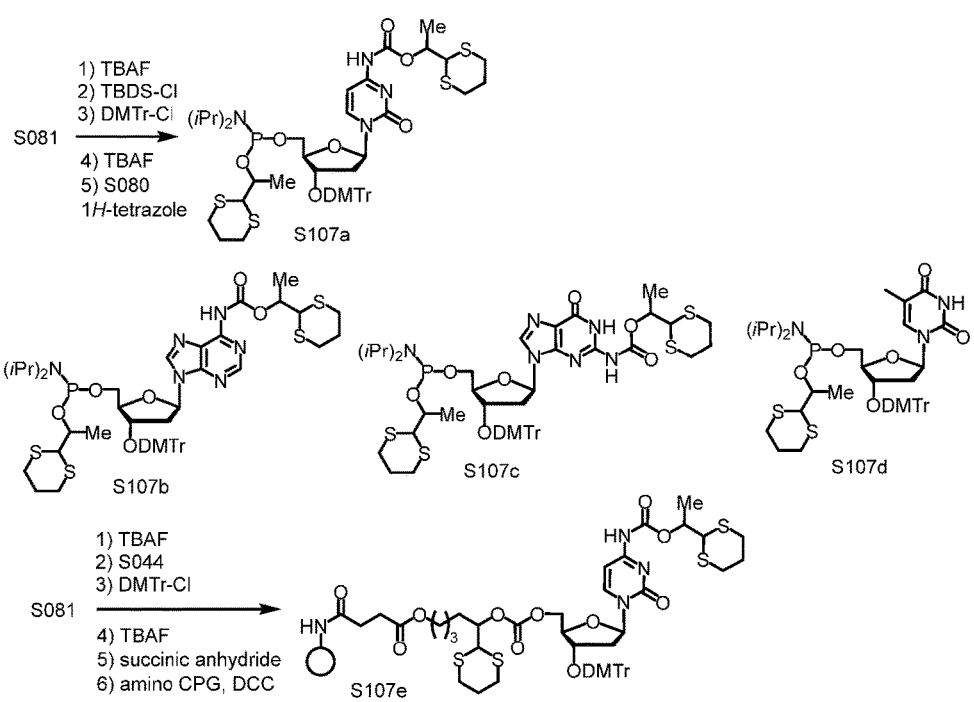

Fig. 12

MeDmoc-MeDim-phosphoramidites and Dmoc linker for RNA synthesis

MeDmoc-MeDim-phosphoramidites and Dmoc linker with 2'-TOM or 2'-TBDS protection for RNA synthesis MeDmoc-MeDim-phosphoramidites and Dmoc linker for LNA synthesis MeDmoc-MeDim-phosphoramidites and Dmoc linker for 2'-OCH₃ oligonucleotide synthesis

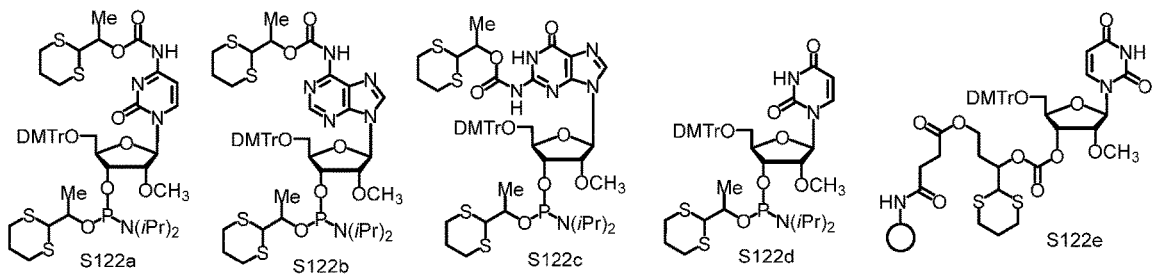

Fig. 17

MeDmoc-MeDim-phosphoramidites and Dmoc linker for 2'-F oligonucleotide synthesis

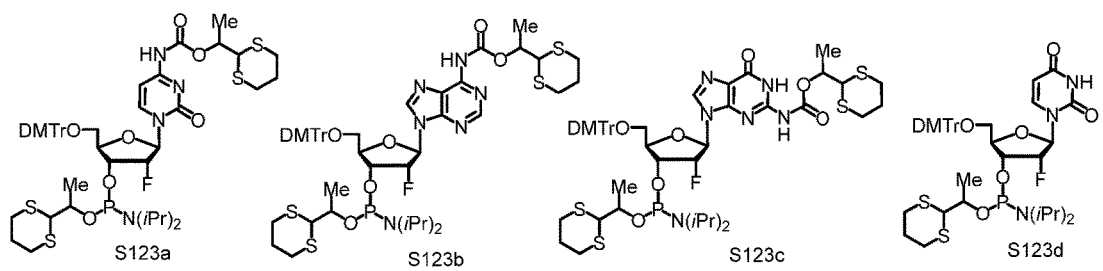

Fig. 18

Tagging agents for introducing a hydrophobic tag to the 5'-end of oligonucleotides to assist RP HPLC purification

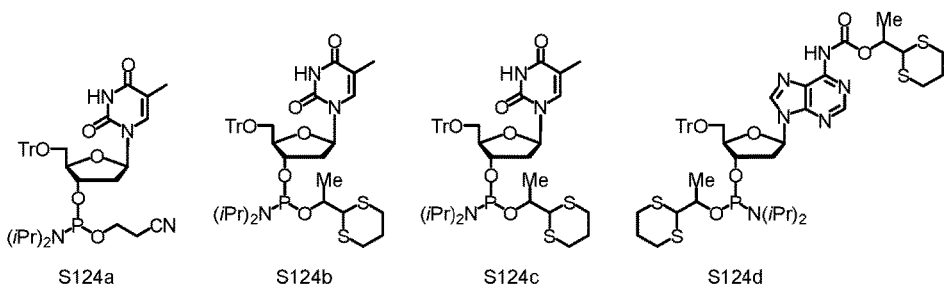

Fig. 19

Capping agents that can overcome the problem of cap-exchange in sensitive oligonucleotide synthesis

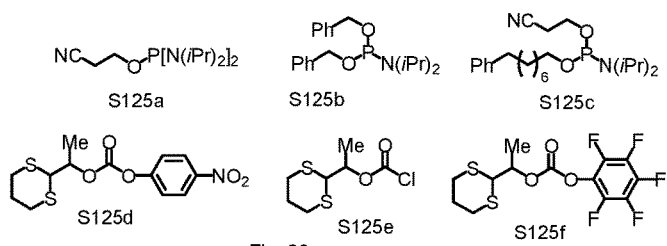

Fig. 20

Deprotection and cleavage of oligonucleotides assembled with Dmoc-CE-phosphoramidites Deprotection and cleavage of oligonucleotides assembled with dM-Dmoc-CE-phosphoramidites Deprotection and cleavage of oligonucleotides assembled with Dmoc-Dim-phosphoramidites

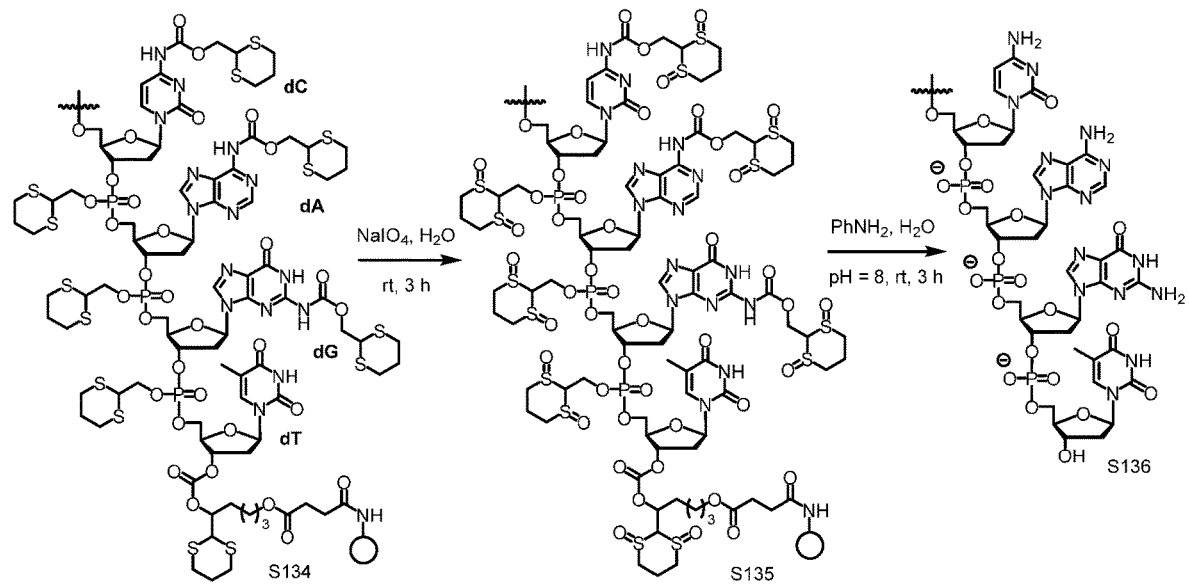

Fig. 23

Deprotection and cleavage of oligonucleotides assembled with AlkylDmoc-AlkylDim- and Dmoc-Dim phosphoramidites

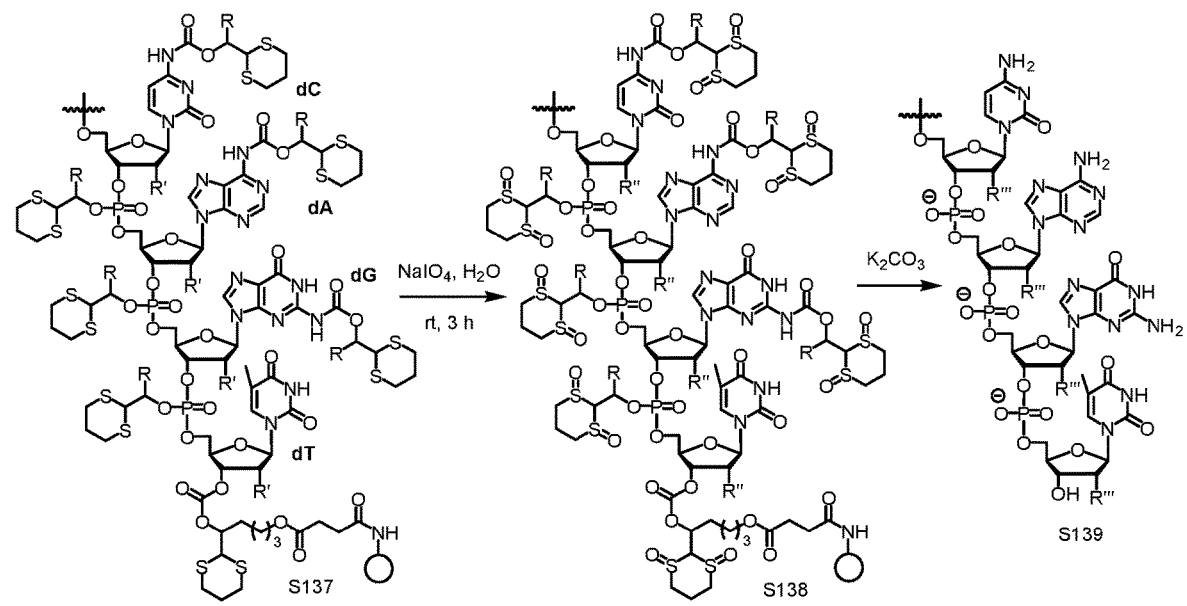

R = H, Me, Et or other groups; R' = H, F, OCH₃, OCH₂O-Dim, O-Dim or other groups; R'' = H, F, OCH₃, oxidized OCH₂O-Dim, oxidized O-Dim or other groups; R''' = H, F, OCH₃, OH or other groups

Fig. 24

Example oligonucleotide sequences including those containing sensitive groups that have been synthesized Fig. 26. RP HPLC profile of crude oligonucleotide S140a
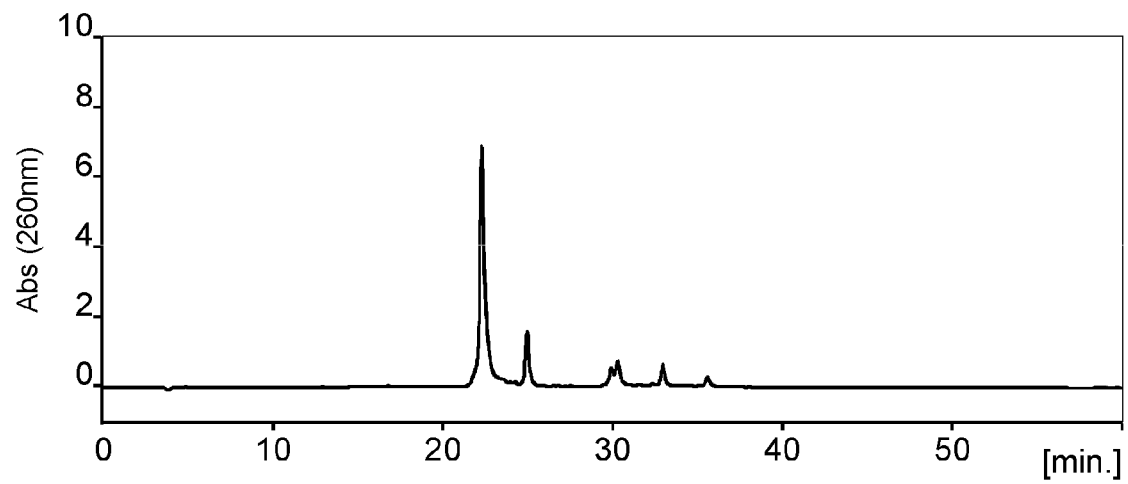
Fig. 27. RP HPLC profile of pure oligonucleotide S140a
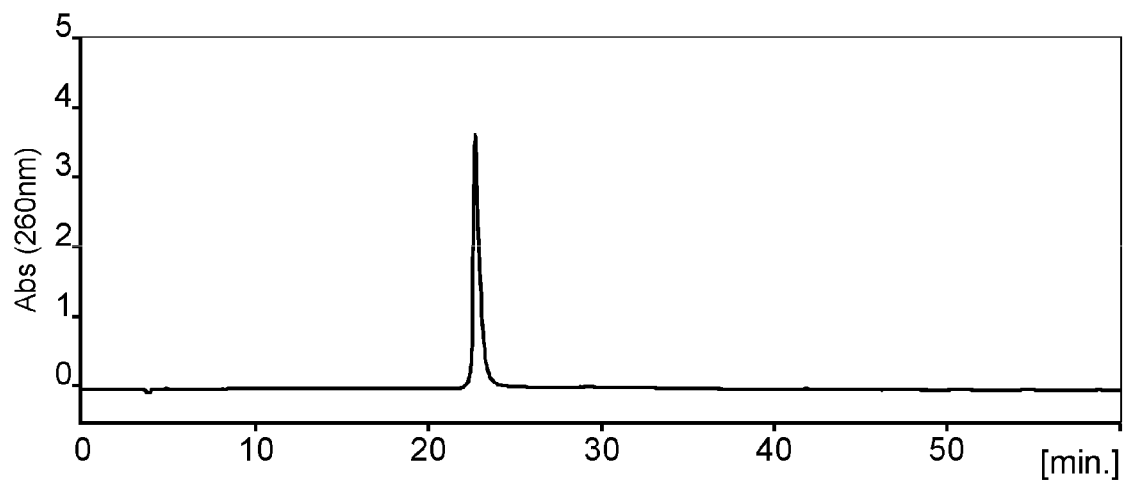

Fig. 28. MALDI-TOF MS of oligonucleotide 140a
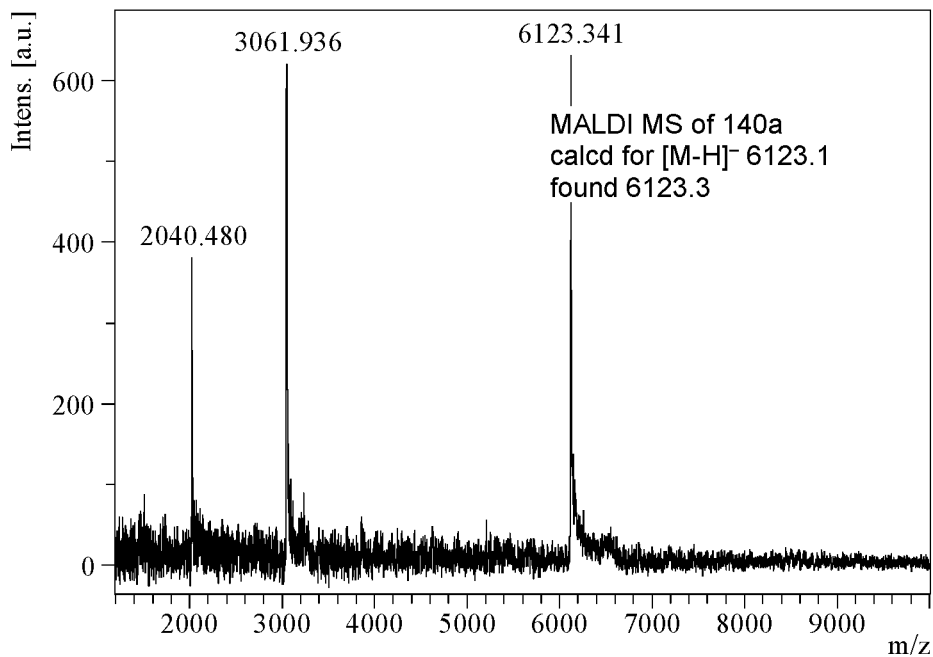
Fig. 29. RP HPLC profile of crude trityl-on oligonucleotide S140k
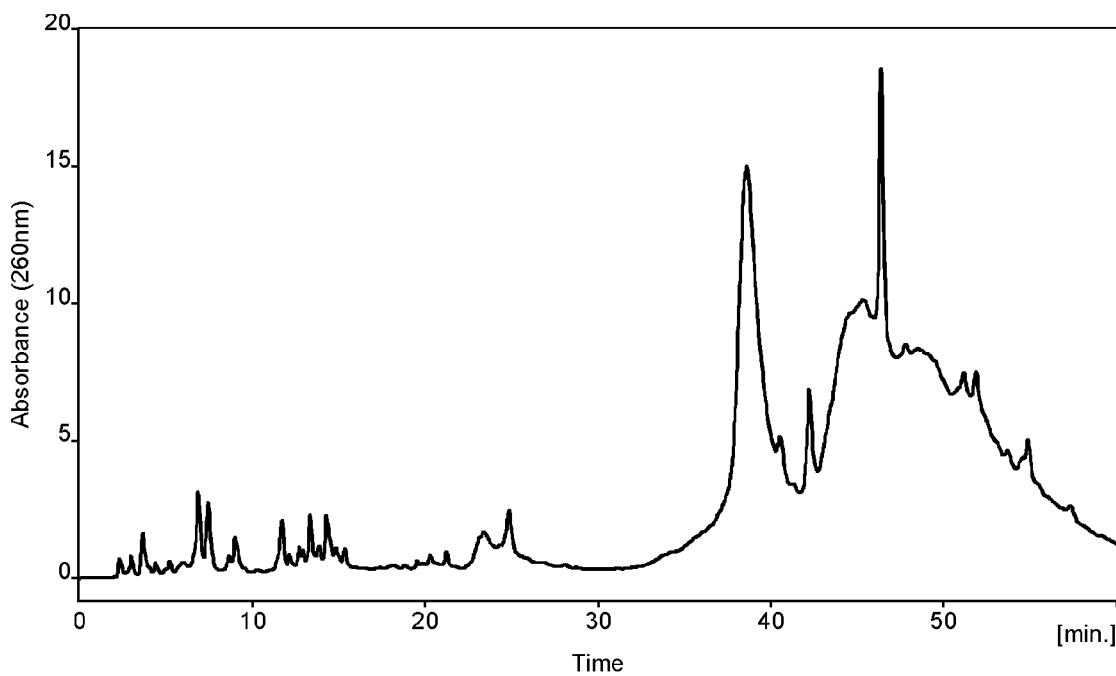

Fig. 30. RP HPLC profile of pure trityl-on oligonucleotide S140k
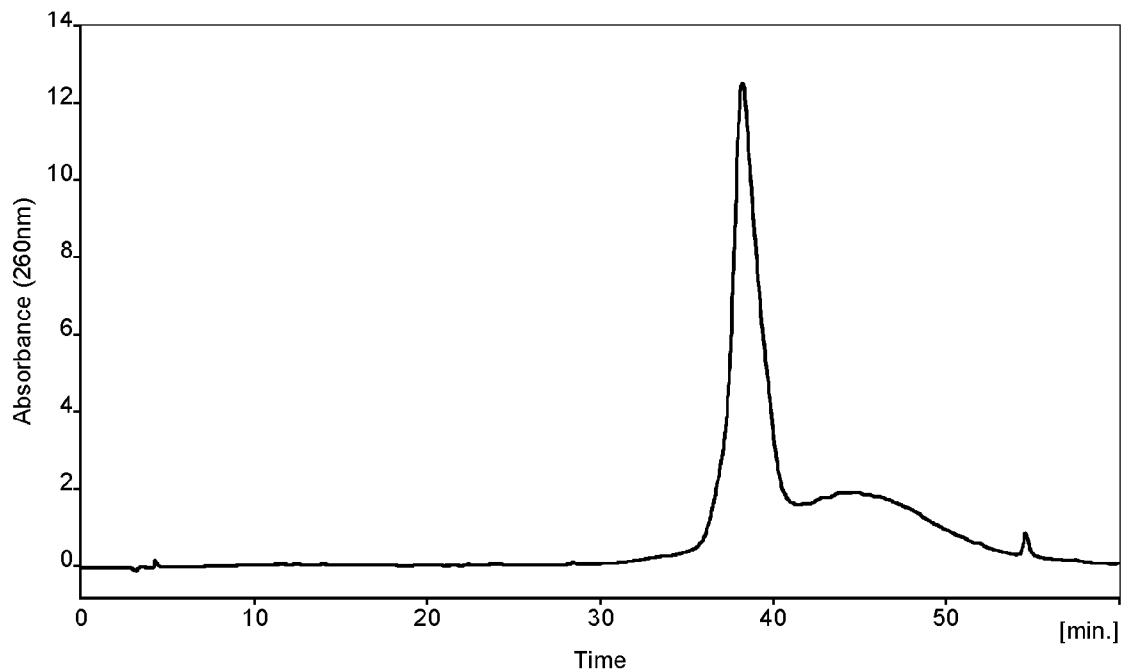
Fig. 31. RP HPLC profile of crude trityl-off oligonucleotide S140k
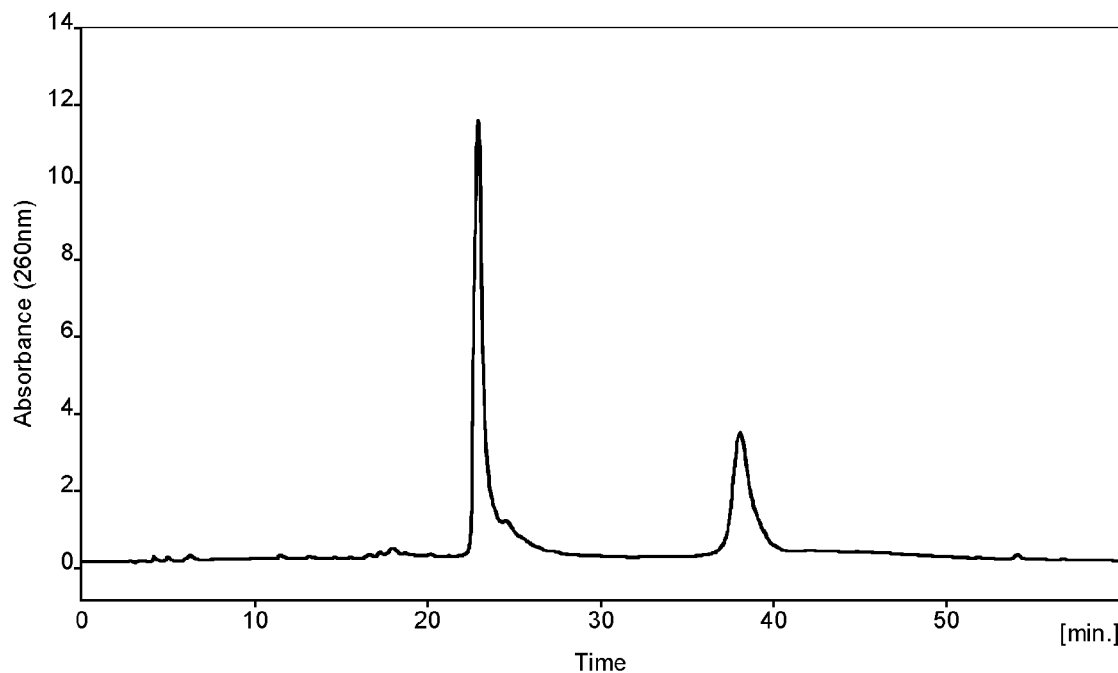

Fig. 32. RP HPLC profile of pure trityl-off oligonucleotide S140k
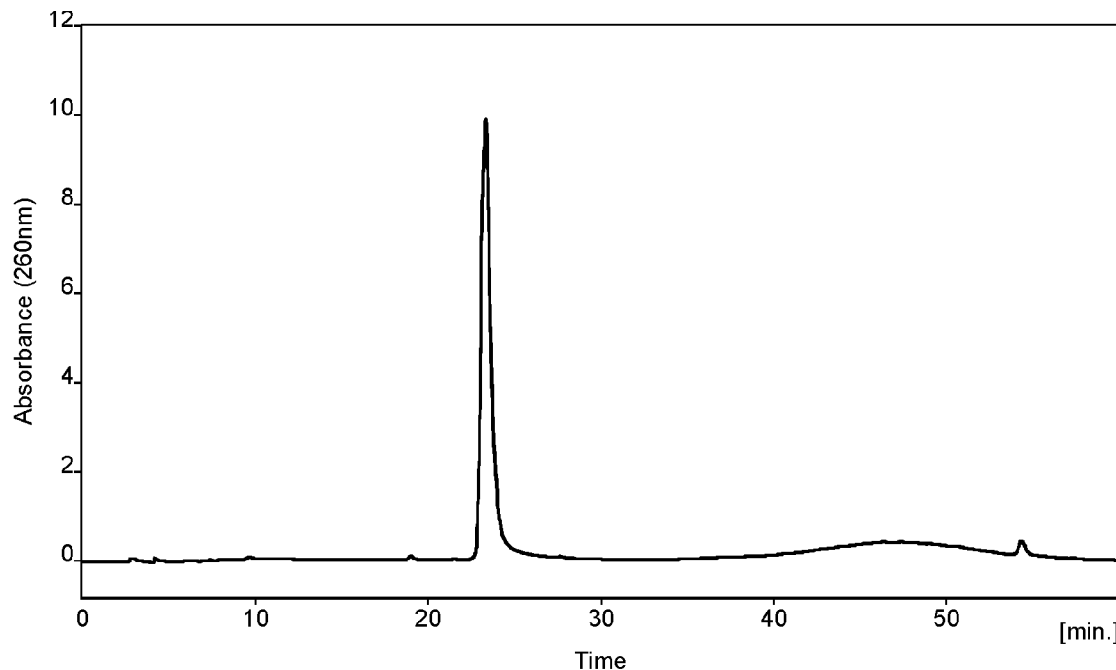
Fig. 33. MALDI-TOF MS of trityl-on oligonucleotide S140k
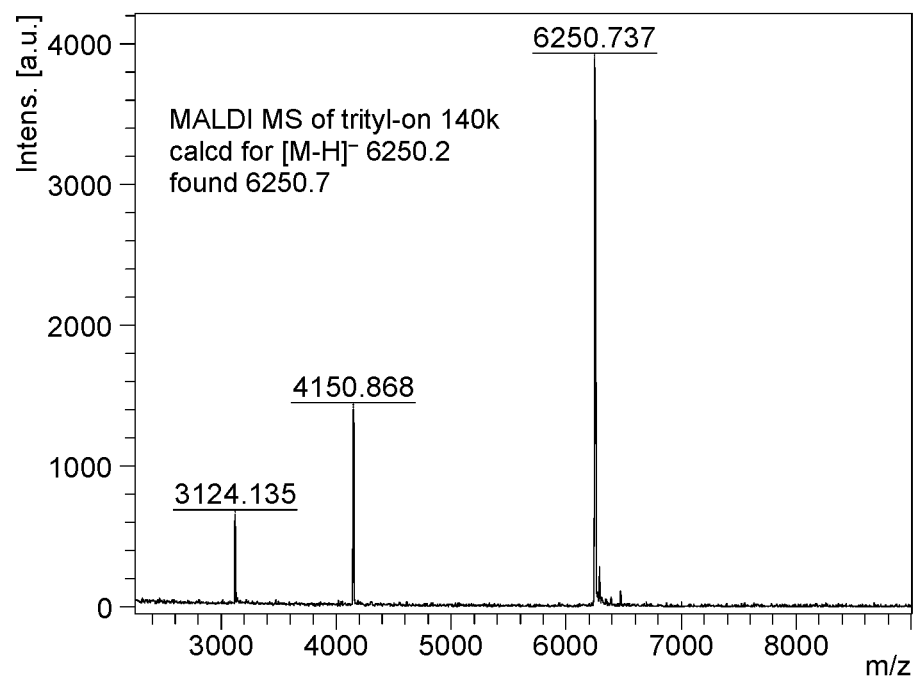

Fig. 34. MALDI-TOF MS of trityl-off oligonucleotide S140k
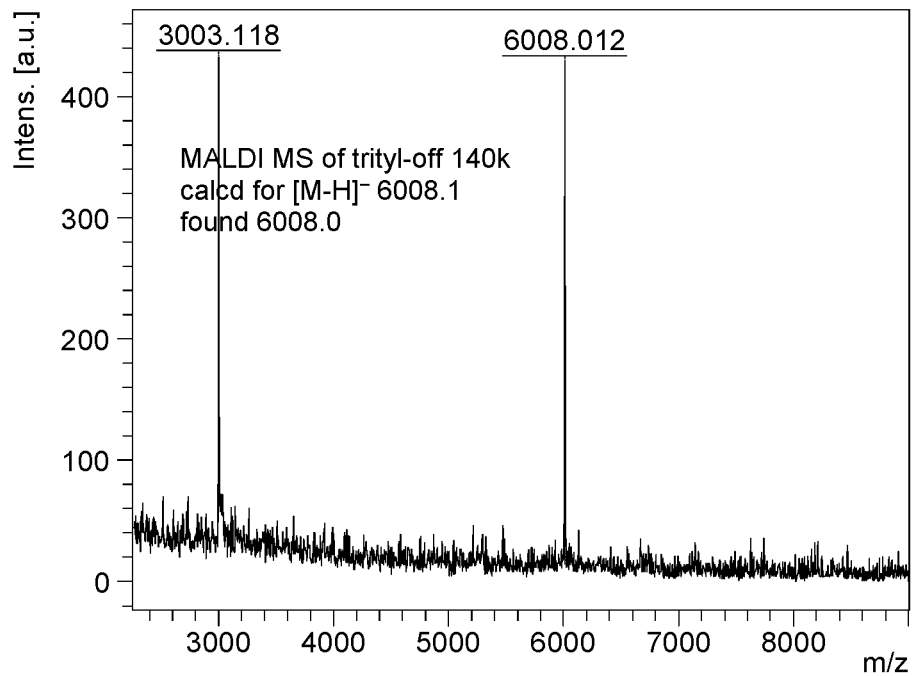
Fig. 35. RP HPLC profile of crude trityl-on oligonucleotide S140p
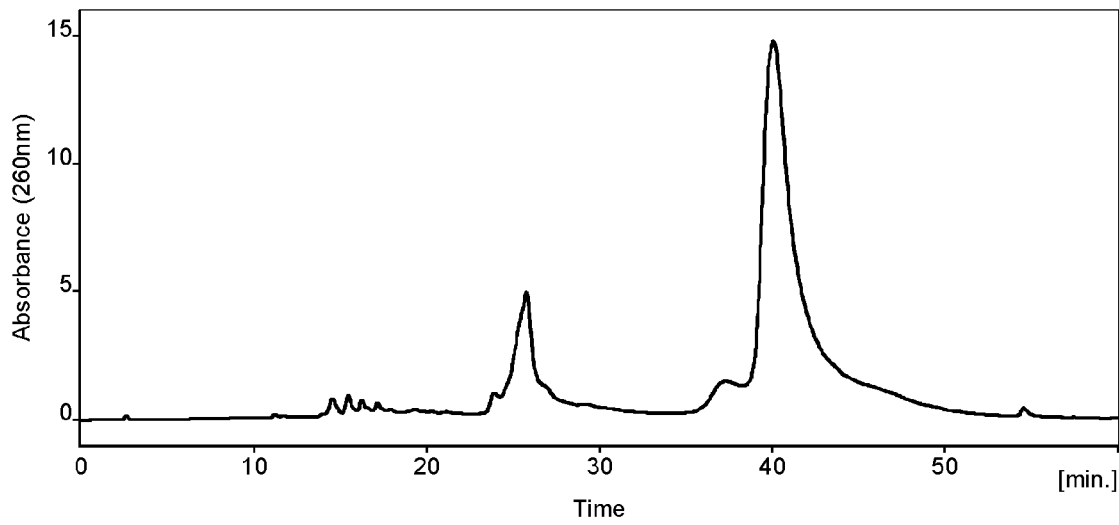

Fig. 36. RP HPLC profile of pure trityl-on oligonucleotide S140p
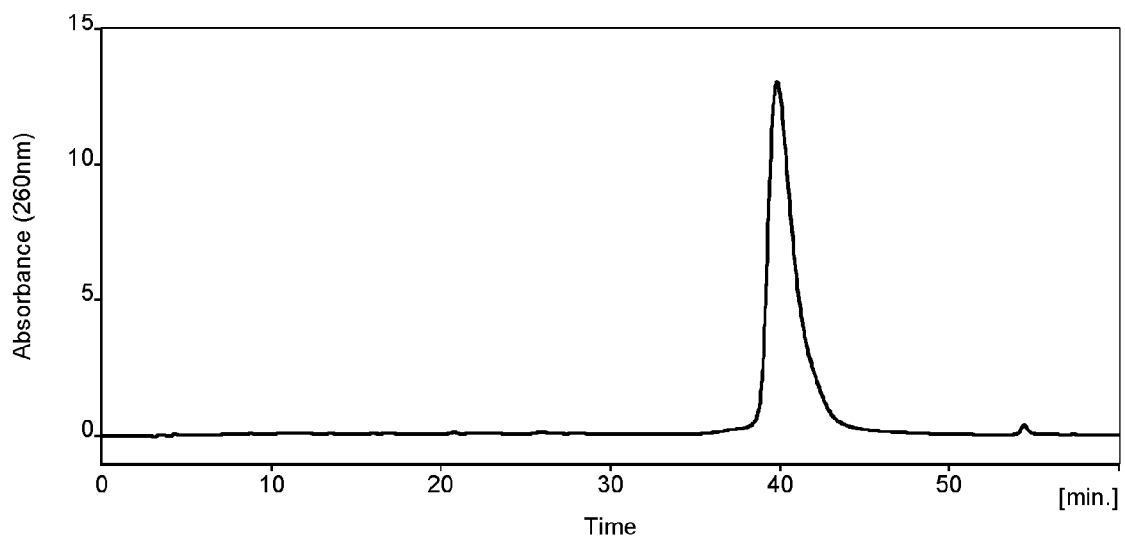
Fig. 37. RP HPLC profile of crude trityl-off oligonucleotide S140p
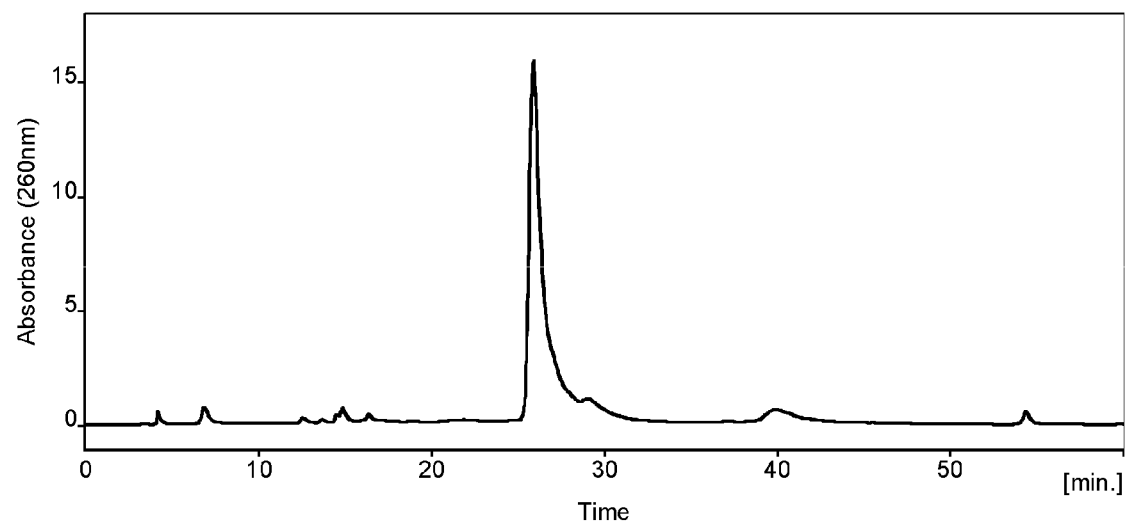

Fig. 38. RP HPLC profile of pure trityl-off oligonucleotide S140p
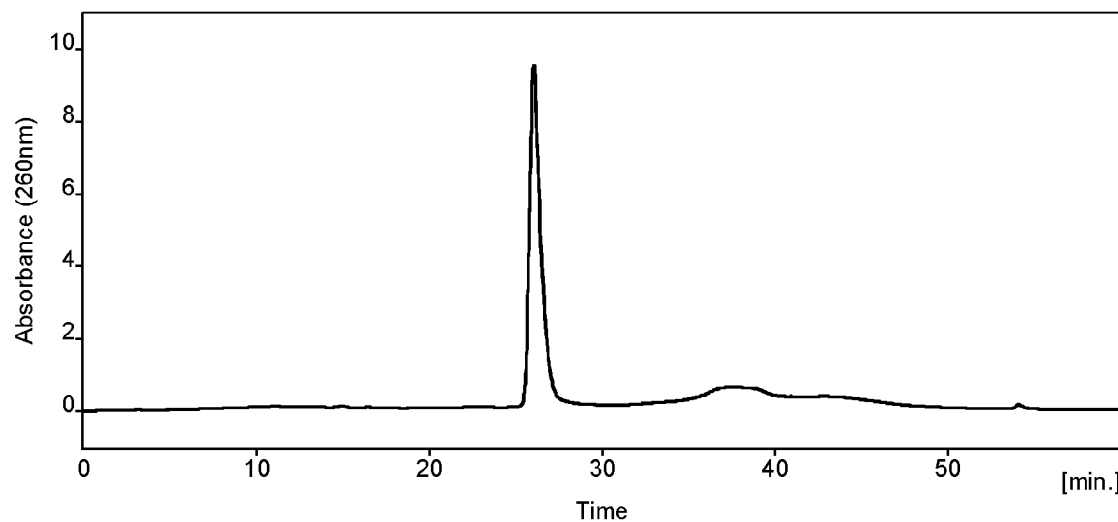
Fig. 39. MALDI-TOF MS of trityl-on oligonucleotide S140p
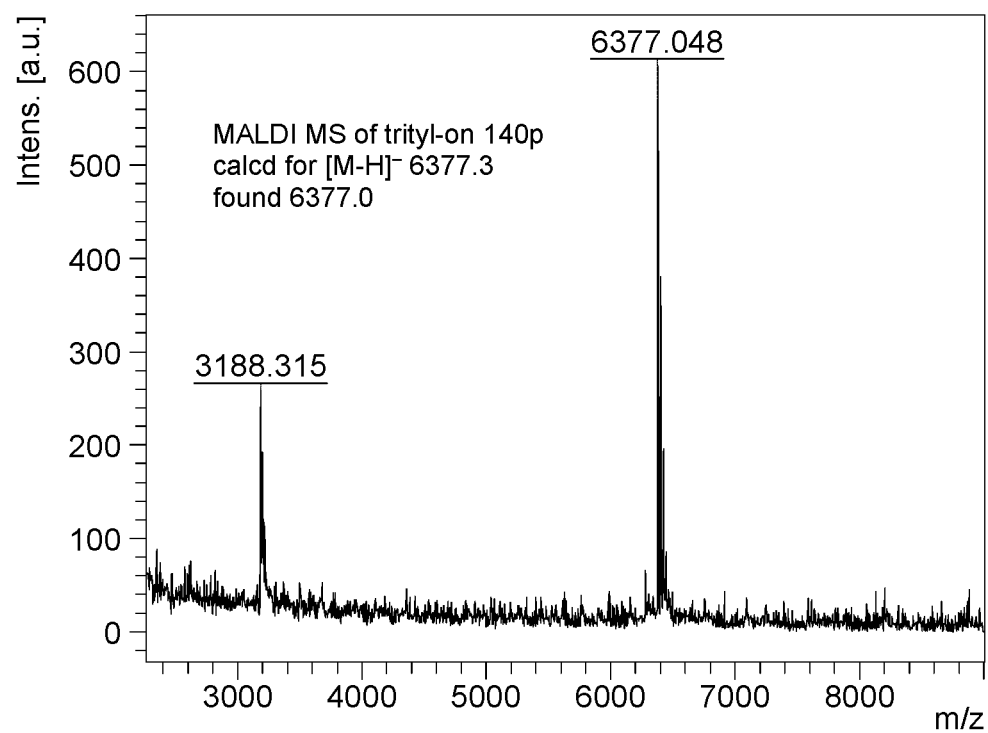

Fig. 40. MALDI-TOF MS of trityl-off oligonucleotide S140p
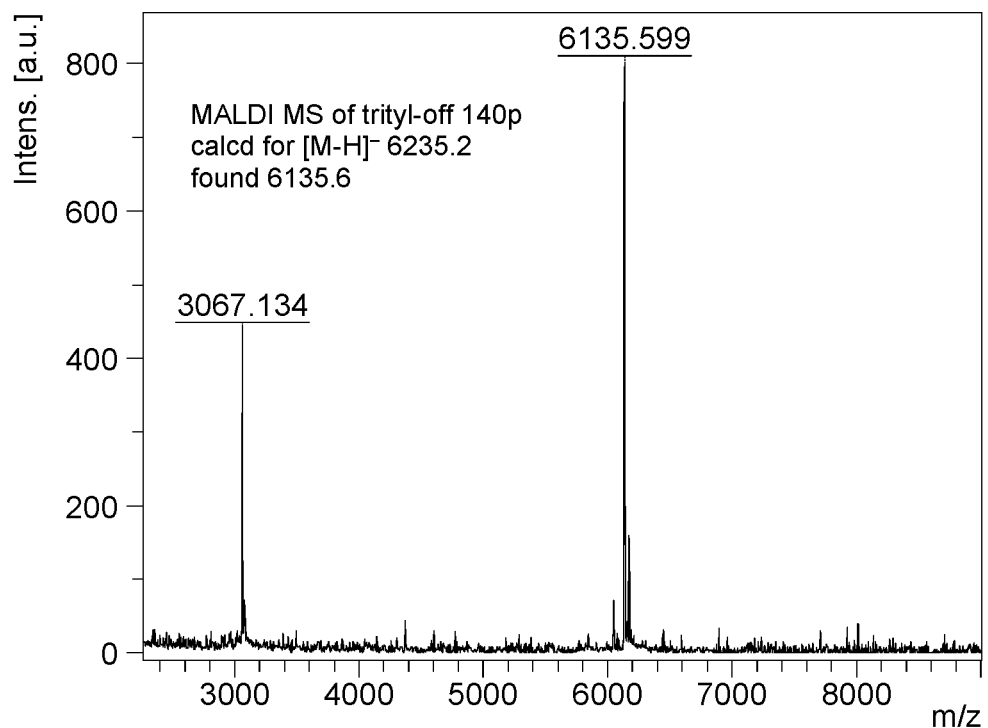
Fig. 41. RP HPLC profile of crude trityl-on oligonucleotide S140r
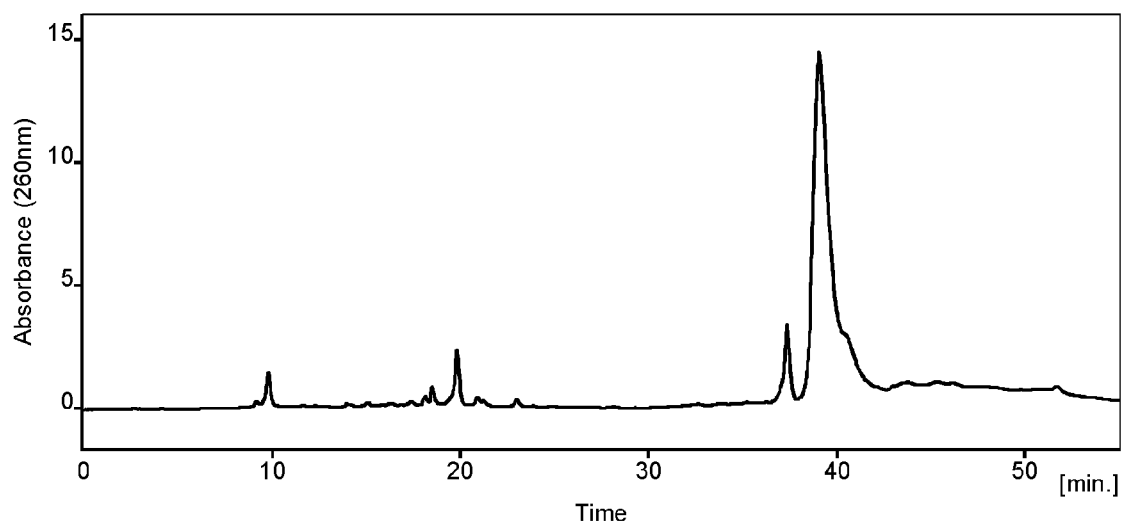

Fig. 42. MALDI-TOF MS of trityl-on oligonucleotide S140r
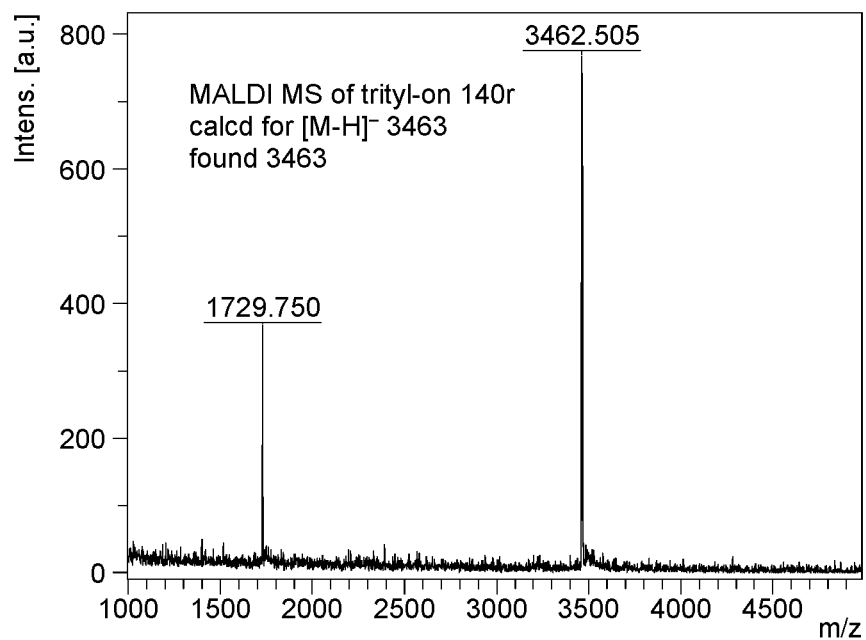
Fig. 43. RP HPLC profile of crude trityl-off oligonucleotide S140r
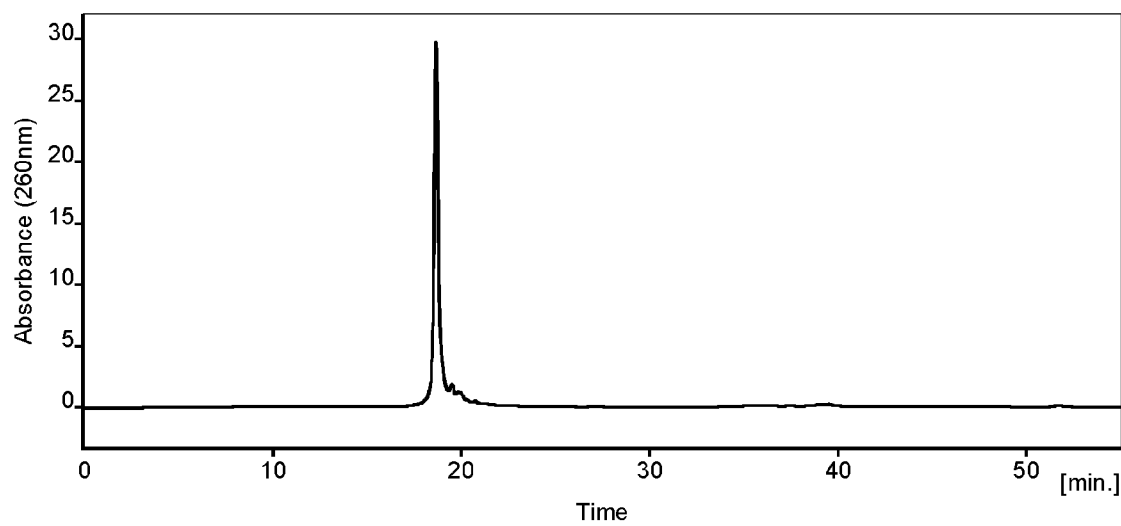

Fig. 44. MALDI-TOF MS of trityl-off oligonucleotide S140r
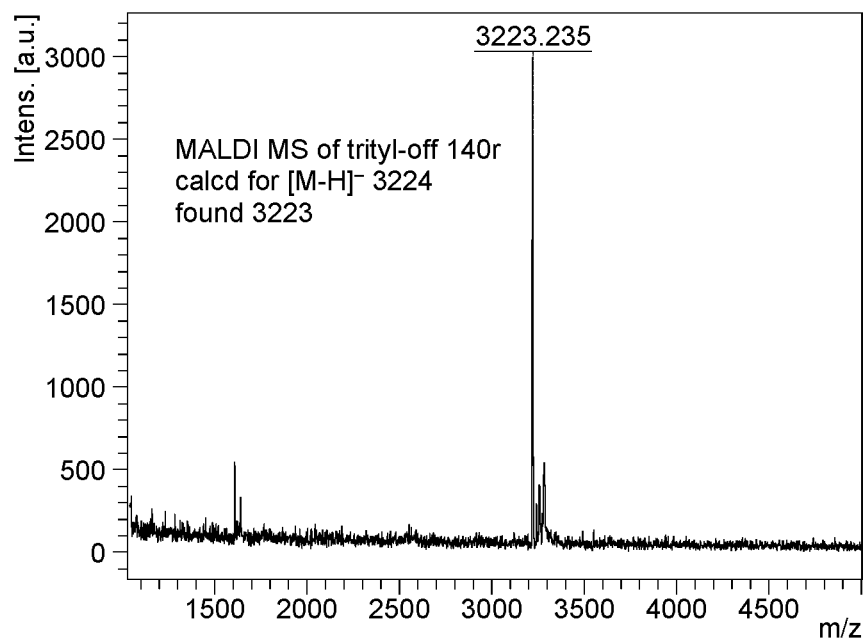
Fig. 45. RP HPLC profile of crude trityl-on oligonucleotide S140s
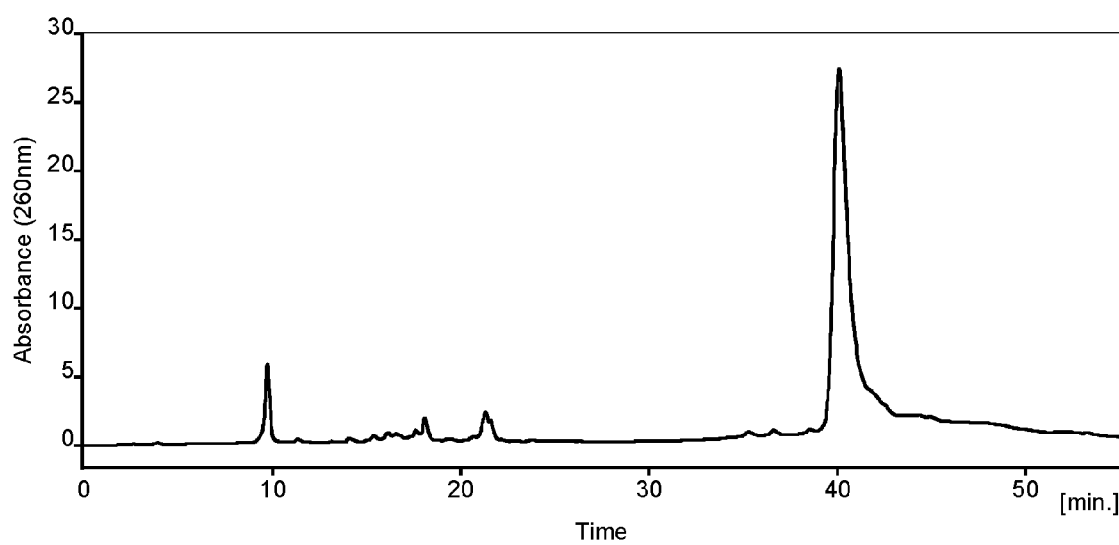

Fig. 46. MALDI-TOF MS of trityl-on oligonucleotide S140s
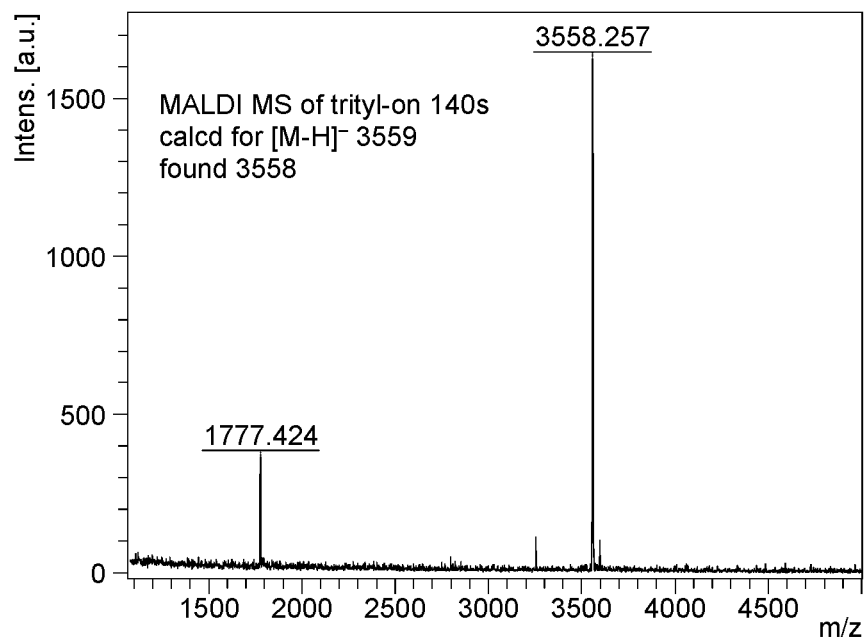
Fig. 47. RP HPLC profile of crude trityl-off oligonucleotide S140s
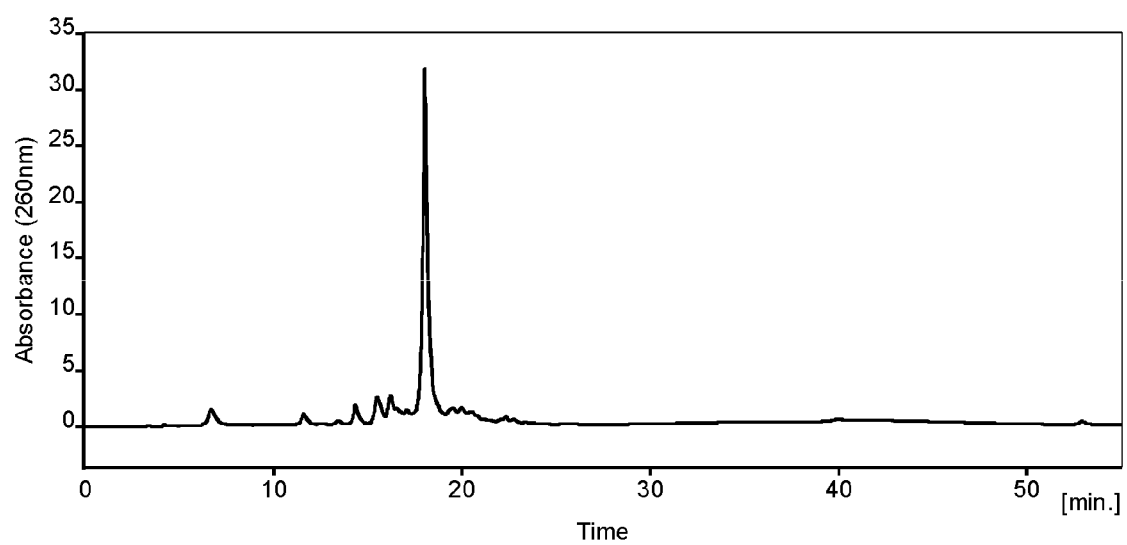

Fig. 48. MALDI-TOF MS of trityl-off oligonucleotide S140s
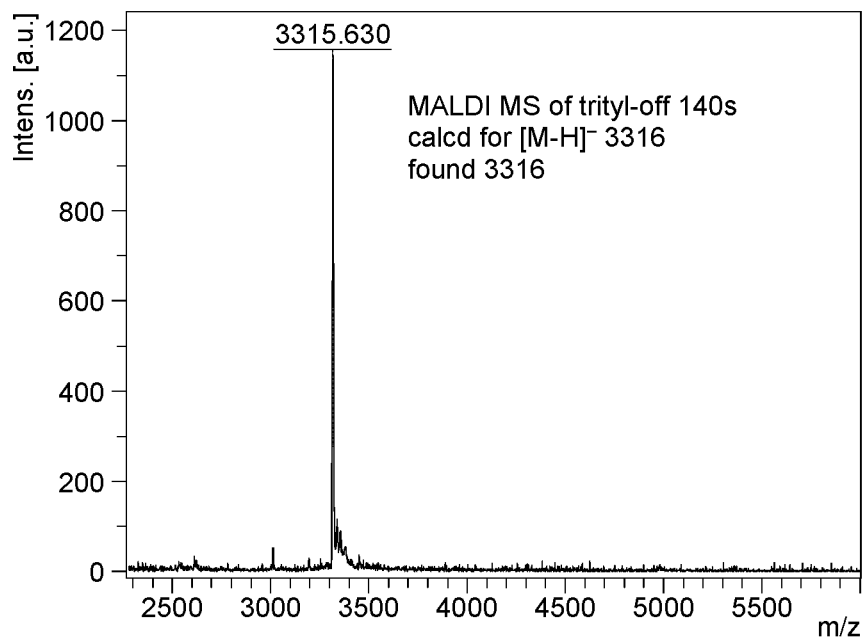
Fig. 49. RP HPLC profile of crude trityl-on oligonucleotide S140t
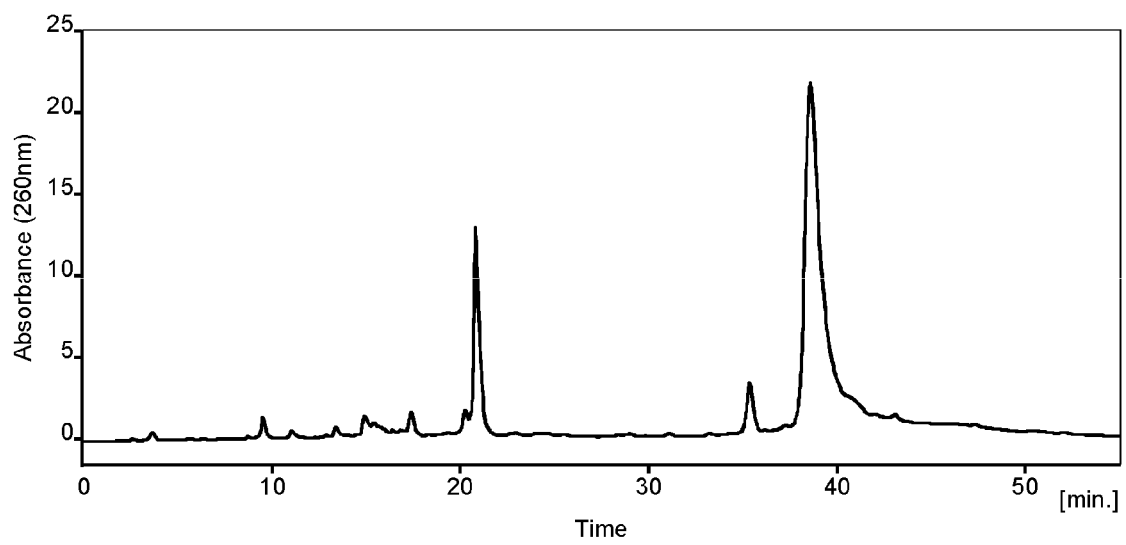

Fig. 50. MALDI-TOF MS of trityl-on oligonucleotide S140t
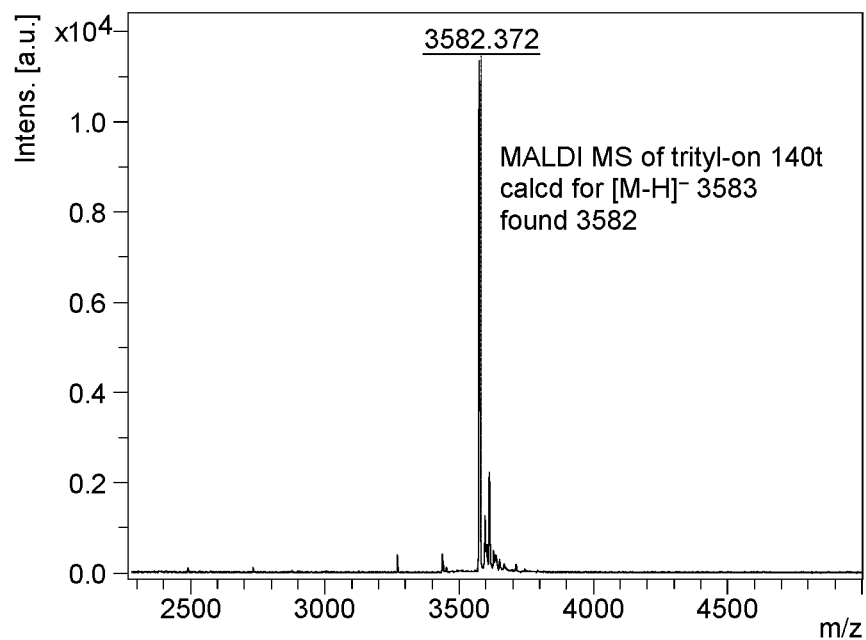
Fig. 51. RP HPLC profile of crude trityl-off oligonucleotide S140t
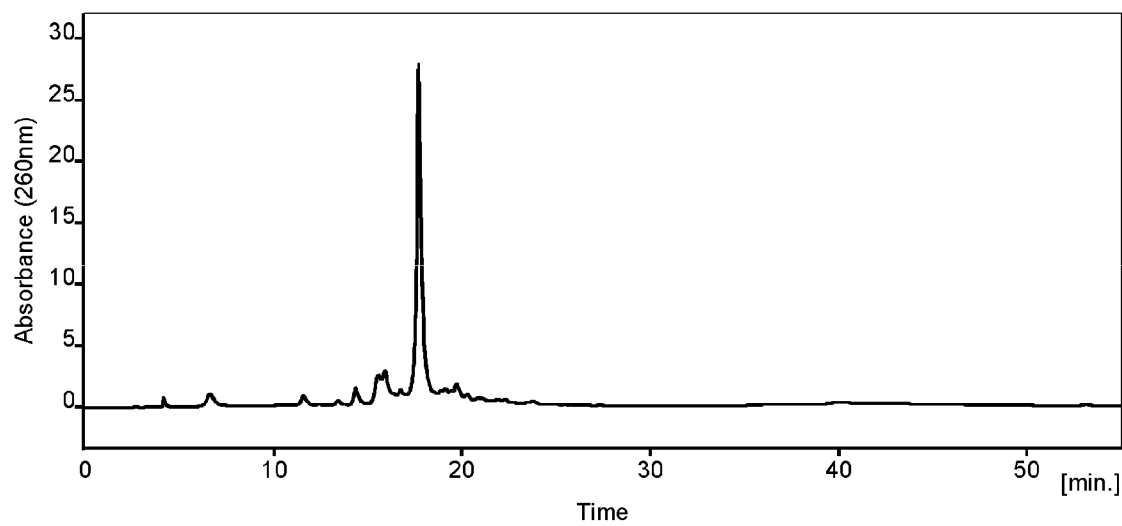

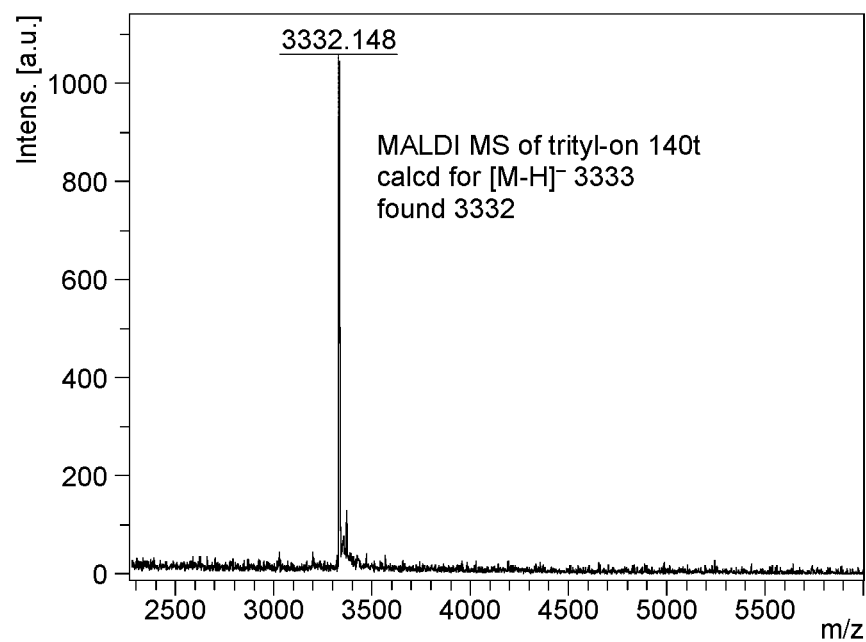
Fig. 52. MALDI-TOF MS of trityl-off oligonucleotide S140t

SENSITIVE OLIGONUCLEOTIDE SYNTHESIS USING SULFUR-BASED FUNCTIONS AS PROTECTING GROUPS AND LINKERS

CROSS-REFERENCE TO RELATED APPLICATIONS

This application for patent claims priority to Provisional application Ser. No. 62/880,843 filed on Jul. 31, 2019.

FEDERALLY SPONSORED RESEARCH

This invention was made with United States government support under grant No. GM109288 awarded by the National Institutes of Health. The government has certain rights in the invention.

BACKGROUND OF THE INVENTION

The present invention relates to the field of synthesis of oligonucleotides and their analogs. Oligonucleotides including DNA, RNA, their analogs and their conjugates with other molecules can co-exist with many functional groups. Example groups include esters, activated esters, arylamides, alkyl halides, benzyl halides, allyl halides, alkyl tosylates, α-halo amides, carbonates, thioesters, sulfonic esters, sultones, phosphate esters, α,β-unsaturated carbonyls, epoxides, aziridines, maleimides, vinyl arenes, methides, and many others. However, using existing oligonucleotide synthesis technologies, almost all these groups, which we call sensitive groups, cannot be incorporated into oligonucleotides. The reason is that existing oligonucleotide synthesis technologies use protecting groups based on the acyl function for amino protection, and the 2-cyanoethyl group or the methyl group for phosphate protection, and in the case of synthesis on a support, use acyl group-based cleavable linkers for linking oligonucleotide to the support. These protecting groups and linkers have to be cleaved under strongly nucleophilic and basic conditions such as concentrated ammonium hydroxide at elevated temperature for long period of time. Under these harsh conditions, the aforementioned sensitive groups cannot survive.

Oligonucleotides containing one or more sensitive groups, if they could be synthesized, would find numerous applications in many areas including molecular biology, biomedical research, medicine, and nanotechnology. For example, many noncanonical nucleosides have been found in oligonucleotides in the biological systems. Some of them contain one or more sensitive groups [T Carell et al 2012 *Angew Chem Int Ed* 51:7110 doi:10.1002/anie.201201193]. Chemical synthesis of these sensitive oligonucleotides is direly needed for many studies, which include investigation of the origin of the sensitive oligonucleotides, their functions, and their metabolic pathways in cellular processes. The data obtained from such studies are important for understanding the causes of diseases associated with sensitive oligonucleotides and for designing medicines. In addition, when oligonucleotides are used as medicines such as vaccine and protein expression guides [M A Liu 2019 *Vaccines* 7:37 doi:10.3390/vaccines7020037, C Zhang et al 2019 *Front Immunol* 10:594 doi:10.3389/fimmu.2019.00594, P S Kowalski et al 2019 *Mol Ther* 27:710 doi:10.1016/j.ymthe.2019.02.012, L Versteeg et al 2019 *Vaccines* doi:10.3390/vaccines7040122, M L Guevara et al 2019 *Curr Pharm Des* 25:1443 doi:10.2174/1381612825666190619150221, N Pardi et a/2017 *Methods Mol Biol* 1499:109 doi:10.1007/978-1-4939-6481-9_6], oligonucleotides with modifications including sensitive modifications in place by chemical synthesis are expected to have higher potency and lower toxicity [N Pardi et al 2017 *Methods Mol Biol* 1499:109 doi:10.1007/978-1-4939-6481-9_6, N Pardi et a/2018 *J Exp Med* 215:1571 doi:10.1084/jem.20171450, N Pardi et a/2015 *J Control Release* 217:345 doi:10.1016/j.jconrel.2015.08.007]. Several example non-canonical nucleosides are shown in FIG. 1. Unfortunately, even with a simple acetyl group on cytidine or a simple ester group on a thymidine analog, oligonucleotides containing these nucleosides cannot be synthesized with any existing technologies. In the area of antisense drug development, if a sensitive electrophilic group such as an ester group could be introduced to a location in an oligonucleotide that can enable it to react with a complementary oligonucleotide to form DNA inter-strand cross-link utilizing the proximity effect resulted from double helix formation, such electrophilic oligonucleotide could become the next generation antisense drugs. These new generation of antisense drugs could have much higher potency than existing drugs [C Rinaldi et al 2018 *Nat Rev* Neuro/14:9 doi:10.1038/nrneurol.2017.148]. In biological systems, oligonucleotides constantly interact with proteins. Such interactions are fundamental processes in molecular biology. However, many such interactions are highly dynamic, and there is no ideal method to study them. One method to overcome the challenge is to utilize oligonucleotides that contain a sensitive electrophilic group such as an alkyl halide. When the oligonucleotide interacts with a protein, due to a proximity effect, the alkyl halide could react with a nucleophilic group of the protein and form a covalent bond. The alkylated protein can then be partially digested and analyzed with mass spectrometry. From mass data, the interaction sites of the oligonucleotide and protein can be pinned down [C J Bley et al 2011 *Proc Natl Acad Sci USA* 108:20333 doi:10.1073/pnas.1100270108]. DNA is a nucleophilic molecule. It reacts with a wide range of electrophiles in the environment forming DNA alkylation products. Alkylation of DNA in human is one of the major causes of cancer. Currently, many of the DNA alkylation products cannot be synthesized using existing chemical technologies, while chemical synthesis of them is critical for studies in the area of DNA damage and repair [N V Volkova et al 2020 *Nat Commun* 11:2169 doi:10.1038/s41467-020-15912-7, C M N Aloisi et al 2020 *J Am Chem Soc* 142:6962 doi:10.1021/jacs.9b11746, T D Lama-Sherpa et al 2020 *Mol Cancer Res* 18:185 doi:10.1158/1541-7786.MCR-19-0665, M H Raz et al 2019 *Acc Chem Res* 52:1391 doi:10.1021/acs.accounts.9b00054, R Thapar et al 2019 *Biochem* 58:312 doi:10.1021/acs.biochem.8b00949]. The above is only a few of numerous potential applications of sensitive oligonucleotides. Overall, oligonucleotides are one of the most important classes of molecules in nature. Although chemists can synthesize the most common unmodified oligonucleotides with ease, it is unfortunate that many of their sensitive analogs cannot be synthesized. This invention is aimed to addressing this problem.

In the literature, some attempts have been made to address the challenge of the synthesis of sensitive oligonucleotides. The following summarizes the methods and their shortcomings. One method used the more labile acyl groups—the phenoxyacetyl based groups—for the protection of the exo-amino groups of nucleosides. Due to the electron-withdrawing property of the phenoxy group attached to the acetyl group, these groups can be deprotected under conditions (e.g. concentrated NH$_4$OH, room temperature, 2 hours; and dilute KOCH$_3$, CH$_3$OH, room temperature, 4 hours) milder than typical deprotection conditions (e.g. concentrated NH$_4$OH, 55° C., 8 hours). Therefore, technologies based on these groups can be used to incorporate some of the sensitive groups into oligonucleotides [J C Schulhof et al 1987 *Tetrahedron Lett* 28:51 doi:10.1016/50040-4039(00)95646-6]. However, the limitation of the method is obvious because ammonium hydroxide and potassium methoxide are both strong nucleophiles and bases. Many sensitive groups including the simplest esters and alkyl halides cannot survive the conditions.

The nitrobenzyl-based groups have been studied as cleavable linkers for oligonucleotide synthesis. With these linkers, oligonucleotides can be cleaved from solid support with UV irradiation [T J Matray et al 1994 *J Am Chem Soc* 116:6931 doi:10.1021/ja00094a056]. However, it is well-documented that UV light can damage oligonucleotides. Due to this problem, nitrobenzyl-based linkers have not found practical applications for sensitive oligonucleotide synthesis.

The allyl and benzyl groups have been studied for the protection of exo-amino groups of nucleosides. Using these protecting groups, oligonucleotide deprotection can be achieved with palladium instead of harsh nucleophilic and basic conditions [Y Hayakawa et al 1990 *J Am Chem Soc* 112:1691 doi:10.1021/ja00161a006]. However, palladium is a precious metal and highly expensive. It has to be used in excess for the deprotection to be complete. More seriously, it is highly challenging to remove palladium, which is toxic, from the oligonucleotide product. Due to these drawbacks, oligonucleotide synthesis methods based on allyl and benzyl groups have not found practical applications.

The (p-nitrophenyl)ethyl (Npe) and (p-nitrophenyl)ethyl-oxycarbonyl (Npeoc) groups were also explored for sensitive oligonucleotide synthesis. However, these groups have to be removed using the strong base DBU in aprotic solvents over long periods of time in the presence of nucleophilic scavengers. Under these conditions, many sensitive groups will not survive. In addition, with these protecting groups, only the synthesis of short oligonucleotides have been reported, and the yields of those syntheses were low [R Eritja et al 1992 *Tetrahedron* 48:4171 doi:10.1016/S0040-4020(01)92195-7].

The Fmoc and DNSEOC groups were also considered for oligonucleotide synthesis including sensitive oligonucleotide synthesis [S C Srivastava et al 2010 *PCT Application WO2010062404A2*], S C Srivastava et al 2015 U.S. Pat. No. 8,981,076], T Wagner et al 1997 *Helv Chim Acta* 80:200 doi:10.1002/hlca.19970800118]. These groups are highly base sensitive, and therefore can be removed under milder basic conditions using ammonium hydroxide or triethyl amine. However, due to their high sensitivity, the groups are easy to fall off prematurely during oligonucleotide synthesis. The premature deprotection can result in many side reactions and side oligonucleotide products.

Besides attempts to use protecting groups and linkers that can be cleaved under milder conditions for sensitive oligonucleotide synthesis, efforts have also been directed to the use of phosphoramidite monomers without protection of exo-amino groups for oligonucleotide synthesis [A Ohkubo et al 2004 *J Am Chem Soc* 126:10884 doi:10.1021/ja048125h]. This method suffers from the difficulty to achieve high selectivity of O-phosphitylation over N-phosphitylation, which is required for practical applications. In addition, there are also reports on the use of post-synthesis modifications to incorporate sensitive groups into pre-assembled oligonucleotides [M M Ali et al 2006 *Angew Chem Int Ed* 45:3136 doi:10.1002/anie.200504441] and using enzymatic reactions to incorporate sensitive groups into oligonucleotides [M Cowart et al 1991 *Biochem* 30:788 doi:10.1021/bi00217a032]. These methods are tedious, case-specific, and only workable in a few special cases, and therefore their applications are very limited in scope.

For phosphate protection in oligonucleotide synthesis, no attempts have been made to develop a protecting group that can be removed under neutral and non-nucleophilic conditions. The most commonly used 2-cyanoethyl group or methyl group has to be deprotected under strongly basic or nucleophilic conditions, which are not compatible with many sensitive groups.

The lack of a technology in the prior art for the synthesis of sensitive oligonucleotides is mainly due to the complexity of chemical oligonucleotide synthesis. The synthesis requires many steps under a variety of different reaction conditions. For example, for the synthesis of a 20-mer oligonucleotide, a total of 76 steps are needed and four different reaction conditions have to be applied to the nascent oligonucleotides repeatedly. During the synthesis, the exo-amino groups of nucleosides have to be protected, and in supported synthesis, the oligonucleotide has to be anchored to a support with a cleavable linker. Therefore, a functional group that can survive all the conditions used for the synthesis but can be cleaved with high efficiency must be identified for protecting and linking. In sensitive oligonucleotide synthesis, this is even more challenging because the functional group must be cleavable under exceptionally mild conditions. Unfortunately, functional groups that can be used for protection and linking in organic chemistry are limited, and identification of one that can satisfy all the requirements is difficult. In prior art, all common functional groups in organic chemistry that could potentially be useful for the purpose have been tested. However, the groups either lack the required stability during oligonucleotide synthesis (e.g. Fmoc group), or are difficult or require expensive and harmful reagents to cleave during cleavage and deprotection (e.g. phenoxyacetyl group, o-nitrobenzyl group, allyl group, benzyl group and Npe group). The lack of stability is partially due to the repeated exposure of the groups to different conditions during the synthesis. The difficulty for cleavage and deprotection is partially due to the fact that many functions have to be cleaved simultaneously under conditions without destroying the sensitive groups as well as the oligonucleotide itself.

BRIEF SUMMARY OF THE INVENTION

This invention is related to the use of sulfur-based groups for protection and linking in oligonucleotide synthesis. These groups and linkers are completely stable under all the oligonucleotide synthesis conditions, but at the end of synthesis, they can be completely cleaved with high efficiency under nearly neutral and nearly non-nucleophilic conditions. Under these mild deprotection and cleavage conditions, many sensitive groups including, but not limited to esters, activated esters, arylamides, alkyl halides, benzyl halides, allyl halides, alkyl tosylates, α-halo amides, carbonates, thioesters, sulfonic esters, sultones, phosphate esters, α,β-unsaturated carbonyls, epoxides, aziridines, maleimides, vinyl arenes and methides, can survive. Therefore, the new oligonucleotide synthesis technology is suitable for the synthesis of oligonucleotides and their analogs and conjugates that contain sensitive groups.

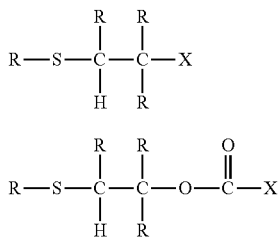

S001

S002

The sulfur-based protecting groups and linkers contain at least one sulfur atom, at least two carbon atoms, and at least one hydrogen atom as shown in structures S001 (abbreviation of "structure 001", all structures in this document are indicated by the letter S followed by a three-digit number or by a three-digit number with a lower-case letter such as S001a; for structures in the claims, a different numbering format is used) or S002. The two carbons are between the sulfur atom or atoms and the functional group that is to be protected or the molecule that is to be linked. The hydrogen atom is attached to one of the two carbon atoms that is attached to the sulfur atom or atoms. In S001 and S002, X is the functional group that is to be protected or the molecule that is to be linked to a support. The R groups are independent groups of atoms that will become clear in the following descriptions and claims.

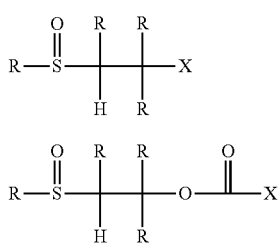

S003

S004

The protecting groups or linkers are highly stable because the hydrogen that is shown in S001 and S002 is not acidic in normal terms of organic chemistry. The non-acidic nature of the hydrogens is evident from their pKa values, which can be between 50 and 30 depending on the identity of R groups. However, when the sulfur atom or atoms are oxidized, and S001 and S002 become S003 (in S003 and later molecular formulas in this patent application, carbon atom is shown as an intersection of two or more bonds or the end of one bond following the custom in the field of organic chemistry) and S004, respectively, or their more oxidized forms, the hydrogens become significantly more acidic as implied by their pKa values, which can be between 35 and 12 or even lower depending on the identity of R groups.

Once the sulfur atom or atoms are oxidized and the hydrogen or hydrogens become far more acidic, beta-elimination occurs under nearly non-nucleophilic and non-basic conditions (e.g. 0.05 M $K_2CO_3$ at pH 8, room temperature, less than 3 hours). This releases the functional group that is being protected or the molecule that is being linked. FIG. 2 shows the process, wherein $X^-$ represents the deprotected functional group or the molecule released from a support. Examples of supports include, but are not limited to, insoluble supports, soluble polymer supports, and supports of soluble fluorinated carbon chains.

Due to the high stability of S001 and S002, and the exceptional lability of S003 and S004, when the former two are used for oligonucleotide synthesis, there will be no problem of premature deprotection, and after oxidation, deprotection and cleavage can be achieved under almost completely non-basic and non-nucleophilic conditions. Therefore, oligonucleotide synthesis technologies utilizing these groups for protection and linking are suitable for the synthesis of oligonucleotides that contain sensitive groups as well as natural unmodified oligonucleotides.

Advantages

Compared with the most commonly used oligonucleotide synthesis technologies, in which the exo-amino groups of nucleobases are protected with acyl groups, the phosphate groups are protected with the 2-cyanoethyl group, and in case of synthesis on a solid support, the oligonucleotide is anchored to the support with an ester-based cleavable linker, the embodiments of the invention do not require strong bases or nucleophiles for deprotection and cleavage. Therefore, they can be used for the synthesis of oligonucleotides that contain sensitive functional groups. In contrast, the commonly used technologies cannot because they have to use harsh basic and nucleophilic conditions for deprotection and cleavage [S L Beaucage et al 2011 synthesis of unmodified oligonucleotides, In current protocols in nucleic acid chemistry doi:10.1002/0471142700.nc0300s45].

Compared with the oligonucleotide synthesis technologies, in which exo-amino groups are protected with phenoxyacetyl groups, the embodiments of the invention do not require the basic and nucleophilic potassium methoxide or ammonium hydroxide for deprotection and cleavage. Therefore, they can be used to synthesize oligonucleotides that contain sensitive functional groups. In contrast, the known phenoxyacetyl-based technologies cannot [J C Schulhof et al 1987 Tetrahedron Lett 28:51 doi:10.1016/50040-4039(00) 95646-6, L C J Gillet et al 2005 Nucleic Acids Res 36:1961 doi:10.1093/nar/gki335].

Compared with the oligonucleotide synthesis technologies that use the methyl group for phosphate protection, the embodiments of the invention do not require deprotection under strongly nucleophilic conditions. Therefore, they can be used for the synthesis of oligonucleotides containing sensitive groups. In contrast, the known technologies that use methyl group for phosphate protection cannot because the group has to be deprotected with a strong nucleophile such as thiophenolate [R K Kumar et al 2003 Nucleos Nucleot Nucleic Acids 22:453 doi:10.1081/NCN-120022038].

Compared with the oligonucleotide synthesis technologies that use allyl- or benzyl-based groups for the protection of exo-amino groups, the embodiments of the invention do not require deprotection using palladium-based reagents, which are highly expensive, toxic and difficult to remove from product [Y Hayakawa et al 1990 J Am Chem Soc 112:1691 doi:10.1021/ja00161a006].

Compared with the oligonucleotide synthesis technologies that use o-nitrobenzyl group-based linkers for linking oligonucleotide to a support, the embodiments of the invention do not require cleavage of oligonucleotide from a support using UV light, which can damage oligonucleotides [T J Matray et al 1994 J Am Chem Soc 116:6931 doi: 10.1021/ja00094a056].

Compared with the oligonucleotide synthesis technology that uses the Npe and Npeoc groups for protection, the embodiments of the invention do not require harsh basic conditions for deprotection, and therefore can be used for long oligonucleotide synthesis including those that contain sensitive groups. In contrast, the technology that uses Npe and Npeoc protecting groups requires harsh basic conditions for deprotection, and has only been demonstrated for short oligonucleotide synthesis [R Eritja et al 1992 *Tetrahedron* 48:4171 doi:10.1016/S0040-4020(01)92195-7].

Compared with the oligonucleotide synthesis technologies that use the Fmoc groups for amino protection, the new protecting groups are far more stable during synthesis, and at the same time, are more labile after oxidation during deprotection and cleavage [S C Srivastava et al 2015 U.S. Pat. No. 8,981,076]].

Compared with the oligonucleotide synthesis technology that uses phosphoramidite monomers without amino protection, the embodiments of the invention do not have the problem of difficulty to achieve high selectivity of O-phosphitylation over N-phosphitylation, and therefore can be used to synthesize long oligonucleotides. In contrast, the technology without amino protection cannot be used for long oligonucleotide synthesis [A Ohkubo et al 2004 *J Am Chem Soc* 126:10884 doi:10.1021/ja048125h].

Compared with the oligonucleotide synthesis technologies that involve enzymes or post-synthesis modification, the embodiments of the invention do not require the development of protocols case by case, and the procedure is relatively simple. In contrast, the technologies involving enzymes and post-synthesis modifications require tedious procedures, and need to be developed case by case. More seriously, in many cases, designing such methods is impossible [M M Ali et al 2006 *Angew Chem Int Ed* 45:3136 doi:10.1002/anie.200504441, M Cowart et al 1991 *Biochem* 30:788 doi:10.1021/bi00217a032].

Definitions

The words "and" and "or" in this application may be interchangeable or indicate both.

Oligonucleotides in this invention include unmodified nature oligonucleotides, noncanonical nature oligonucleotides, modified oligonucleotides and oligonucleotide conjugates. They include 2'-deoxyribooligonucleotides (DNA), ribooligonucleotides (RNA), and their analogs and conjugates.

Phosphoramidites in this invention refer to compounds that contain a three-valent phosphorus atom with at least one of the three covalent bonds linked to a three-valent nitrogen atom. The remaining two covalent bonds of the phosphorus atom each connects to a group of atoms via atoms such as nitrogen, oxygen, and carbon.

Sensitive functional groups or sensitive groups are those that are not completely stable under the basic or nucleophilic deprotection or cleavage conditions used in traditional oligonucleotide synthesis technologies. They include, but not limited to, esters, activated esters, arylamides, alkyl halides, benzyl halides, allyl halides, alkyl tosylates, α-halo amides, carbonates, thioesters, sulfonic esters, sultones, phosphate esters, α,β-unsaturated carbonyls, epoxides, aziridines, maleimides, vinyl arenes and methides.

Sulfur-based protecting groups refer to a protecting groups that contain one or two sulfur atoms in the form of sulfide or dithioacetal at the beta-position of a leaving group. The leaving group is the functional group that is being protected or the carbonated functional group. The protecting group features deprotection via oxidation of the sulfur atom or atoms followed by beta-elimination. More detailed description is provided in the summary section with assistance of structures S001-S004.

Sulfur-based linkers refer to cleavable linkers that contain one or two sulfur atoms in the form of sulfide or dithioacetal at the beta-position of a leaving group. The leaving group is the molecule that is being linked to a support or the carbonated version of the molecule. The linker features cleavage via oxidation of the sulfur atom or atoms followed by beta-elimination. More detailed description is provided in the summary section with assistance of structures S001-S004.

Phosphate protection is the protection of the phosphate group in the backbone of oligonucleotides. Before oxidation during oligonucleotide synthesis, the protecting group is part of the inter-nucleotide phosphite triester linkage. Before oligonucleotide synthesis, the protecting group is part of the phosphoramidite monomers.

CE is the 2-cyanoethyl group.

Pn, Bu, Pr, Et and Me are the pentyl, butyl, propyl, ethyl and methyl groups, respectively.

Dim is the 1,3-dithian-2-yl-methyl group.

MeDim is methyl-Dim. It is the 1-(1,3-dithian-2-yl)ethan-1-yl group.

EtDim is ethyl-Dim. It is the 1-(1,3-dithian-2-yl)propan-1-yl group.

PrDim is propyl-Dim. It is the 1-(1,3-dithian-2-yl)butan-1-yl group.

BuDim is butyl-Dim. It is the 1-(1,3-dithian-2-yl)pentan-1-yl group.

PnDim is pentyl-Dim. It is the 1-(1,3-dithian-2-yl)hexan-1-yl group.

Dmoc is the 1,3-dithian-2-yl-methoxycarbonyl group.

dM-Dmoc is dimethyl-Dmoc. It is the 2-(1,3-dithian-2-yl)propan-2-yl-oxycarbonyl group.

MeDmoc is methyl-Dmoc. It is the 1-(1,3-dithian-2-yl)ethan-1-yl-oxycarbonyl group.

EtDmoc is ethyl-Dmoc. It is the 1-(1,3-dithian-2-yl)propan-1-yl-oxycarbonyl group.

PrDmoc is propyl-Dmoc. It is the 1-(1,3-dithian-2-yl)butan-1-yl-oxycarbonyl group.

BuDmoc is butyl-Dmoc. It is the 1-(1,3-dithian-2-yl)pentan-1-yl-oxycarbonyl group.

PnDmoc is pentyl-Dmoc. It is the 1-(1,3-dithian-2-yl)hexan-1-yl-oxycarbonyl group.

Tom is the [(triisopropylsilyl)oxy]methyl group.

DMTr is the 4,4'-dimethoxytrityl group.

MMTr is monomethoxytrityl. It is the 4-methoxytrityl group.

Tr is the trityl group.

Fmoc is the 9-fluorenylmethyloxycarbonyl group.

TBDS is the tert-butyldimethylsilyl group (also abbreviated as TBS or TBDMS).

LDA is lithium diisopropylamide.

Alkyl groups are groups that contain the atoms hydrogen and carbon.

Atoms in the protecting groups and linkers in the invention include their isotopes.

Linker is a chain of atoms that links a molecule to a support or another molecule.

Dmoc linker is a linker that contains the Dmoc functional group. The linker can be cleaved by oxidation followed by beta-elimination under mild conditions.

Solid phase synthesis refers to the synthesis of oligonucleotides on a solid support, which is insoluble in common solvents. Reactions take place on the solid support. Intermediate and product purification is achieved by washing impurities away leaving the product on the support.

Solution phase synthesis refers to the synthesis of oligonucleotides in solution. The product is purified with conventional means as opposed to washing in solid phase synthesis.

Liquid phase synthesis refers to the synthesis of oligonucleotide by attaching the nascent oligonucleotide to a soluble polymer or support. Reactions of the synthesis are performed in solution. Product purification is achieved by precipitation, size exclusion chromatography, membrane filtration or other means utilizing the special properties of the support.

Fluorous affinity-assisted synthesis refers to the synthesis of oligonucleotides by attaching the nascent oligonucleotide to a fluorous material, called fluorous tag or fluorous support. Reactions for the synthesis are performed in solution. Product purification is achieved by fluorous-affinity extraction, chromatography or other means to people having ordinary skill in the art.

Support, which is represented with a circle in the drawings or figures, means materials on which oligonucleotide synthesis is carried out. It includes, but not limited to, those for solid phase synthesis, liquid phase synthesis and fluorous affinity-assisted synthesis.

RP HPLC is reversed-phase high performance liquid chromatography.

BRIEF DESCRIPTION OF DRAWINGS

FIG. 10. Synthesis of example phosphoramidites with sensitive groups that can be incorporated onto the 5'-end of oligonucleotides.

FIG. 11. Preparation of an example support that contains a Dmoc linker and can be used to introduce a sensitive group onto the 3'-end of oligonucleotides.

FIG. 12. MeDmoc-MeDim-phosphoramidites and Dmoc linker for oligonucleotide synthesis in the 5' to 3' direction.

FIG. 17. MeDmoc-MeDim-phosphoramidites and Dmoc linker for 2'-OCH$_3$ oligonucleotide synthesis.

FIG. 18. MeDmoc-MeDim-phosphoramidites and Dmoc linker for 2'-F oligonucleotide synthesis.

FIG. 19. Tagging agents for introducing a hydrophobic tag to the 5'-end of oligonucleotides to assist RP HPLC purification.

FIG. 20. Capping agents that can overcome the problem of cap-exchange in sensitive oligonucleotide synthesis.

FIG. 23. Deprotection and cleavage of oligonucleotides assembled with Dmoc-Dim-phosphoramidites.

FIG. 24. Deprotection and cleavage of oligonucleotides assembled with AlkylDmoc-AlkylDim- and Dmoc-Dim phosphoramidites.

FIG. 26. RP HPLC profile of crude oligonucleotide S140a.

FIG. 27. RP HPLC profile of pure oligonucleotide S140a.

FIG. 28. MALDI-TOF MS of oligonucleotide 140a.

FIG. 29. RP HPLC profile of crude trityl-on oligonucleotide S140k.

FIG. 30. RP HPLC profile of pure trityl-on oligonucleotide S140k.

FIG. 31. RP HPLC profile of crude trityl-off oligonucleotide S140k.

FIG. 32. RP HPLC profile of pure trityl-off oligonucleotide S140k.

FIG. 33. MALDI-TOF MS of trityl-on oligonucleotide S140k.

FIG. 34. MALDI-TOF MS of trityl-off oligonucleotide S140k.

FIG. 35. RP HPLC profile of crude trityl-on oligonucleotide S140p.

FIG. 36. RP HPLC profile of pure trityl-on oligonucleotide S140p.

FIG. 37. RP HPLC profile of crude trityl-off oligonucleotide S140p.

FIG. 38. RP HPLC profile of pure trityl-off oligonucleotide S140p.

FIG. 39. MALDI-TOF MS of trityl-on oligonucleotide S140p.

FIG. 40. MALDI-TOF MS of trityl-off oligonucleotide S140p.

FIG. 41. RP HPLC profile of crude trityl-on oligonucleotide S140r.

FIG. 42. MALDI-TOF MS of trityl-on oligonucleotide S140r.

FIG. 43. RP HPLC profile of crude trityl-off oligonucleotide S140r.

FIG. 44. MALDI-TOF MS of trityl-off oligonucleotide S140r.

FIG. 45. RP HPLC profile of crude trityl-on oligonucleotide S140s.

FIG. 46. MALDI-TOF MS of trityl-on oligonucleotide S140s.

FIG. 47. RP HPLC profile of crude trityl-off oligonucleotide S140s.

FIG. 48. MALDI-TOF MS of trityl-off oligonucleotide S140s.

FIG. 49. RP HPLC profile of crude trityl-on oligonucleotide S140t.

FIG. 50. MALDI-TOF MS of trityl-on oligonucleotide S140t.

FIG. 51. RP HPLC profile of crude trityl-off oligonucleotide S140t.

FIG. 52. MALDI-TOF MS of trityl-off oligonucleotide S140t.

Figure 1:
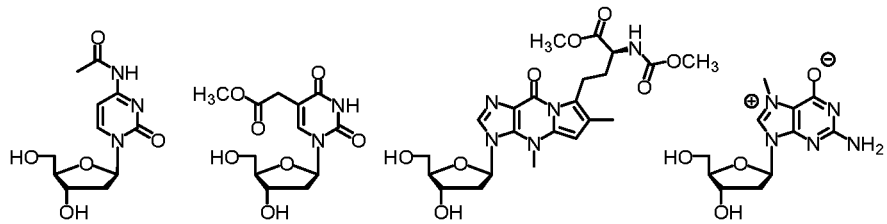
FIG. 1. Examples of non-canonical natural nucleosides that contain sensitive groups.
Figure 2:
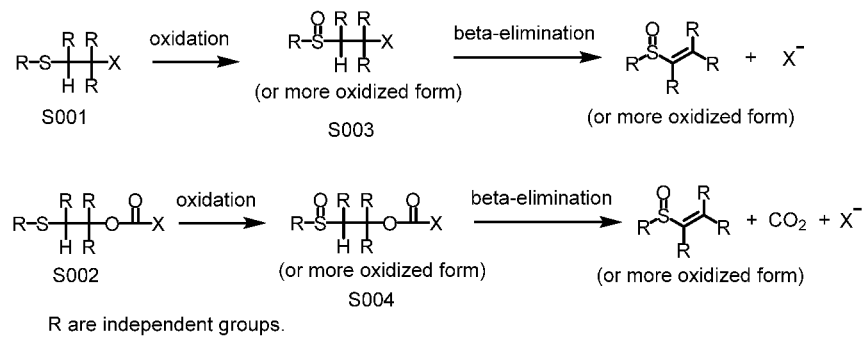
FIG. 2. Deprotection and cleavage of the sulfur-based protecting groups and linkers.

DETAILED DESCRIPTION OF THE INVENTION
This invention comprises the use of the sulfur-based groups represented by S001 and S002 for protection and linking in oligonucleotide synthesis.
Some embodiments of the invention are related to the structure S005:
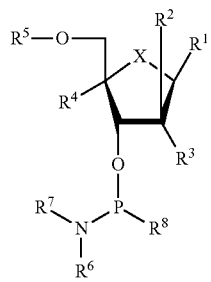
S005
Wherein $R^1$, which is independent from the independent groups $R^2$-$R^8$, is selected from S006-015:
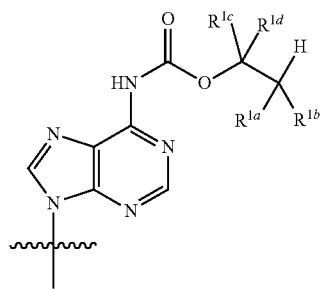
S006
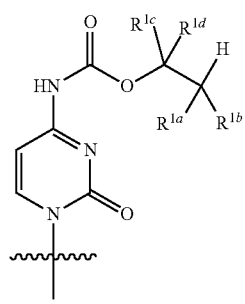
S007
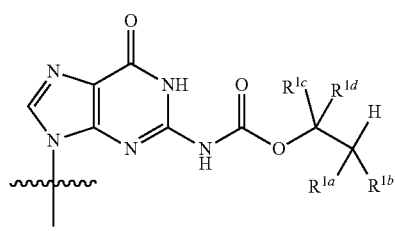
S008
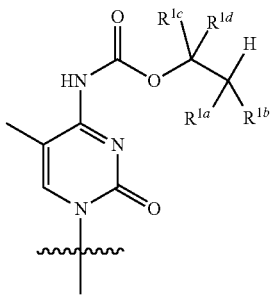
S009
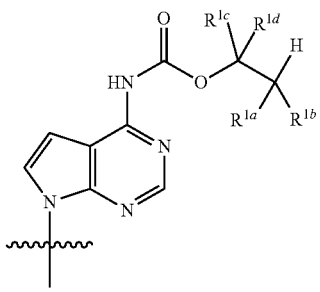
S010
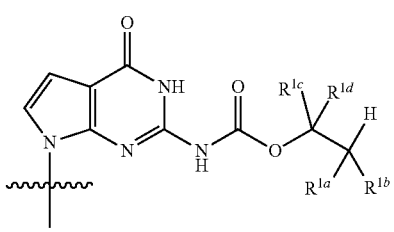
S011
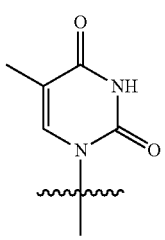
S012
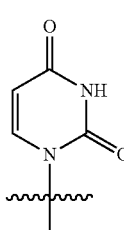
S013
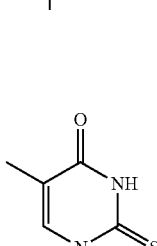
S014

-continued

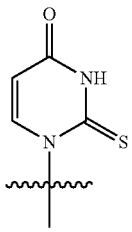
S015

Wherein $R^{1a}$=—$SR^{1a1}$ with $R^{1a1}$ being an alkyl group, derivatized alkyl group, aryl group or derivatized aryl group; and $R^{1b}$=H, alkyl group, derivatized alkyl group, aryl group, derivatized aryl group, or $R^{1a}$ with independent $R^{1a1}$; or $R^{1a}$-$R^{1b}$=—$S[C(R^{1a2})R^{1a3}]_nS$—, —$S\{[C(R^{1a2})R^{1a3}]_nO[C(R^{1a2})R^{1a3}]_m\}_pS$— or —$S\{[C(R^{1a2})R^{1a3}]_nS[C(R^{1a2})R^{1a3}]_m\}_pS$— wherein independently $R^{1a2}$ and $R^{1a3}$ are H or alkyl groups independently in the repetitions, and m, n and p are independent integers;

$R^{1c}$ and $R^{1d}$ are independent H, alkyl group, derivatized alkyl group, aryl group, or derivatized aryl group including instances wherein $R^{1c}$ and $R^{1d}$ are connected to form a cycle;

$R^2$=H or F;

$R^3$ is defined differently in two different situations, in which $R^4$ is a H or not a H:

In the situations that $R^4$ is a H, $R^3$=—H, —F, —$OR^{3a}$, —$O\{[C(R^{3b})R^{3c}]_nO\}_mR^{3d}$, or S016-023 wherein $R^{3a}$ and $R^{3d}$ are alkyl groups, $R^{3b}$ and $R^{3c}$ are independently H or alkyl group independently in the repetitions, n and m are integers; S016-023 are:

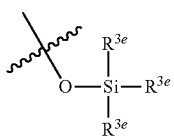
S016

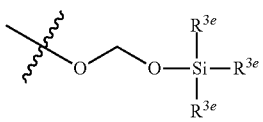
S017

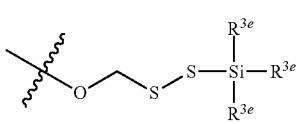
S018

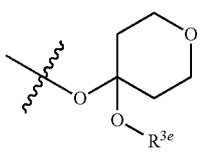
S019

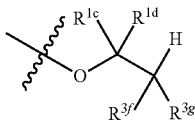
S020

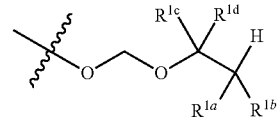
S021

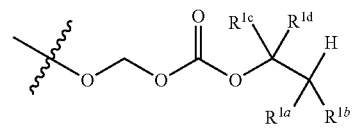
S022

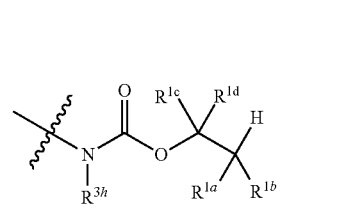
S023

Wherein $R^{1a}$, $R^{1b}$, $R^{1c}$ and $R^{1d}$ are defined as in 5005 for $R^1$;

$R^{3e}$ are independent alkyl, derivatized alkyl, aryl or derivatized aryl groups;

$R^{3f}$=$R^{1a}$ and $R^{3g}$=$R^{1b}$ when $R^1$ is S006-011;

$R^{3f}$ and $R^{3g}$, when $R^1$ is S012-015, are independently —$SR^{3f1}$ with $R^{3f1}$ being an alkyl derivatized alkyl, aryl or derivatized aryl group; or $R^{3f}$-$R^{3g}$=—$S[C(R^{3f2})R^{3f3}]_nS$—, —$S\{[C(R^{3f2})R^{3f3}]_nO[C(R^{3f2})R^{3f3}]_m\}_pS$—, or —$S\{[C(R^{3f2})R^{3f3}]_nS[C(R^{3f2})R^{3f3}]_m\}_pS$— wherein independently $R^{3f2}$ and $R^{3f3}$ are H or alkyl groups independently in the repetitions, and m, n and p are independent integers;

$R^{3h}$ is H, alkyl group, or derivatized alkyl group;

In the situations that $R^4$ is not a H, $R^3$-$R^4$=—$OCH_2$—, —$O(CH_2)_2$— or —$OCH(CH_3)$—;

$R^5$ is defined by S024, S025 or S026:

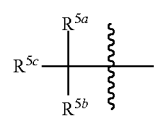
S024

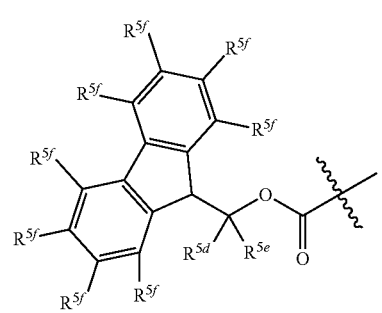
S025

15

-continued

S026
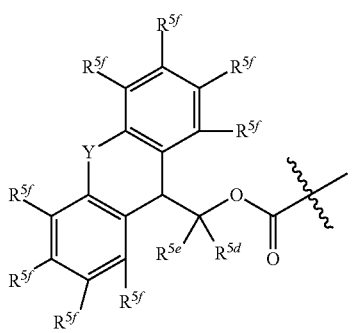

Wherein $R^{5a}$, $R^{5b}$ and $R^{5c}$ are independent H, alkyl groups, derivatized alkyl groups, alkoxyl groups, aryl groups and derivatized aryl groups; $R^{5d}$ and $R^{5e}$ are independent H, alkyl groups and derivatized alkyl groups including groups with the two groups connected to form a cycle; $R^{5f}$ are independent H, halogens, alkyl groups, derivatized alkyl groups, alkoxyl groups, amino groups, substituted amino groups, acylated amino groups, aryl groups and derivatized aryl groups; and Y is a hydrocarbon linkage, —O—, —S—, or —N[$(Y^1)Y^2$]—, where $Y^1$ and $Y^2$ are independent H, alkyl, and acyl groups;

$R^6$ and $R^7$ are independent alkyl groups or derivatized alkyl groups including those with the two groups linked together to form a nitrogen-containing cycle;

$R^8$ is defined as any of the following groups:

$R^8$=S027 when $R^1$ is any of S006-015, wherein S027 is:

S027
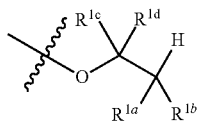

Wherein $R^{1a}$, $R^{1b}$, $R^{1c}$ and $R^{1d}$ are defined as in 5005 for $R^1$;

$R^8$=alkyl group, derivatized alkyl group or alkoxyl group when $R^1$ is defined by S006-011, or when $R^1$ is defined by S012-015 and $R^3$ is defined by S020-023;

$R^8$=—O[C($R^{8a}$)$R^{8b}$C(H)$R^{8c}$]CN, wherein $R^{8a}$, $R^{8b}$, and $R^{8c}$ are independent H or alkyl groups, when $R^1$ is defined by S009-011, or when $R^1$ is defined by S006-008 and S012-015 and $R^3$ is defined by S020-023, or when $R^1$ is defined by S006-008 and $R^{1c}$ and $R^{1d}$ are not both H, or when $R^1$ is defined by S006-008 and $R^{1a}$-$R^{1b}$ is not —S(CH$_2$)$_3$S—;

X=—O—, —S—, —CH$_2$— or S028:

S028
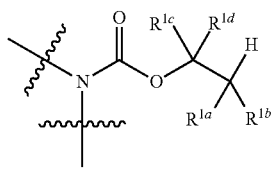

Wherein $R^{1a}$, $R^{1b}$, $R^{1c}$ and $R^{1d}$ are defined as in 5005 for $R^1$.

16

Some embodiments of the invention are related to S029:

S029
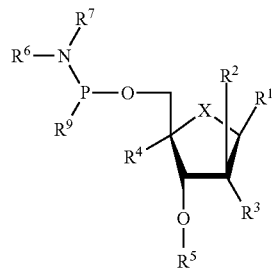

Wherein, independently, $R^1$, $R^2$, $R^4$, $R^5$, $R^6$, $R^7$ and X are defined as in S005;

$R^3$ is defined as in S005 except that $R^{3f}$ and $R^{2g}$ in S020 are $R^{1a}$ and $R^{1b}$ in the cases of $R^1$ being any of S005-015;

$R^9$ is an alkyl group, derivatized alkyl group, alkoxyl group, —O[C($R^{9a}$)$R^{9b}$C(H)$R^{9c}$]CN wherein $R^{9a}$, $R^{9b}$, and $R^{9c}$ are independent H or alkyl groups, or S027.

Some embodiments of the invention are related to the structure S030:

S030
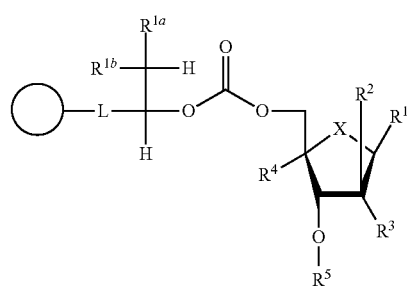

Wherein $R^1$, $R^{1a}$, $R^{1b}$, $R^2$, $R^3$, $R^4$ and X are defined as in S005; $R^5$ is defined as in S005 or H; and L is a chain of atoms that links the molecule to a support.

Some embodiments of the invention are related to S031:

S031
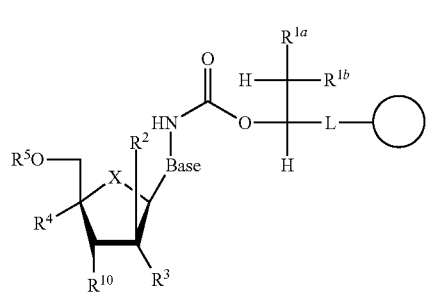

Wherein $R^{1a}$, $R^{1b}$, $R^2$, $R^3$, $R^4$, $R^5$, X and L are defined as in S030; $R^{10}$ is a sensitive group, or —O$R^{10a}$ with $R^{10a}$ being removable under the conditions orthogonal to the conditions that can be used to remove $R^5$, or a permanent group; and Base is defined by S032-035 with the nitrogen atom shown in the formula S031 connected to the carbon atom instead of the nitrogen atom indicated in S032-035:

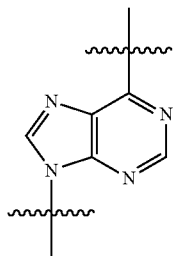

S032

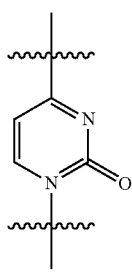

S033

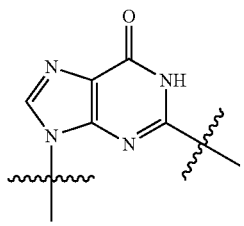

S034

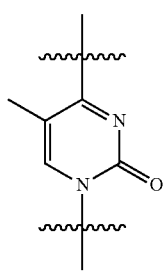

S035

Some embodiments of the invention are related to S036, and their use as the last nucleoside phosphoramidite monomer in oligonucleotide synthesis to introduce a hydrophobic tag (i.e. $R^{11}$ in S036) to the 5'-end of oligonucleotide to assist RP HPLC purification in the context of using one or more phosphoramidites with sulfur-based protecting groups as monomers for oligonucleotide synthesis. The tag is stable under the deprotection and cleavage conditions involving sodium periodate but can be removed under acidic conditions without damaging the oligonucleotide and sensitive groups in it. S036 is:

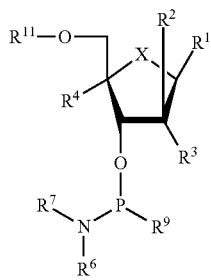

S036

Wherein $R^1$, $R^2$, $R^3$, $R^4$, $R^6$ and $R^7$ are defined as in S005; $R^9$ is an alkyl group, alkoxyl group, —O[C($R^{9a}$)$R^{9b}$C(H)$R^{9c}$]CN wherein $R^{9a}$, $R^{9b}$, and $R^{9c}$ are independent H or alkyl groups, or defined by S027; and $R^{11}$ is a hydrophobic group defined by S037:

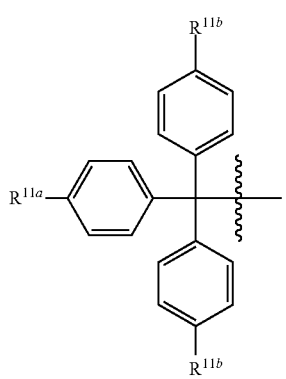

S037

Wherein $R^{11a}$ is a H, alkyl group, derivatized alkyl group, or alkoxyl group; and $R^{11b}$ are independent H, alkyl group, derivatized alkyl group, or halogen.

Some embodiments of the invention are related to the use of S038 as the last nucleoside phosphoramidite monomer in oligonucleotide synthesis to introduce a hydrophobic tag (i.e. $R^{11}$ in S038) to the 3'-end of oligonucleotide to assist RP HPLC purification in the context of using phosphoramidites with sulfur-based protecting groups as monomers for oligonucleotide synthesis. The tag is stable under the deprotection and cleavage conditions involving sodium periodate but can be removed under acidic conditions without damaging the oligonucleotide and sensitive groups in it. S038 is:

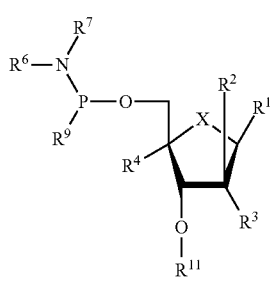

S038

Wherein $R^1$, $R^2$, $R^3$, $R^4$, $R^6$, $R^7$, $R^9$, $R^{11}$ and X are defined as in S036.

Some embodiments of the invention are related to the use of S039 as a reagent for capping failure sequences generated in the coupling step during oligonucleotide synthesis. Cap-exchange is an issue when phosphoramidites with sulfur-based protecting groups are used as monomers for oligonucleotide synthesis because the typically used acyl capping agent can replace the sulfur-based groups, and then the acyl groups cannot be removed during oligonucleotide deprotection. By using a phosphorus-based capping agent, cap-exchange can be avoided. S039 is:

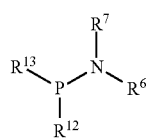

S039

Wherein $R^6$ and $R^7$ are defined as in S005, and $R^{12}$ and $R^{13}$ are independent alkyl, derivatized alkyl, alkoxyl, derivatized alkoxyl including, but not limited to, 2-cyanoethoxyl, and substituted amino groups including those identical to —N($R^6$)$R^7$.

Some embodiments of the invention are related to the use of S040 as a reagent for capping failure sequences generated in the coupling step during oligonucleotide synthesis. Cap-exchange is an issue when phosphoramidites with sulfur-based protecting groups are used as monomers for oligonucleotide synthesis because the typically used acyl capping agent can replace the sulfur-based groups, and then the acyl groups cannot be removed during oligonucleotide deprotection. When S040 is used as the capping agent, even if cap-exchange occurs, the replacing group is still a sulfur-based group, and they can be removed during deprotection under the mild oxidative condition. S040 is:

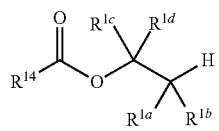

S040

Wherein $R^{1a}$, $R^{1b}$, $R^{1c}$ and $R^{1d}$ are defined as in S005; and $R^{14}$ is a leaving groups including, but not limited to, nitrophenoxide group, flourophenoxide groups and halides.

The following examples are provided to demonstrate the feasibility of the invention, and to teach the people having ordinary skill in the art of organic chemistry and nucleic acid chemistry to practice the invention. The examples must not be used to limit the scope of the invention.

Figure 3:
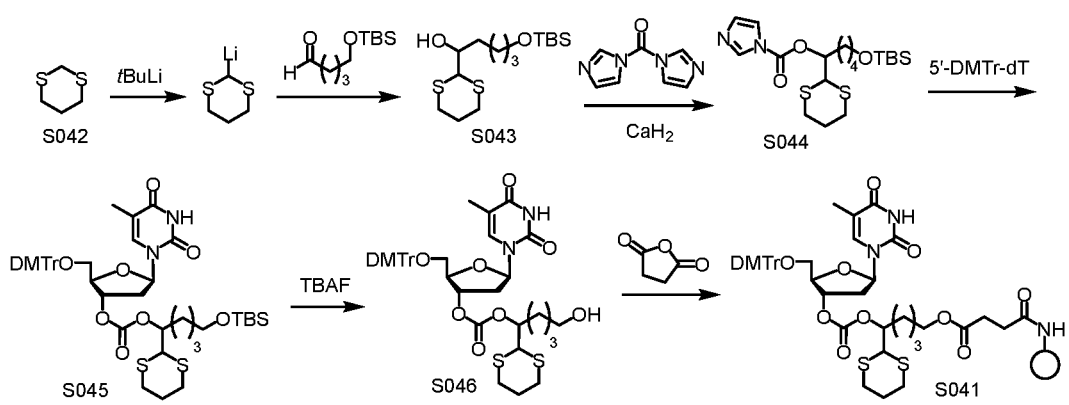
FIG. 3. Preparation of a solid support that contains a Dmoc linker.

In some embodiments, in which the oligonucleotides (sensitive or insensitive ones) are synthesized on a support, and after synthesis, are needed to be cleaved from the support, materials such as S041 that contain a Dmoc linkage is required. The preparation of S041 is provided in FIG. 3. Detailed conditions are provided in the Experimental Examples section. The Dmoc linkage can be cleaved under nearly non-basic and non-nucleophilic conditions, and therefore sensitive functional groups in the oligonucleotides are not destroyed during cleavage.

In some embodiments, the oligonucleotides (sensitive or insensitive ones) do not need to be cleaved from a support after synthesis or need to be deprotected first and then cleaved in a subsequent step. In these cases, known linkers including permanent linkers and linkers that are cleavable under reported conditions can be used.

Figure 4:
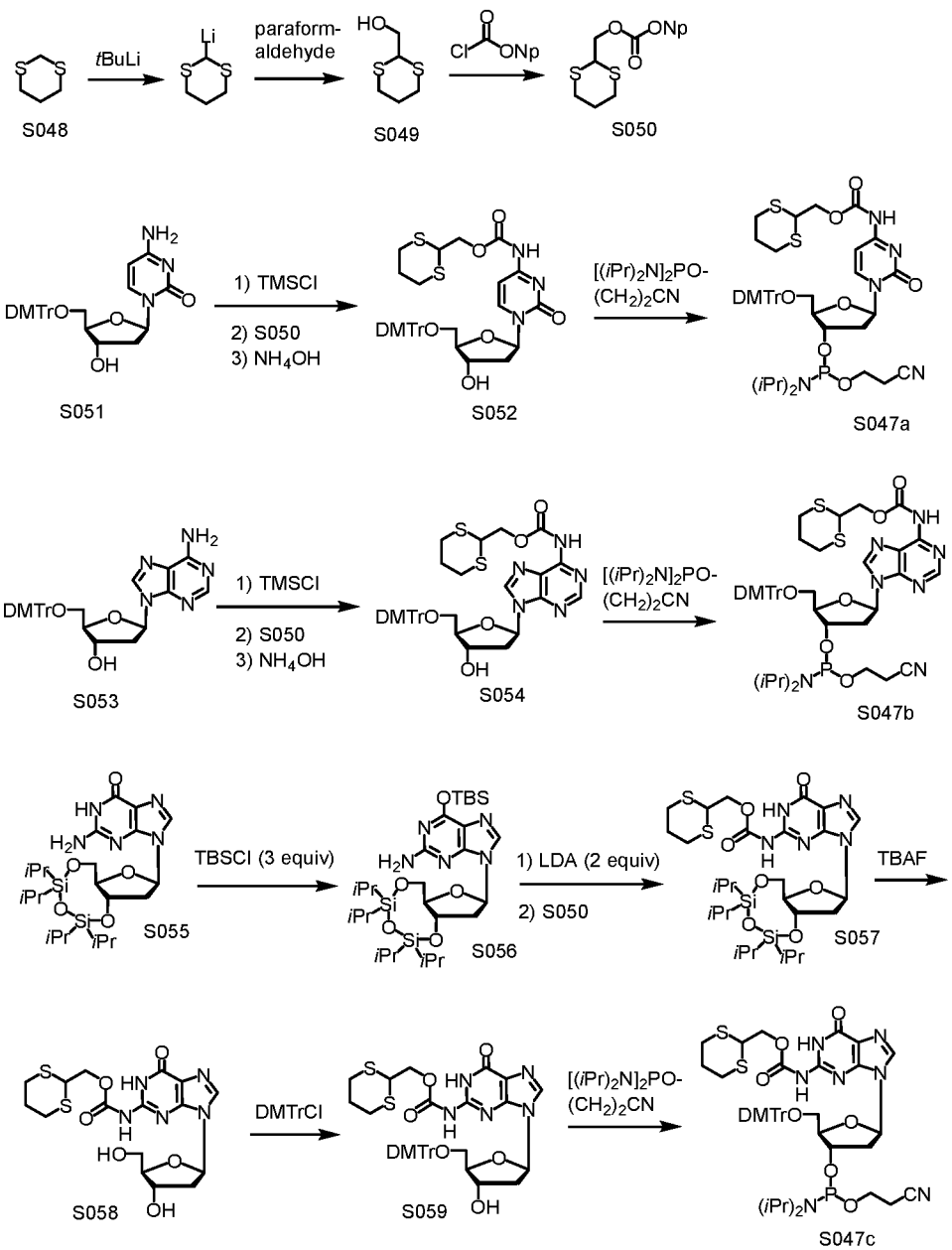
FIG. 4. Synthesis of Dmoc-CE-phosphoramidites.

Some embodiments use the Dmoc phosphoramidite monomers S047a-c for oligonucleotide synthesis. A method to synthesize them is provided in FIG. 4. Details are provided in the Experimental Examples section. The synthesis of the intermediate S059, which was required for the synthesis of the Dmoc-dG phosphoramidite monomer S047c, was particularly challenging. A special procedure different from the synthesis of S052 and S054 was used. The protected dG nucleoside S056 was prepared, and treated with two equivalents of the strong base LDA followed by one equivalent S050 to give S057. S057 was then deprotected with TBAF to give S058, which was protected with DMTrCl to give the needed S059. It is remarkable that for converting S056 to S057, the excess strong base—LDA—could be applied, and the materials survived the conditions. In particular, the excess LDA did not remove the Dmoc protecting group during the synthesis, which was surprising.

Figure 5:
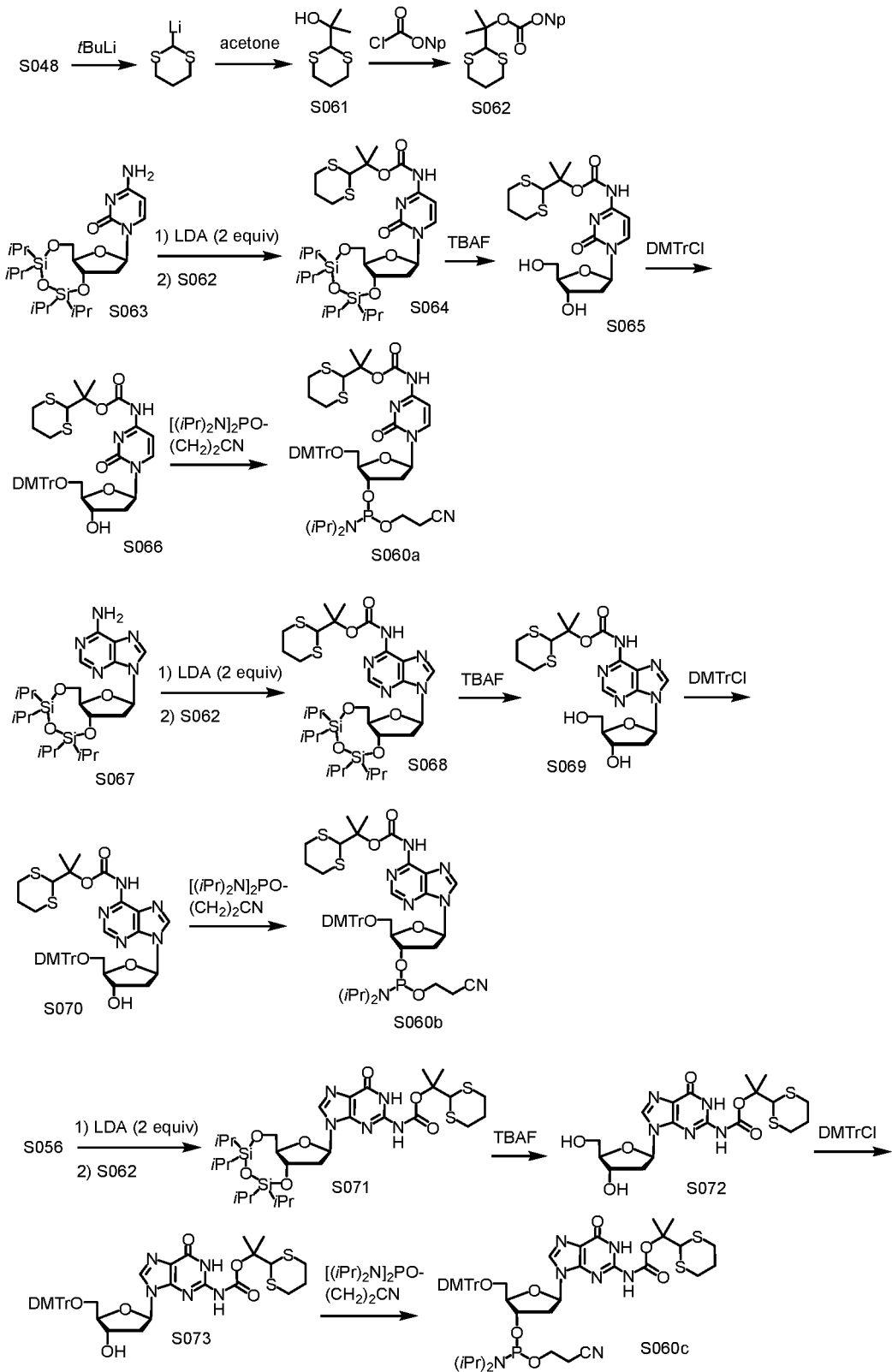
FIG. 5. Synthesis of dM-Dmoc-CE-phosphoramidites.

Some embodiments use the dM-Dmoc phosphoramidite monomers S060a-c for oligonucleotide synthesis. A method to synthesize them is provided in FIG. 5. Details are provided in the Experimental Examples section. Because the reagent S062 for the preparation of dM-Dmoc phosphoramidites are more hindered, to achieve satisfactory results, the more reactive conditions involving two equivalents of LDA described for the synthesis of S058 FIG. 4) were used for the synthesis of all the corresponding dM-Dmoc intermediates S065, S069 and S072, which were needed for the synthesis of S060a-c.

Figure 6:
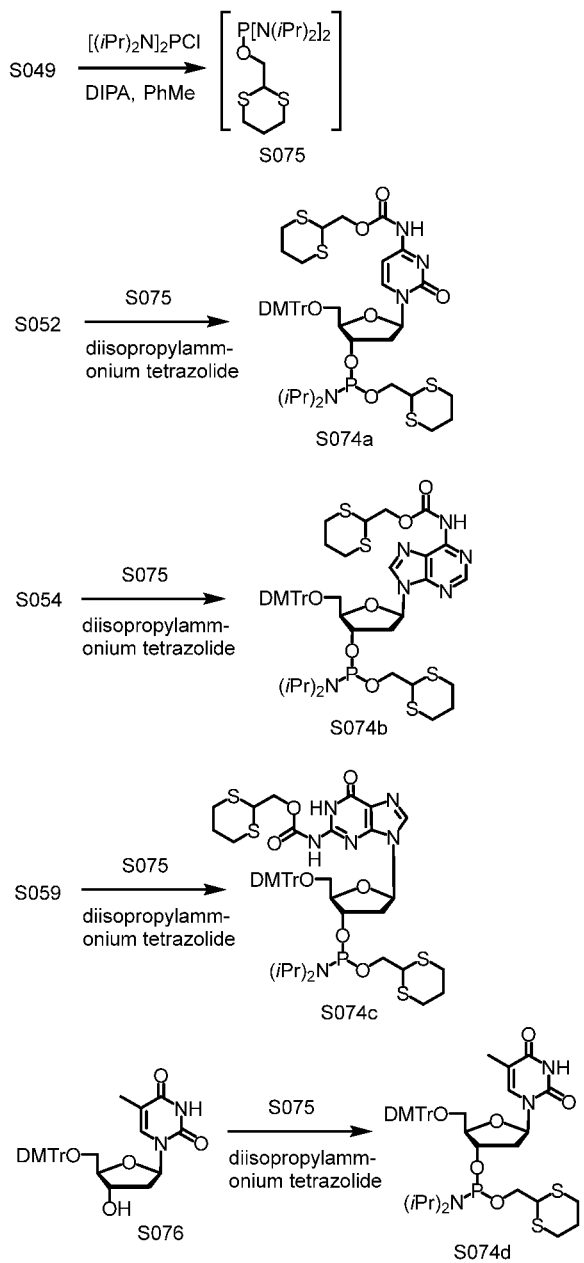
FIG. 6. Synthesis of Dmoc-Dim-phosphoramidites.

Some embodiments use the Dmoc-Dim phosphoramidite monomers S074a-d for oligonucleotide synthesis. A method to synthesize them is provided in FIG. 6. Details are provided in the Experimental Examples section. The required intermediates S052, S054 and S059 were prepared using the more reactive conditions involving two equivalents of LDA described in FIG. 4 because these conditions gave cleaner products and better yields. The phosphitylation agent S075 was prepared from S049 and used directly without purification because the compound was sensitive to moisture and oxygen.

Figure 7:
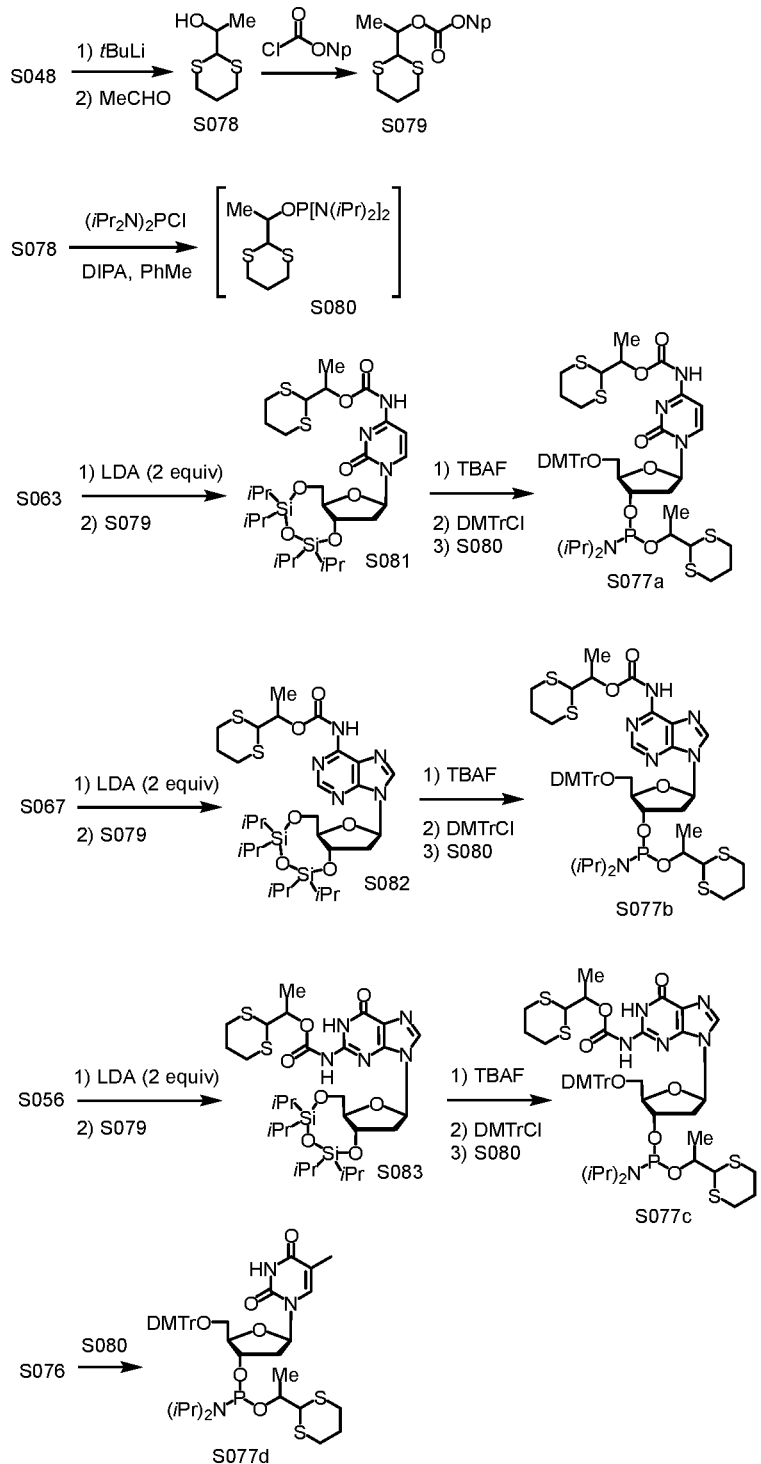
FIG. 7. Synthesis of MeDmoc-MeDim-phosphoramidites.

Some embodiments use the MeDmoc-MeDim phosphoramidite monomers S077a-d for oligonucleotide synthesis. A method to synthesize them is provided in FIG. 7.

Figure 8:
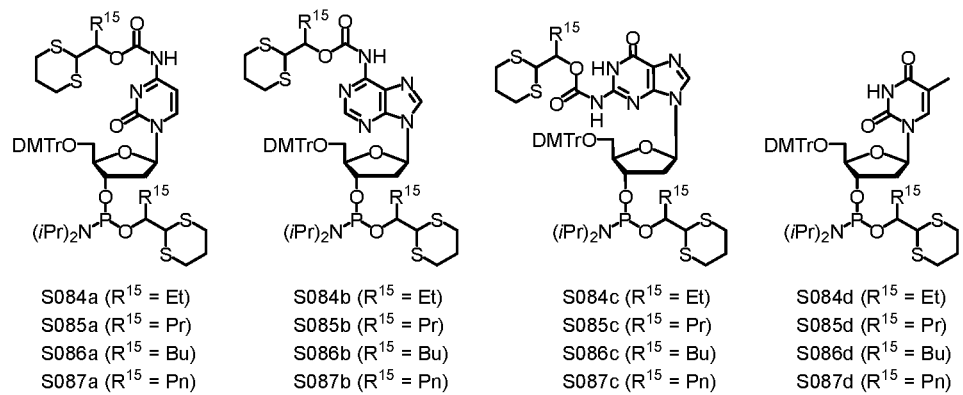
FIG. 8. EtDmoc-EtDim-, PrDmoc-PrDim-, BuDmoc-BuDim-, PnDmoc-PnDim-phosphoramidites.

Some embodiments use EtDmoc-EtDim (S084a-d), PrDmoc-PrDim (S085a-d), BuDmoc-BuDim (S086a-d) and PnDmoc-PnDim (S087a-d) phosphoramidite monomers, which are shown in FIG. 8, for oligonucleotide synthesis. They can be synthesized by individuals having ordinary skill in the art of organic synthesis using procedures similar to that shown in FIG. 7.

Figure 9:
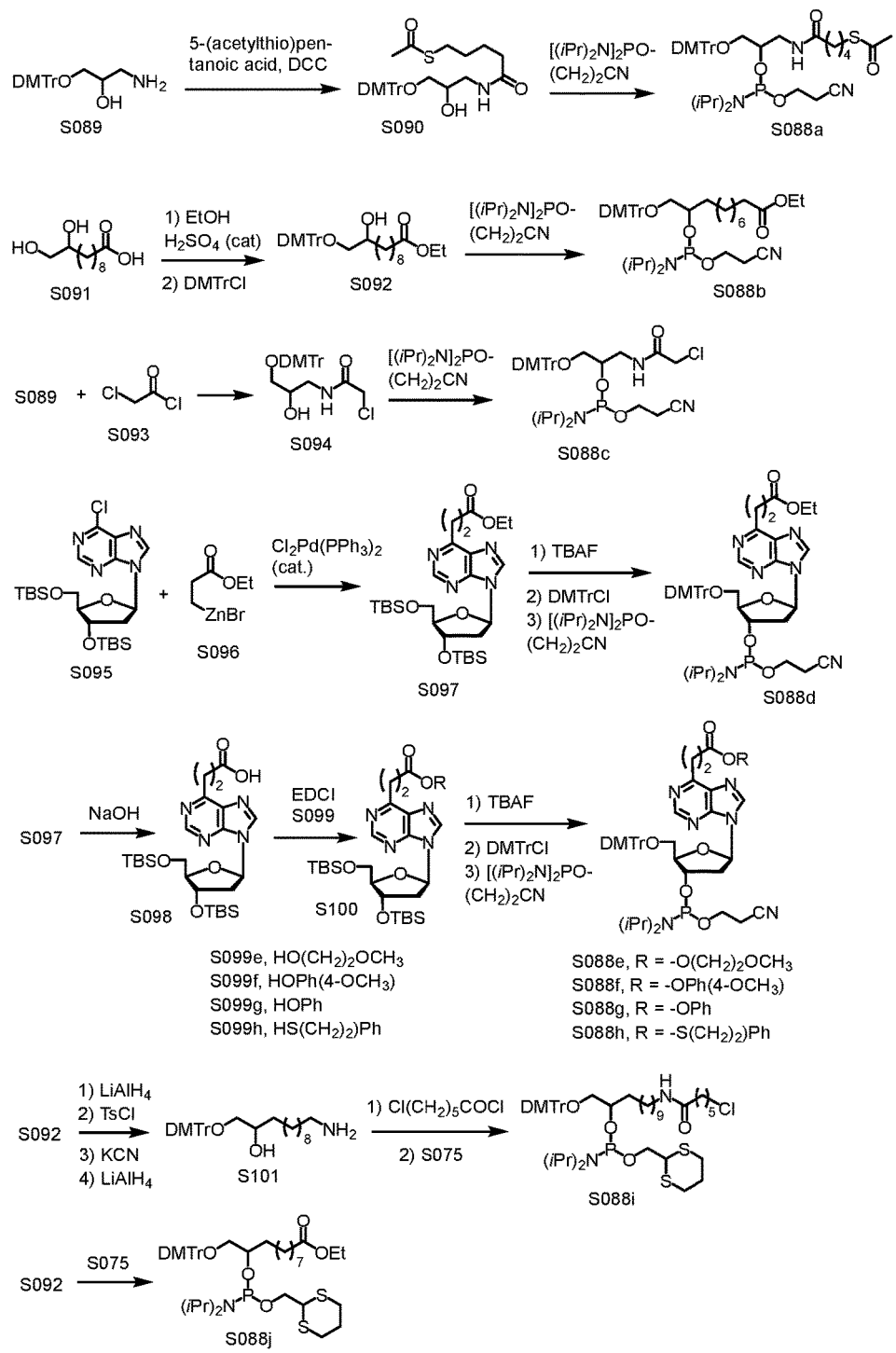
FIG. 9. Synthesis of example phosphoramidites with sensitive groups that can be incorporated into the middle of oligonucleotides.

Some embodiments of the invention can be used to incorporate one or more sensitive groups into the middle of oligonucleotides. Several example phosphoramidite monomers containing a sensitive group that are useful for the application are provided in FIG. 9. Selected synthesis details are provided in the Experimental Examples section.

Some embodiments of the invention can be used to incorporate a sensitive group onto the 5'-end of oligonucleotides. Several example phosphoramidite monomers containing a sensitive group that are useful for the application are provided in FIG. 10. In S102a, the sensitive group is an alkyl chloride. In S102b, the sensitive group is an acetyl ester.

Some embodiments of the invention can be used to incorporate a sensitive group onto the 3'-end of oligonucleotides. One of the embodiments comprises a Dmoc-linker that can anchor the nascent oligonucleotide to a support via the amino group of a nucleobase. One of such linkers is S103 (FIG. 11), which can be synthesized from S105 [A F Khattab et al 1998 *Nucleos Nucleot* 17:2351 doi:10.1080/07328319808004323]. Using S103 as the support, and phosphoramidite monomers with sulfur-based protecting groups, oligonucleotides containing a sensitive 3'-acetyl group such as S104 can be synthesized.

Some embodiments of the invention are capable of oligonucleotide synthesis from the 5'-end to 3'-end direction instead of the typical 3' to 5' direction. In some applications, synthesis from 5' to 3' direction may be required or has significant advantages [SC Srivastava et al 2010 PCT Application WO2010062404A2]]. Some embodiments of the invention comprising the example phosphoramidite monomers and linker S107a-e (FIG. 12) can be used for this application. The synthesis of one of the monomers and linkers are provided. Others can be synthesized similarly. Synthesis of oligonucleotides from 5' to 3' direction, in particular, provides an alternative for the synthesis of oligonucleotides that have a sensitive group at their 3'-end.

Figure 13:
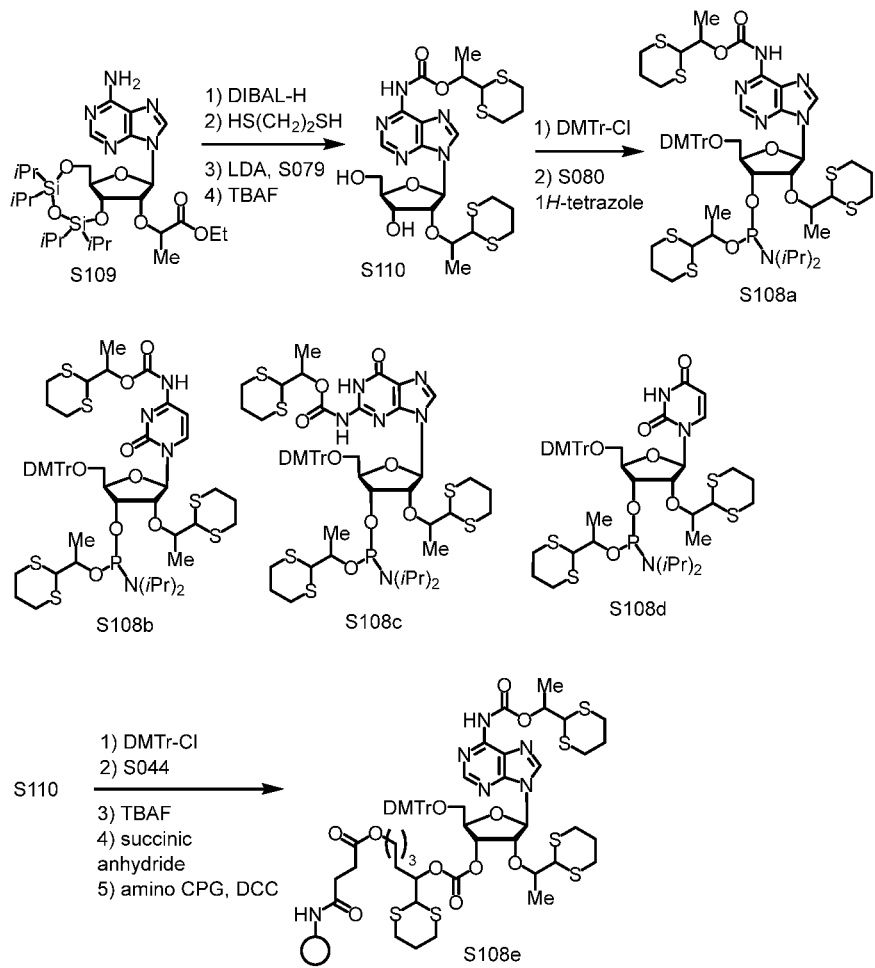
FIG. 13. MeDmoc-MeDim-phosphoramidites and Dmoc linker for RNA synthesis.
Figure 14:
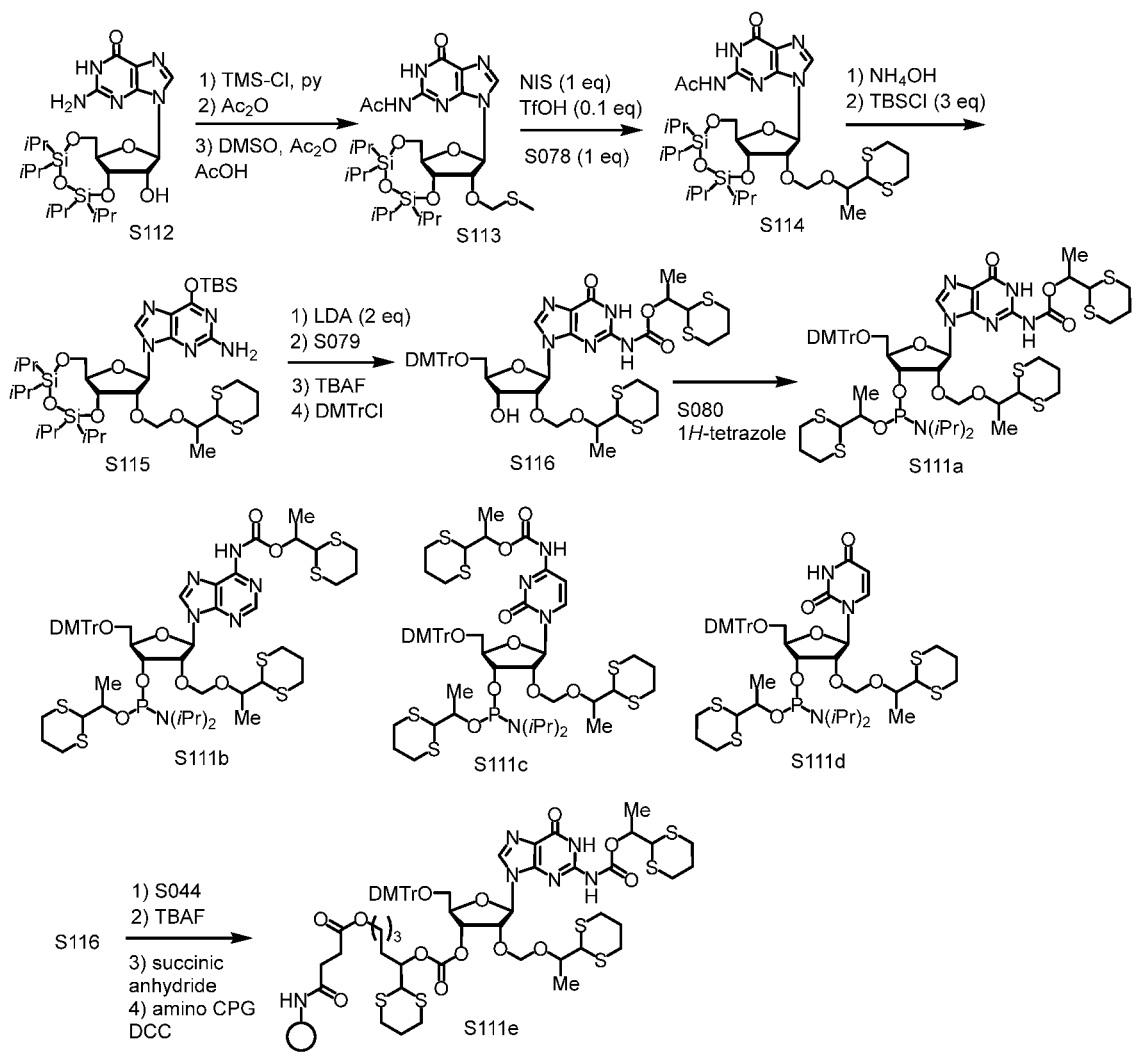
FIG. 14. Less hindered MeDmoc-MeDim-phosphoramidites and Dmoc linker for RNA synthesis.
Figure 15:
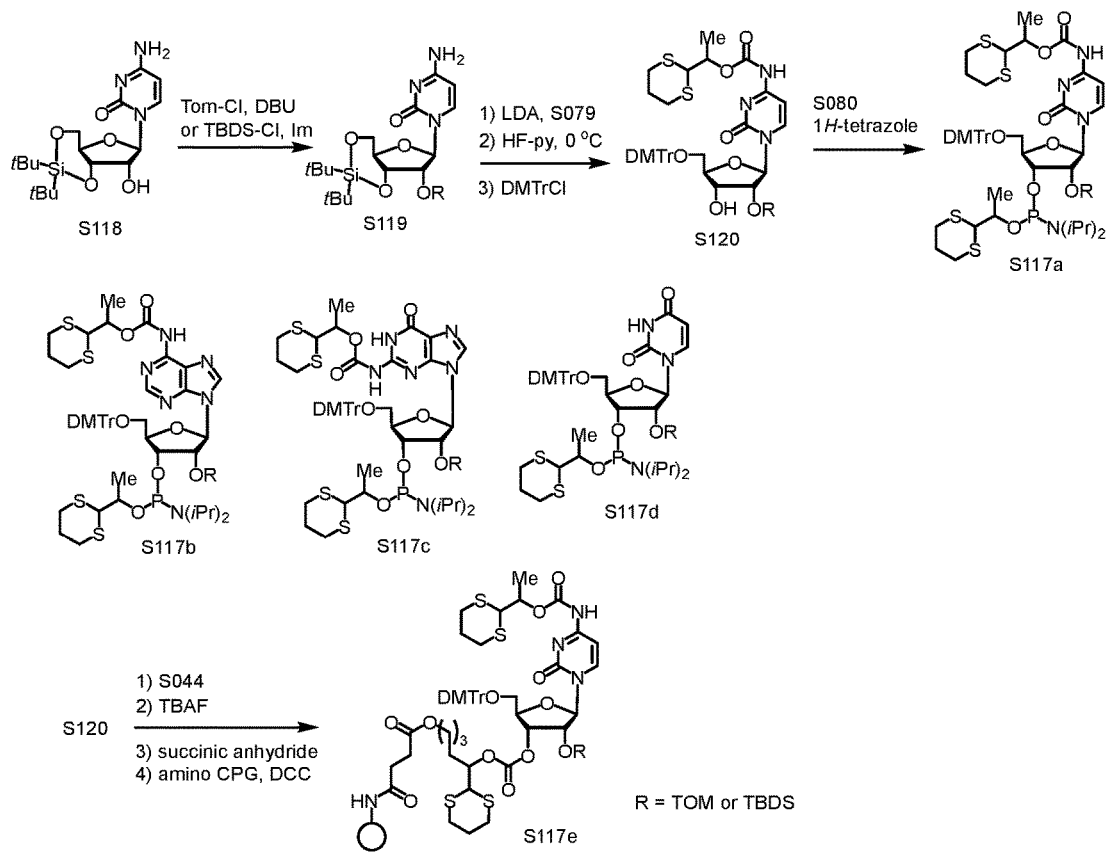
FIG. 15. MeDmoc-MeDim-phosphoramidites and Dmoc linker with 2'-TOM or 2'-TBDS protection for RNA synthesis.

Some embodiments of the invention use the phosphoramidite monomers and linker S108a-e (FIG. 13), S111a-e (FIG. 14), or S117a-e (FIG. 15) for oligonucleotide synthesis. These embodiments and other similar embodiments can be used for the synthesis of RNA and their analogs including those that contain sensitive groups. For the synthesis of the compounds, installation of the MeDim group at the 2'-OH position is needed. An example is provided in FIG. 13. S109 can be prepared according to literature procedure [S X Jin et al2005 *J Org Chem* 70:4284 doi:10.1021/jo0500611, R Smicius et al 2008 *J Org Chem* 73:4994 doi:10.1021/jo800451m, J T Goodwin et al 1996 *J Am Chem Soc* 118:5207 doi:10.1021/ja960091t]. The compound can be converted to S110 in four steps, which can then be converted to S108a using routine chemistry. The synthesis of 108e can be achieved using a similar procedure for the synthesis of S041. Examples for the synthesis of S111a-e are provided in FIG. 14. S114 can be prepared following procedures used for the synthesis of similar compounds from S112 in the literature [J Cieslak et al 2007 *Org Lett* 9:671 doi:10.1021/010629824]. Following well-established protocols, S114 can then be converted to S115, from which the target phosphoramidite S111a can be synthesized using well-known reactions. The synthesis of Sill e can be achieved following procedures used the synthesis of S041. Examples for the synthesis of S117a-e are provided in FIG. 15. S119 can be prepared following reported procedures from S118 [V Serebryany et al 2003 *Nucleos Nucleot Nucl* Acids 22:1007 doi:10.1081/Ncn-120022724]. Installation of the MeDmoc protecting group can be achieved using LDA and S079. Selective deprotection of the 3' and 5' silyl group without affecting 2'-silyl group is achievable with HF-pyridine [V Serebryany et al 2003 *Nucleos Nucleot Nucl Acids* 22:1007 doi:10.1081/Ncn-120022724]. S120 can then be converted to S117a using well-known reactions. The synthesis of all the materials does not involve in any new reactions. It can be accomplished by individuals having ordinary skill in the art in organic chemistry.

Figure 16:
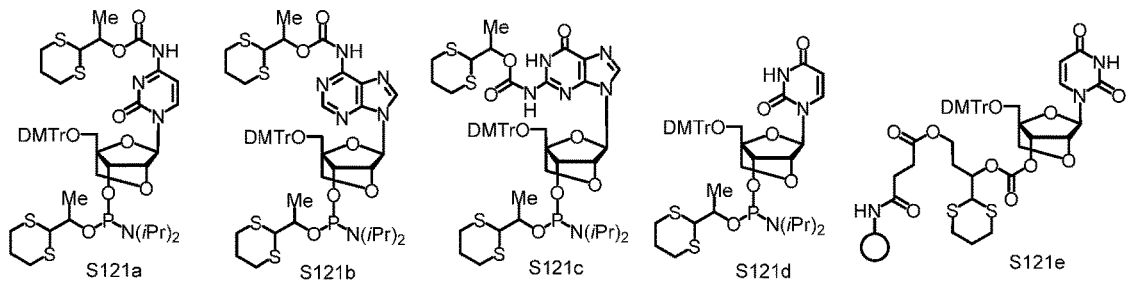
FIG. 16. MeDmoc-MeDim-phosphoramidites and Dmoc linker for LNA synthesis.

Some embodiments of the invention use the phosphoramidite monomers and linker S121a-e (FIG. 16) for oligonucleotide synthesis. These and similar embodiments can be used to synthesize locked nucleic acids (LNA) or oligonucleotides that contain one or more locked nucleosides including those that contain one or more sensitive groups. S121a-e can be prepared from commercially available locked nucleosides [AA Koshkin et al 2001 *J Org Chem* 66:8504 doi:10.1021/jo010732p] using similar procedures for the preparation of S077a-d (FIG. 7) and S041 FIG. 3) by individuals having ordinary skill in the art in organic synthesis.

Some embodiments of the invention use the phosphoramidite monomers and linker S122a-e (FIG. 17) for oligonucleotide synthesis. These and similar embodiments can be used to synthesize RNAs with a 2'-OCH$_3$ group or oligonucleotides that contain one or more nucleosides with a 2'-OCH$_3$ group including those that contain one or more sensitive groups. S122a-e can be prepared from known 2'-OMe nucleosides [L Chanteloup et al 1994 *Tetrahedron Lett* 35:877 doi:10.1016/50040-4039(00)75987-9] using similar procedures for the preparation of S077a-d FIG. 7) and S041 FIG. 3) by individuals having ordinary skill in the art in organic synthesis.

Some embodiments of the invention use the phosphoramidite monomers S123a-d (FIG. 18) for oligonucleotide synthesis. These and similar embodiments can be used to synthesize oligonucleotides that contain one or more nucleosides with a 2'-F atom including those that contain one or more sensitive groups. S123a-d can be prepared from known 2'-F nucleosides [A M Kawasaki et al 1993 *J Med Chem* 36:831 doi:10.1021/jm00059a007] using similar procedures for the preparation of S077a-d FIG. 7) and S041 FIG. 3) except that a modification is needed for the introduction of the MeDmoc group to the amino group of cytosine during the synthesis of S123a. In this case, the procedure involving using two equivalents LDA should not be used. Instead, the procedure involving using DMAP as catalyst under milder conditions should be used [X Lin et al2016 *Org Lett* 18:3870 doi:10.1021/acs.orglett.6b01878].

Some embodiments of the invention can be applied to solution phase oligonucleotide synthesis. Some embodiments can be applied to liquid phase oligonucleotide synthesis. Some embodiments can be applied to fluorous affinity-assisted oligonucleotide synthesis.

Some embodiments of the invention can be used to synthesize phosphorothioates. The same procedure for the synthesis of oligonucleotide with phosphate diester internucleotide linkages can be used except that in the oxidation step, a sulfurizing agent instead of an oxidizing agent is used. This is easy to do by individuals having ordinary skill in the art of organic synthesis.

Some embodiments of the invention involve the use of a reagent that can introduce a hydrophobic tag to the 5'-end of oligonucleotides to assist RP HPLC purification of the oligonucleotides. Four of the tagging agents for the purpose (S124a-d) are shown in FIG. 19. It is noted that during oligonucleotide deprotection and cleavage, when sodium periodate solution is used to oxidize the dithioketal or sulfide functions in the sulfur-based protecting groups and linkers, the conditions can be slightly acidic, which is beneficial for the oxidation reaction and is helpful to keep the oligonucleotide on the support to assist removal of excess sodium periodate and its reduced products. The DMTr group at the 5'-end of oligonucleotides, which are typically kept for RP HPLC purification, cannot survive the slightly acidic conditions. Therefore, tagging agents including, but not limited to, S124a-d that contain a more stable trityl group have to be used.

Some embodiments of the invention use a capping agent to cap the failure sequences generated in each synthesis cycle during oligonucleotide synthesis. Acetic anhydride, which is mostly used, and other similar capping agents gave unsatisfactory results. The reason is cap-exchange, in which a small percentage of amino protecting groups are replaced by the capping agent. In typical oligonucleotide synthesis, cap-exchange is acceptable because changing one acyl group to another is fine. They will all be removed during deprotection and cleavage, which uses harsh conditions. However, cap-exchange can cause serious problems in some embodiments of this invention because once the sulfur-based protecting groups are replaced with an acetyl group or similar groups, they cannot be removed under the mild conditions used for deprotection and cleavage. Therefore, special tagging agents should be used. Six examples of suitable capping agents are shown in FIG. 20. The phosphoramidite-based capping agents including, but not limited to, S125a-c have little or no cap-exchange problems. The sulfur-based oxidatively removable capping agents including, but not limited to, S125d-f will exchange with the amino protecting groups, but they can be removed during oligonucleotide deprotection and cleavage under the mild conditions needed for sensitive oligonucleotide synthesis.

In some embodiments, oligonucleotides are synthesized on a support. Details for selected embodiments are provided in the Experimental Examples section. In general, a support with a sulfur-based linker cleavable under non-nucleophilic and non-basic conditions including, but not limited to, S041, S103, S107e, S108e, S111e, S117e, S121e, and S122e can be used. The oligonucleotide is constructed on the support by stepwise addition of phosphoramidite monomers using a synthesis cycle comprising four steps—detritylation, coupling, capping and oxidation under typical oligonucleotides synthesis conditions or with modifications including, but not limited to, using capping agents such as S125a-f. Phosphoramidite monomers that contain one or more sensitive groups can be introduced into the oligonucleotide. In the last synthesis cycle, optionally, a hydrophobic tag including, but not limited to, S124a-e useful to assist RP HPLC purification of product can be introduced.

After oligonucleotide synthesis, the support, which carries the oligonucleotide product, is treated with reagents to deprotect the phosphate, exo-amino and if applicable 2'-hydroxyl protecting groups, and to cleave the product from the support.

In some embodiments comprising the use of linkers and Dmoc-CE-phosphoramidite monomers such as S041 and S047a-c, the support is first treated with a base such as DBU to remove the 2-cyanoethyl phosphate protecting group. Then, the dithioketal or sulfide functional groups in the protecting groups are oxidized with an oxidizing agent such as sodium periodate, and finally, a weak and nearly non-nucleophilic base such as aniline is introduced to initiate beta-elimination. An example deprotection and cleavage scheme is provided in FIG. 21. The fully deprotected and cleaved oligonucleotide can then be purified with RP HPLC. In cases of oligonucleotides with a hydrophobic tag, the tag is removed with an acid, and the product can be further purified with HPLC.

In some embodiments comprising the use of linkers and dM-Dmoc-CE-phosphoramidite monomers such as S041 and S060a-c, the procedure for deprotection and cleavage is the same as described for the cases where Dmoc-CE-phosphoramidite monomers are used except that the weak and nearly non-nucleophilic base aniline can be replaced with the weak and completely non-nucleophilic base potassium carbonate. An example is provided in FIG. 22.

In some embodiments comprising the use of linkers and Dmoc-Dim-phosphoramidite monomers such as S041 and S074a-d, the procedure for deprotection and cleavage is the same as described for the cases where Dmoc-CE-phosphoramidite monomers are used except that the treatment with DBU is not needed because the 2-cyanoethyl protecting groups are replaced with the Dim groups. An example deprotection and cleavage scheme is provided in FIG. 23.

In some embodiments comprising the use of linkers and MeDmoc-MeDim-phosphoramidite monomers such as S041, S077a-d, and S107a-e, the procedure for deprotection and cleavage is the same as described above for the cases where Dmoc-CE-phosphoramidite monomers are used except that the treatment with DBU is not needed because the 2-cyanoethyl protecting groups are replaced with the Dim groups, and the weak and nearly non-nucleophilic base aniline can be replaced with the weak and completely non-nucleophilic base potassium carbonate. Examples of deprotection and cleavage procedure are provided in FIG. 24.

In some embodiments comprising the use of linkers and phosphoramidite monomers such as S108a-e and S111a-e, the procedure for deprotection and cleavage comprises similar manipulations described for the cases where MeDmoc-MeDim-phosphoramidites are used (FIG. 24).

In some embodiments comprising the use of linkers and MeDmoc-MeDim-Tom-phosphoramidite monomers such as S117a-e, the procedure for deprotection and cleavage is similar as described for the cases where MeDmoc-MeDim-phosphoramidite monomers are used except that a treatment with a reagent such as triethylamine trihydrofluoride is needed to deprotect the 2'-Tom or 2'-TBDS groups. Conditions for the deprotection of 2'-Tom or 2'-TBDS groups are well-known in the art of RNA synthesis.

The oligonucleotides synthesized can be characterized with HPLC, MS, capillary electrophoresis, gel electrophoresis, oligonucleotide sequencing techniques and other means.

Research on oligonucleotide synthesis started half a century ago [K E Lundin et al 2015 *Hum Gene Ther* 26:475 doi:10.1089/hum.2015.070]. Searching suitable protecting groups for the synthesis has always been a central theme. This is particularly important for the synthesis of oligonucleotides that contain sensitive groups. Many protecting groups have been investigated [G Meher et al 2017 oligonucleotide therapies: the past and the present, In *current protocols in nucleic acid chemistry* doi:10.1002/cpnc.32]. However limited success has been achieved in the context of sensitive oligonucleotide synthesis. Potential reasons for the absence of prior art to use the sulfur-based protecting groups disclosed in this invention for oligonucleotide synthesis may come from several aspects. Unlike the allyl, silyl, acyl and many other protecting groups, the sulfur-based protecting groups are not well-studied and not widely utilized [S Shahsavari et al 2018 Beilstein *J Org Chem* 14:1750 doi: 10.3762/bjoc.14.149, S Shahsavari et al 2018 *Tetrahedron Lett* 59:1763 doi:10.1016/j.tetlet.2018.03.076]. Therefore, it is not as obvious as other groups to be tested for oligonucleotide synthesis. There were several reports on the use of sulfur-based protecting groups for peptide synthesis [H Kunz et al 1983 *Angew Chem Int Ed* 22:62 doi:10.1002/anie.198300621, H Kunz 1976 *Chemische Berichte* 109: 3693 doi:10.1002/cber.19761091123]. However, the reported methods have not found practical applications. The reasons include the difficulty of deprotection, and the lack of compatibility of the oxidative conditions needed to remove the sulfur-based groups with several amino acids. For oligonucleotide synthesis, even if the idea of using the sulfur-based group is conceived, the potential risk is intimidating. The groups rely on oxidation for deprotection, and there are many such groups on a single oligonucleotide molecule that need to be removed simultaneously. Therefore, a strong oxidation agent has to be used. However, oligonucleotides themselves are also susceptible to oxidation [Z Molphy et al 2015 *Front Chem* 3:28 doi:10.3389/fchem.2015.00028, A M Fleming et al 2015 *Chem Res Toxicol* 28:1292 doi:10.1021/acs.chemrestox.5b00096, J Bai et al 2018 *Chem Res Toxicol* 31:1364 doi:10.1021/acs.chemrestox.8b00244], and any oxidizing agents that could oxidize oligonucleotides even with a minimal rate must be unacceptable. What makes the situation even more complicated is that during oligonucleotide synthesis, one of the steps in each of the many synthetic cycles is oxidation of a phosphite triester to a phosphate triester. At this stage, many of the sulfur-based protecting groups already on the oligonucleotide must not be oxidized. Otherwise, the protecting groups will fall off prematurely. This complex issue of selective oxidation, that is, oxidizing phosphate triesters repeatedly in each of the many synthetic cycles during oligonucleotides without oxidizing any of the many sulfur-based groups, and oxidizing many sulfur-based groups in a single oligonucleotide without oxidizing many nucleobases in the oligonucleotide, may be another reason for the lack of prior art to accomplish the task of sensitive oligonucleotide synthesis using the sulfur-based protecting groups disclosed in this invention. In addition, the perceived lack of complete stability of the dithioacetal function in some of the embodiments of the invention in the detritylation step during oligonucleotide synthesis may also contributed to the absence of prior art of using sulfur-based protecting group for oligonucleotide synthesis. Indeed, during the course of developing the sulfur-based oligonucleotide synthesis technology disclosed in this invention, many obstacles had to be overcome. In particular, the identification of the causes of broad oligonucleotide peaks and their overlap with peaks of unidentifiable impurities in RP HPLC profiles, which severely hindered the practical use of the technology, was highly challenging [X Lin et al 2016 *Org Lett* 18:3870 doi:10.1021/acs.orglett.6b01878]. Only after the discovery of the use of phosphoramidite (e.g. S125a-c) or sulfur-based compounds (e.g. 125d-f) as capping agents during oligonucleotide synthesis and the use of suitable hydrophobic tags (e.g. the Tr group) that are stable under the slightly acidic conditions in sodium periodate oxidation step during oligonucleotide deprotection and cleavage to overcome the challenge, did the sulfur-based groups become practically useful for oligonucleotide synthesis [S Shahsavari et al 2019 *Beilstein J Org Chem* 15:1116 doi:10.3762/bjoc.15.108, S Shahsavari et al 2019 *J Org Chem* 84:13374 doi:10.1021/acs.joc.9b01527].

EXPERIMENTAL EXAMPLES

Example 1: Synthesis of S046 FIG. 3

To a solution of S045 [X Lin et al 2016 *Org Lett* 18:3870 doi:10.1021/acs.orglett.6b01878] (1.47 g, 1.6 mmol) in THF (40 mL) at 0° C. was added TBAF (1.95 mL, 1.0 M in THF, 1.9 mmol) dropwise. The mixture was stirred for 8 h while warming to rt. The contents were poured into a separation funnel and partitioned between EtOAc (40 mL) and $H_2O$ (40 mL). The aqueous layer was extracted with EtOAc (30 mL×2). The combined organic layer was dried over anhydrous $Na_2SO_4$, filtered and concentrated. Flash column chromatography ($SiO_2$, 1:1 hexanes/EtOAc) gave S046 as a white foam (0.96 g, 75%): m.p. 90.6-92.3° C.; $R_f$=0.3 (1:3 hexanes/EtOAc); $^1H$ NMR (400 MHz, $CDCl_3$) δ 1.35 (s, 3H), 1.41-1.63 (m, 4H), 1.69-1.81 (m, 2H), 1.89-2.08 (m, 2H), 2.37-2.44 (m, 1H), 2.56-2.75 (m, 3H), 2.84-2.93 (m, 2H), 3.42-3.51 (m, 2H), 3.61-3.65 (m, 2H), 3.77 (s, 6H), 3.98 (d, J=8 Hz, 1H), 4.24 (s, 1H), 4.97-5.01 (m, 1H), 5.34 (d, J=4 Hz, 1H), 6.42 (t, J=4 Hz, 8 Hz), 6.82 (d, J=8 Hz, 4H), 7.20-7.34 (m, 8H), 7.34-7.37 (m, 1H), 7.58 (s, 1H), 8.78 (s, 1H); $^{13}C$ NMR (100 MHz, $CDCl_3$) δ 11.6, 14.2, 21.0, 21.6, 25.4, 28.4, 28.6, 31.6, 32.1, 38.0, 48.9, 55.2, 60.4, 62.4, 63.7, 78.7, 79.1, 83.7, 84.4, 87.2, 111.6, 113.3, 127.2, 128.0, 128.1, 130.1, 130.1, 135.1, 135.2, 135.3, 144.2, 150.3, 154.2, 158.8, 158.8, 163.5; HRMS (ESI) m/z calcd for $C_{41}H_{48}N_2NaO_{10}S_2$ $[M+Na]^+$ 815.2648, found 815.2636.

Example 2: Preparation of S041 FIG. 3

A mixture of S046 (0.10 g, 0.13 mmol), succinic anhydride (0.05 g, 0.50 mmol), and DMAP (0.03 g, 0.25 mmol) in anhydrous pyridine (3 mL) was stirred at rt. After 2 days, the contents were partitioned between EtOAc (5 mL) and $H_2O$ (5 mL). The organic layer was washed with sat. $NaHCO_3$ and brine, dried over anhydrous $Na_2SO_4$, filtered, and concentrated. The residue was dissolved in dry DMF (3 mL), and mixed with amino-lcaa-CPG (0.251 g, 0.027 mmol, 107 μmol/g, 497 Å, Prime Synthesis, Inc.) and DCC (0.027 mL, 1.0 M in $CH_2Cl_2$, 0.027 mmol). After standing at rt for 2 days, the supernatant was removed, and the CPG was washed with pyridine (3 mL×5). To the CPG was added a capping solution (0.1 M DMAP in pyridine/$Ac_2O$, 9:1, v/v; 5 mL), and the mixture was allowed to stand at rt for 2 days. The supernatant was removed and the CPG was washed with pyridine (3 mL×5), MeOH (3 mL×3), DMF (3 mL×3) and acetone (3 mL×5), and dried under vacuum.

Example 3: Synthesis of S047a FIG. 4

A round-bottom flask containing S052 (0.69 g, 1.0 mmol), which was prepared from S051 [X Lin et al 2016 *Org Lett* 18:3870 doi:10.1021/acs.orglett.6b01878], and a magnetic stirring bar was evacuated and then refilled with nitrogen. The evacuation and nitrogen-filling cycle was repeated for two more times. Dry $CH_2Cl_2$ (10 mL), 2-cyanoethyl-N,N,N,N-tetraisopropylphosphoramidite (0.33 g, 0.34 mL, 1.09 mmol), and a solution of 1H-tetrazole in $CH_3CN$ (0.45 M, 2.41 mL, 1.09 mmol) were added via syringes sequentially. After stirring at rt for 2 h, the mixture was concentrated to dryness by a nitrogen flow over its surface. The residue was purified with flash column chromatography ($SiO_2$, 1:1 hexanes/EtOAc) giving S047a as a white foam (800 mg, 89%): $R_f$=0.32 (1:3 hexanes/EtOAc); $^1H$ NMR (400 MHz $CDCl_3$) δ 1.14 (d, J=6 Hz, 12H), 1.90-2.07 (m, 1H), 2.24-2.30 (m, 1H), 2.41 (t, J=8 Hz, 2H), 2.64-2.71 (m, 4H), 2.88-2.93 (m, 2H), 3.35-3.57 (m, 6H), 3.77 (s, 6H), 4.17-4.18 (m, 1H), 4.45-4.64 (m, 4H), 6.22 (t, J=6 Hz, 1H), 6.81-6.88 (m, 5H), 7.22-7.38 (m, 9H), 8.27 (d, J=8 Hz, 1H); $^{13}C$ NMR (100 MHz, $CDCl_3$) δ 20.1, 24.6, 27.2, 29.9, 40.8, 42.7, 43.3, 55.2, 58.1, 58.3, 61.9, 65.6, 71.6, 85.6, 86.8, 94.5, 113.2, 117.3, 127.0, 127.9, 128.2, 129.6, 130.0, 130.1, 135.2, 135.3, 144.0, 144.3, 158.6, 162.0; $^{31}P$ NMR (162 MHz, $CDCl_3$) δ 150.4; HRMS (ESI) m/z calcd for $C_{45}H_{56}N_5O_9PS_2H$ $[M+H]^+$ 906.3336, found 906.3342.

Example 4: Synthesis of S047b FIG. 4

The procedure for the synthesis of S047a was used with S054 [X Lin et al 2016 *Org Lett* 18:3870 doi:10.1021/acs.orglett.6b01878] as the starting material: White foam; yield 88%; $R_f$=0.4 (1:1:1 hexanes/EtOAc/$Et_3N$); $^1H$ NMR (400 MHz, $CDCl_3$) δ 1.17 (d, J=6 Hz, 12H), 1.94-2.07 (m, 1H), 2.41 (t, J=8 Hz, 2H), 2.52-2.99 (m, 7H), 3.32-3.41 (m, 2H), 3.55-3.72 (m, 4H), 3.76 (s, 6H), 4.13 (t, J=8 Hz, 1H), 4.28-4.31 (m, 1H), 4.56 (d, J=8 Hz, 2H), 4.74-4.79 (m, 1H), 6.45 (t, J=6 Hz, 1H), 6.77 (d, J=8 Hz, 4H), 7.16-7.37 (m, 9H), 8.16 (s, 1H), 8.68 (s, 1H); $^{13}$C NMR (100 MHz, CDCl$_3$) δ 20.4, 20.5, 24.7, 24.8, 25.7, 39.7, 43.2, 43.4, 55.4, 63.5, 65.6, 73.6, 73.8, 85.0, 86.2, 86.3, 86.7, 113.3, 117.6, 122.7, 127.1, 128.0, 128.4, 130.3, 135.8, 135.8, 141.7, 144.7, 149.5, 150.8, 151.1, 152.9, 158.7; $^{31}$P NMR (162 MHz, CDCl$_3$) 5150.0; HRMS (ESI) m/z calcd for C$_{46}$H$_{56}$N$_7$O$_8$PS$_2$H [M+H]$^+$ 930.3448, found 930.3441.

Example 5: Synthesis of S047c FIG. 4

The procedure for the synthesis of S047a was used with S059 [X Lin et al 2016 Org Lett 18:3870 doi:10.1021/acs.orglett.6b01878] as the starting material: White foam; yield 77%; R$_f$=0.5 (29:1 EtOAc/MeOH); $^1$H NMR (400 MHz, CDCl$_3$) δ 1.12-1.15 (m, 12H), 1.97-2.03 (m, 2H), 2.32-2.95 (m, 8H, H-2), 3.33 (d, J=4 Hz, 2H), 3.51-3.63 (m, 4H), 3.73 (s, 6H), 3.96 (t, J=10 Hz, 1H), 4.24-4.47 (m, 1H), 4.50 (d, J=8 Hz, 2H), 4.68-4.74 (m, 1H), 6.19 (t, J=6 Hz, 1H), 6.73-6.76 (m, 4H), 7.13-7.38 (m, 9H), 7.74 (s, 1H); $^{13}$C NMR (100 MHz, CDCl$_3$) δ 20.2, 20.3, 24.5, 24.5, 24.6, 26.8, 39.4, 42.1, 43.2, 43.3, 55.2, 57.8, 58.0, 63.7, 65.6, 73.7, 73.8, 84.6, 86.0, 86.3, 113.1, 117.3, 121.7, 126.9, 127.8, 128.0, 130.0, 135.7, 137.5, 144.5, 146.2, 148.0, 153.0, 158.5; $^{31}$P NMR (162 MHz, CDCl$_3$) δ 149.4; HRMS (ESI) m/z calcd for C$_{46}$H$_{56}$N$_7$O$_9$PS$_2$H [M+H]$^+$ 946.3397, found 946.3405.

Example 6: Synthesis of S061 FIG. 5

To a solution of 1,3-dithiane (5.0 g, 41.6 mmol, 1 equiv.) in dry THF (100 mL) was slowly added n-BuLi (2.5 M in pentane, 15.7 mL, 41.6 mmol, 1 equiv.) at −78° C. under argon from a Schlenk line. The mixture was stirred for 30 min at the same temperature. Freshly distilled acetone (3.0 mL, 41.6 mmol, 1 equiv.) was added. After stirring at −78° C. for 30 min, the reaction was quenched with sat. NH$_4$Cl (75 mL) and extracted with EtOAc (50 mL×2). The extracts were dried over anhydrous Na$_2$SO$_4$, filtered, and concentrated. The residue was purified with flash column chromatography (silica gel, 4:1 hexanes/EtOAc) to afford alcohol S061 [S Shahsavari et al 2018 Tetrahedron Lett 59:1763 doi:10.1016/j.tetlet.2018.03.076] as a white amorphous solid: 6.24 g, 84% yield; TLC R$_f$=0.3 (4:1 hexanes/EtOAc); $^1$H NMR (400 MHz, CDCl$_3$) δ 1.32 (s, 6H), 1.73-1.85 (m, 1H), 2.00-2.07 (m, 1H), 2.41 (s, 1H), 2.78-2.90 (m, 4H), 4.10 (s, 1H); $^{13}$C NMR (100 MHz, CDCl$_3$) δ 25.9, 27.4, 30.9, 61.0, 73.4; HRMS (ESI) m/z calcd for C$_7$H$_{14}$OS$_2$K [M+K]$^+$ 217.0123, found 217.0121.

Example 7: Synthesis of S062 FIG. 5

To a solution of S061 (6.4 g, 36 mmol, 1 equiv.) and pyridine (2.9 mL, 54 mmol, 1.5 equiv.) in DCM (100 mL) was added p-nitrophenylchloroformate (7.2 g, 36 mmol, 1 equiv.) at rt under argon. After stirring for 8 h, the contents were poured into a separatory funnel and partitioned between EtOAc (40 mL) and H$_2$O (80 mL). The aqueous layer was extracted with DCM (50 mL×2). The combined organic layer was dried over anhydrous Na$_2$SO$_4$, filtered and concentrated. Flash column chromatography (SiO$_2$, 9:1 hexanes/EtOAc) gave S062 [S Shahsavari et al 2018 Beilstein J Org Chem 14:1750 doi:10.3762/bjoc.14.149] as a white amorphous solid (10.0 g, 81%): TLC R$_f$=0.4 (5:1 hexanes/EtOAc); IR (thin film) v3083, 2981, 1713, 1592, 1522 cm$^{-1}$; $^1$H NMR (400 MHz, CDCl$_3$) δ 1.70 (s, 6H), 1.81-1.91 (m, 1H), 2.11-2.18 (m, 1H), 2.92-2.95 (m, 4H), 4.98 (s, 1H), 7.38 (d, J=9.2 Hz, 2H), 8.26 (d, J=6.9 Hz, 2H); $^{13}$C NMR (100 MHz, CDCl$_3$) δ 24.1, 25.7, 30.8, 56.2, 86.9, 121.9, 125.1, 145.2, 150.0, 155.5; HRMS (ESI) m/z calcd for C$_{14}$H$_{18}$O$_2$S$_2$K [M+K]$^+$ 21.0385, found 321.0404.

Example 8: Synthesis of S064 FIG. 5

To a solution of diisopropyl amine (1.2 mL, 8.5 mmol) in THF at −78° C. was added n-BuLi (2.5 M in pentane, 3.2 mL, 8.1 mmol) and stirred for 30 min. The freshly prepared LDA solution was added via a cannula to a solution of S063 (1.9 g, 4.05 mmol) in THF (50 mL) at −78° C. After stirring for 30 min, S062 was added as a solid under positive nitrogen pressure at −78° C. The mixture was stirred for 8 h while warming to rt. The contents were poured into a separatory funnel and partitioned between EtOAc (40 mL) and H$_2$O (40 mL). The aqueous layer was extracted with EtOAc (30 mL×2). The combined organic layer was dried over anhydrous Na$_2$SO$_4$, filtered and concentrated. Flash column chromatography (SiO$_2$, 1:1 hexanes/EtOAc) gave S064 [S Shahsavari et al 2019 Beilstein J Org Chem 15:1116 doi:10.3762/bjoc.15.108] as a white foam (2.33 g, 86%): R$_f$=0.6 (1:2 hexanes/EtOAc); $^1$H NMR (400 MHz, CDCl$_3$): δ 0.89-1.02 (m, 28H), 1.57 (s, 6H), 1.71-1.78 (m, 1H), 2.00-2.04 (m, 1H), 2.23-2.28 (m, 1H), 2.46-2.53 (m, 1H), 2.76-2.86 (m, 4H), 3.73 (d, J=8.5 Hz, 1H), 3.93-3.97 (m, 1H), 4.09-4.12 (m, 1H), 4.27-4.33 (m, 1H), 4.92 (s, 1H), 5.98 (d, J=6.5 Hz, 1H), 7.05 (d, J=7.4 Hz, 1H), 8.10 (d, J=7.4 Hz, 1H); $^{13}$C NMR (100 MHz, CDCl$_3$): δ 12.5, 13.12, 13.16, 13.6, 16.9, 17.10, 17.12, 17.2, 17.5, 17.64, 17.67, 24.7, 25.9, 31.0, 39.9, 56.8, 60.0, 66.7, 85.2, 85.3, 85.7, 94.5, 143.9, 150.8, 154.9, 162.6; HRMS (ESI): m/z calcd for C$_{29}$H$_{52}$N$_3$O$_7$S$_2$Si$_2$ [M+H]$^+$ 674.2785, found 674.2783.

Example 9: Synthesis of S065 FIG. 5

To the THF (10 mL) solution of S064 (800 mg, 1.19 mmol) at rt was added TBAF (1 M in THF, 3.0 mL, 3.0 mmol). The mixture was stirred for 1 h. THF was evaporated and the residue was loaded directly on a column. Flash column chromatography (SiO$_2$, 9.5:0.5 EtOAc/MeOH) gave S065 [S Shahsavari et al 2019 Beilstein J Org Chem 15:1116 doi:10.3762/bjoc.15.108] as a white foam (0.507 g, 99%): R$_f$=0.3 (9.5:0.5 EtOAc/MeOH); $^1$H NMR (400 MHz, CD$_3$OD): δ 1.60 (s, 6H), 1.70-1.77 (m, 1H), 2.04-2.10 (m, 1H), 2.12-2.18 (m, 1H), 2.43-2.49 (m, 1H), 2.82-2.94 (m, 4H), 3.71 (dd, J=12.1, 3.8 Hz, 1H), 3.81 (dd, J=12.1, 3.2 Hz, 1H), 3.96-3.99 (m, 1H), 4.33-4.37 (m, 1H), 4.81 (s, 2H), 5.07 (s, 1H), 6.19 (t, J=6.2 Hz, 1H), 7.22 (d, J=7.5 Hz, 1H), 8.40 (d, J=7.5 Hz, 1H); 130 NMR (100 MHz, CD$_3$OD): δ 24.0, 26.0, 30.7, 41.3, 56.8, 61.3, 70.4, 84.5, 87.3, 88.2, 95.5, 144.4, 151.6, 156.4, 163.5; HRMS (ESI): m/z calcd for C$_{17}$H$_{24}$N$_3$O$_6$S$_2$[M−H]$^-$ 430.1107, found 430.1112.

Example 10: Synthesis of S066 FIG. 5

To a solution of S065 (513 mg, 1.19 mmol) in pyridine (10 mL) at 0° C. was added DMTrCl (440 mg, 1.31 mmol) under positive nitrogen pressure. The mixture was stirred for 8 h while warming to rt. The volume of the mixture was reduced to about 2 mL under vacuum from an oil pump (small amount of pyridine was intentionally left to ensure basicity of the residue, which could help to avoid losing DMTr from product). The residue was partitioned between 5 Na$_2$CO$_3$ (30 mL) and EtOAc (30 mL). The aqueous layer was extracted with EtOAc (15 mL×2). The combined organic layer was dried over anhydrous $Na_2SO_4$, filtered and concentrated to dryness. Flash column chromatography ($SiO_2$, 9.5:0.5:0.5 EtOAc/MeOH/$Et_3N$) gave S066 [S Shahsavari et al 2019 *Beilstein J Org Chem* 15:1116 doi:10.3762/bjoc.15.108] as a white foam (523 mg, 60%): $R_f$=0.5 (9.5:0.5:0.5 EtOAc/MeOH/$Et_3N$); $^1$H NMR (400 MHz, $CDCl_3$): δ 1.57 (s, 6H), 1.68-1.79 (m, 1H), 1.99-2.03 (m, 1H), 2.14-2.21 (m, 1H), 2.67-2.73 (m, 2H), 2.80-2.83 (m, 4H), 3.31-3.34 (m, 1H), 3.41-3.44 (m, 1H), 3.73 (s, 6H), 4.15 (d, J=3.3 Hz, 1H), 4.49 (d, J=4.3 Hz, 1H), 4.93 (s, 1H), 6.2 (t, J=5.2 Hz, 1H), 6.79 (d, J=8.3 Hz, 4H), 6.90 (d, J=7.3 Hz, 1H), 7.16 (t, J=7.0 Hz, 1H), 7.25 (d, J=8.6 Hz, 4H), 7.36 (d, J=7.6 Hz, 2H), 8.03 (bs, 1H), 8.23 (d, J=7.4 Hz); $^{13}$C NMR (100 MHz, $CDCl_3$): δ 24.8, 26.0, 31.1, 42.3, 55.4, 56.9, 62.9, 70.6, 85.1, 86.7, 86.9, 87.4, 95.2, 113.5, 127.2, 128.2, 128.4, 130.1, 130.2, 135.7, 135.9, 144.4, 150.9, 155.6, 158.7, 162.6; HRMS (ESI): m/z calcd for $C_{38}H_{44}N_3O_8S_2$ $[M+H]^+$ 734.2569, found 734.2565.

Example 11: Synthesis of S060a FIG. 5

To a solution of S066 (500 mg, 0.682 mmol) and diisopropylammonium tetrazolide (175 mg, 1.02 mmol) in DCM (10 mL) at rt was added 2-cyanoethyl N,N,N',N'-tetraisopropylphosphorodiamidite (325 μL, 1.02 mmol). After stirring at rt for 2 h, the reaction mixture was concentrated and loaded directly on a column. Flash column chromatography ($SiO_2$, 4:1:0.25 EtOAc/hexanes/$Et_3N$) gave S060a [S Shahsavari et al 2019 *Beilstein J Org Chem* 15:1116 doi:10.3762/bjoc.15.108] as a white foam (580 mg, 91%): Mixture of two diastereoisomers; $R_f$=0.3 and 0.4 (EtOAc); $^1$H NMR (400 MHz, $CDCl_3$): δ 1.03 (d, J=6.7 Hz, 2H), 1.11-1.20 (m, 12H), 1.23-1.30 (m, 3H), 1.61 (s, 6H), 2.02-2.08 (m, 1H), 1.73-1.83 (m, 1H), 2.02-2.08 (m, 1H), 2.18-2.29 (m, 2H), 2.40 (t, J=6.4 Hz, 1H), 2.57 (t, J=6.4 Hz, 1H), 2.65-2.75 (m, 2H), 2.81-2.89 (m, 4H), 3.29-3.36 (m, 1H), 3.45-3.60 (m, 5H), 3.78 (d, J=3.5 Hz, 1H), 4.14-4.18 (m, 1H), 4.53-4.62 (m, 1H), 4.92 (s, 1H), 6.20-6.26 (m, 1H), 6.82 (t, J=7.9 Hz, 5H), 7.26 (t, J=7.7 Hz, 6H), 7.37 (t, J=7.2 Hz, 2H), 8.17 (d, J=8.0 Hz, 1H), 8.26 (d, J=7.7 Hz, 1H); $^{13}$C NMR (100 MHz, $CDCl_3$): δ 20.3, 24.7, 26.0, 31.0, 41.0, 41.4, 43.4, 55.4, 56.8, 58.5, 62.1, 62.5, 85.2, 85.7, 87.0, 94.8, 113.4, 117.7, 128.1, 128.4, 128.5, 130.21, 130.26, 130.3, 135.6, 144.2, 150.8, 155.0, 158.8, 162.4; $^{31}$P NMR (162 MHz, $CDCl_3$): δ 149.7, 150.4; HRMS (ESI): m/z calcd for $C_{47}H_{61}N_5O_9PS_2$ $[M+H]^+$ 934.3648, found 934.3652.

Example 12: Synthesis of S060b FIG. 5

Synthesized using a similar procedure for the synthesis of S060a from S070 [S Shahsavari et al 2019 *Beilstein J Org Chem* 15:1116 doi:10.3762/bjoc.15.108]. After flash column chromatography ($SiO_2$, 2:1:0.15 EtOAc/hexanes/$Et_3N$), S060b was afforded as a white foam in 77% yield: Mixture of two diastereoisomers; $R_f$=0.3 and 0.4 (2:1 EtOAc/hexanes); $^1$H NMR (400 MHz, $CDCl_3$): δ 1.15-1.23 (m, 12H), 1.63 (s, 6H), 1.74-1.80 (m, 1H), 2.02-2.07 (m, 1H), 2.42 (t, J=6.4 Hz, 1H), 2.57 (t, J=6.4 Hz, 1H), 2.79-2.91 (m, 4H), 3.28-3.33 (m, 1H), 3.38-3.44 (m, 2H), 3.54-3.60 (m, 2H), 3.75 (s, 6H), 3.79-3.87 (m, 1H), 4.08-4.14 (m, 1H), 4.24-4.29 (m, 1H), 4.71-4.77 (m, 1H), 5.14 (s, 1H), 6.40-6.45 (m, 1H), 6.72-6.75 (m, 4H), 7.14-7.25 (m, 7H), 7.33-7.35 (m, 2H), 8.11 (d, J=9.5 Hz, 1H), 8.38 (bs, 1H), 8.65 (s, 1H); $^{13}$C NMR (100 MHz, $CDCl_3$): δ 20.1, 20.7, 22.5, 23.4, 24.8, 25.0, 26.2, 31.3, 39.7, 45.3, 45.5, 45.8, 55.4, 57.0, 58.5, 58.7, 63.6, 73.6, 74.4, 84.7, 84.7, 84.9, 86.0, 86.2, 86.7, 113.2, 117.6, 122.4, 127.0, 127.9, 128.2, 130.1, 135.7, 141.3, 144.5, 149.2, 149.7, 150.8, 152.8, 158.6; $^{31}$P NMR (162 MHz, $CDCl_3$): δ 149.7, 149.9; HRMS (ESI): m/z calcd for $C_{48}H_{60}N_7O_8PS_2H$ $[M+H]^+$ 958.3760, found 958.3769.

Example 13: Synthesis of S071 FIG. 5

S056 was converted to S071 following the procedure for the synthesis of S064 [S Shahsavari et al 2019 *Beilstein J Org Chem* 15:1116 doi:10.3762/bjoc.15.108]. After flash column chromatography ($SiO_2$, 1:1 EtOAc/hexanes) S071 was afforded as a brown foam in 55% yield: $R_f$=0.3 (1:1 EtOAc/hexanes); $^1$H NMR (400 MHz, $CDCl_3$): δ 0.96-1.08 (m, 28H), 1.63 (s, 6H), 1.77-1.85 (m, 1H), 2.08-2.15 (m, 1H), 2.52-2.55 (m, 2H), 2.85-2.92 (m, 4H), 3.81-3.85 (m, 1H), 3.94-4.04 (m, 2H), 4.71 (q, J=7.4 Hz, 1H), 4.96 (s, 1H), 6.08 (t, J=5.2 Hz, 1H), 7.82 (s, 1H); $^{13}$C NMR (100 MHz, $CDCl_3$): δ 12.8, 13.3, 13.4, 13.7, 17.20, 17.28, 17.3, 17.45, 17.47, 17.5, 17.6, 17.7, 17.8, 24.9, 26.0, 31.4, 40.3, 57.0, 62.0, 70.2, 82.8, 85.4, 86.9, 121.5, 136.7, 146.7, 147.3, 151.8, 155.6; HRMS (ESI): m/z calcd for $C_{30}H_{52}N_5O_7S_2Si_2$ $[M+H]^+$ 714.2847, found 714.2842.

Example 14: Synthesis of S072 FIG. 5

Synthesized using a similar procedure for the synthesis of S065 from S071 [S Shahsavari et al 2019 *Beilstein J Org Chem* 15:1116 doi:10.3762/bjoc.15.108]. After flash column chromatography ($SiO_2$, 4:1 EtOAc/MeOH) S072 was afforded as a brown foam in 80% yield: $R_f$=0.2 (9:1 EtOAc/MeOH); $^1$H NMR (400 MHz, $CD_3OD$): δ 1.79 (s, 6H), 1.70-1.79 (m, 1H), 2.00-2.10 (m, 1H), 2.39-2.44 (m, 1H), 2.60-2.70 (m, 1H), 2.85-2.92 (m, 4H), 3.22 (s, 1H), 3.70-3.76 (m, 2H), 3.92-4.05 (m, 2H), 4.50-4.54 (m, 1H), 5.16 (s, 1H), 8.20 (s, 1H); $^{13}$C NMR (100 MHz, $CD_3OD$): δ 23.6, 30.6, 40.4, 56.7, 61.8, 71.1, 84.3, 85.8, 88.0, 119.6, 138.2, 148.0, 153.7, 156.3; HRMS (ESI): m/z calcd for $O_{18}H_{26}N_5O_6S_2$ $[M+H]^+$ 472.1324, found 472.1326.

Example 15: Synthesis of S073 FIG. 5

Synthesized using a similar procedure for the synthesis of S066 from S072 [S Shahsavari et al 2019 *Beilstein J Org Chem* 15:1116 doi:10.3762/bjoc.15.108]. After flash column chromatography ($SiO_2$, 9:0.5:0.5 EtOAc/MeOH/$Et_3N$), S073 was afforded as a brown foam in 63% yield: $R_f$=0.4 (9.5:0.5 EtOAc/MeOH); $^1$H NMR (400 MHz, $CDCl_3$): δ 1.58 (s, 6H), 1.68-1.77 (m, 1H), 1.97-2.03 (m, 1H), 2.50-2.60 (m, 2H), 2.77-2.85 (m, 4H), 3.25-3.29 (m, 2H), 3.67 (s, 6H), 4.14-4.22 (m, 1H), 4.69-4.76 (m, 1H), 4.93 (s, 1H), 6.23 (t, J=6.2 Hz, 1H), 6.69 (d, J=8.7 Hz, 4H), 7.07-7.13 (m, 2H), 7.21 (d, J=8.6 Hz, 4H), 7.31 (d, J=7.3 Hz, 2H), 7.75 (s, 1H); $^{13}$C NMR (100 MHz, $CDCl_3$): δ 24.7, 25.9, 31.1, 40.6, 55.3, 60.6, 64.4, 72.0, 84.6, 86.5, 86.7, 113.2, 120.8, 127.9, 128.3, 130.1, 135.9, 137.7, 144.7, 147.1, 148.6, 152.7, 155.9, 158.6; HRMS (ESI): m/z calcd for $C_{39}H_{44}N_5O_8S_2$ $[M+H]^+$ 774.2631, found 774.2629.

Example 16: Synthesis of S060c FIG. 5

Synthesized using a similar procedure for the synthesis of S060a from S073 [S Shahsavari et al 2019 *Beilstein J Org Chem* 15:1116 doi:10.3762/bjoc.15.108]. After flash column chromatography ($SiO_2$, 9.5:0.5 EtOAc/$Et_3N$) S060c was afforded as a brown foam in 76% yield: Mixture of two diastereoisomers; $R_f$=0.4 and 0.5 (EtOAc); $^1$HNMR (400 MHz, $CDCl_3$): δ 1.08-1.25 (m, 12H), 1.59 (d, J=7.9 Hz, 6H), 1.74-1.85 (m, 1H), 2.06-2.14 (m, 1H), 2.37-2.47 (m, 2H), 2.68-2.74 (m, 1H), 2.83-2.91 (m, 4H), 3.26-3.32 (m, 2H), 3.49-3.60 (m, 2H), 3.74 (s, 6H), 4.08-4.16 (m, 1H), 4.20-4.27 (s, 1H), 4.62-4.71 (m, 1H), 4.97 (s, 1H), 6.11-6.19 (m, 1H), 6.75 (d, J=8.4 Hz, 4H), 7.15-7.28 (m, 7H), 7.36-7.38 (m, 2H), 7.72 (s, 1H); $^{13}$C NMR (100 MHz, CDCl$_3$): δ 20.2, 20.6, 23.10, 23.18, 24.7, 24.8, 26.0, 31.2, 39.7, 43.3, 43.5, 45.5, 55.4, 56.8, 58.3, 63.9, 74.7, 84.9, 86.5, 86.6, 113.3, 117.6, 121.6, 127.1, 128.0, 130.1, 135.8, 137.2, 137.5, 144.6, 144.7, 148.3, 152.1, 155.7, 158.7; $^{31}$P NMR (162 MHz, CDCl$_3$) δ 149.5, 149.7; HRMS (ESI): m/z calcd for C$_{48}$H$_{61}$N$_7$O$_9$PS$_2$ [M+H]$^+$ 974.3709, found 774.3715.

Example 17: Synthesis of S074a FIG. 6

To a solution of S049 (1.57 g, 10.48 mmol, 1.5 eq.) and freshly distilled diisopropyl amine (9.85 mL, 69.9 mmol, 10 eq.) in dry toluene (25 mL) was added bis(diisopropylamino)chlorophosphine (2.80 g, 10.48 mmol, 1.5 eq.) at rt under argon. After stirring overnight, the intermediate S075 in the supernatant was transferred into a solution of S052 (3.80 g, 6.99 mmol, 1 eq.) and diisopropylammonium tetrazolide (1.80 g, 10.48 mmol, 1.5 eq.) in dry DCM (50 mL) via a cannula with its inflow end wrapped with a copper wire-secured filter paper. The reaction mixture was stirred overnight, and then concentrated to dryness. The residue was dissolved in a mixture of solvents (1:1 hexanes/EtOAc with 5% Et$_3$N) and loaded directly on a column for flash column chromatography (SiO$_2$, 1:1 hexanes/EtOAc with 5% Et$_3$N). S074a was obtained as a white foam (5.04 g, 88%): Mixture of two diastereoisomers; R$_f$=0.2 and 0.3 (SiO$_2$, 1:1 hexanes/EtOAc); $^1$H NMR (400 MHz, CDCl$_3$) δ 1.04-1.16 (m, 12H), 1.38 (s, 3H), 1.77-1.87 (m, 1H), 1.96-2.07 (m, 1H), 2.28-2.42 (m, 1H), 2.45-2.58 (m, 1H), 2.60-2.69 (m, 2H), 2.65-2.84 (m, 4H), 3.29-3.46 (m, 2H), 3.47-3.69 (m, 2H), 3.76 (s, 6H), 3.80-3.89 (m, 1H), 4.04-4.23 (m, 1H), 4.74-4.77 (m, 1H), 6.38 (t, J=5.8 Hz, 1H), 6.81 (dd, J=8.8, 3.2 Hz, 4H), 7.20-7.29 (m, 7H), 7.40 (d, J=7.6 Hz, 2H), 7.60 (s, 0.5H), 7.63 (s, 0.5H), 8.84 (brs, 1H); $^{13}$C NMR (100 MHz, CDCl$_3$) δ 12.1, 24.81, 24.88, 24.95, 25.0, 26.1, 26.2, 28.8 (d, J$_{cp}$=9.2 Hz), 29.0 (d, J$_{cp}$=17.2 Hz), 40.5 (d, J$_{cp}$=5.4 Hz), 40.6 (d, J$_{cp}$=1.8 Hz), 43.4 (d, J$_{cp}$=3.4 Hz), 43.5 (d, J$_{cp}$=3.4 Hz), 47.1 (d, J$_{cp}$=7.0 Hz), 47.8 (d, J$_{cp}$=6.8 Hz), 55.5, 63.3, 63.7, 64.8 (d, J$_{cp}$=18.2 Hz), 65.0 (d, J$_{cp}$=18.9 Hz), 73.6 (d, J$_{cp}$=15.6 Hz), 74.1 (d, J$_{cp}$=15.2 Hz), 84.8, 85.0, 85.4 (d, J$_{cp}$=6.7 Hz), 86.0 (d, J$_{cp}$=2.8 Hz), 87.0, 87.1, 111.2, 113.4, 127.2, 128.1, 128.4, 130.4, 135.5, 135.6, 135.7, 136.0, 136.1, 144.5, 144.6, 150.4, 158.8, 164.0; $^{31}$P NMR (162 MHz, CDCl$_3$) δ 149.4, 149.6 ppm; HRMS (ESI) m/z calcd for C$_{42}$H$_{55}$N$_3$O$_8$PS$_2$ [M+H]$^+$ 824.3168, found 824.3170.

Example 18: Synthesis of S074b FIG. 6

Synthesized using a similar procedure for the synthesis of S074a from S054. Flash column chromatography (SiO$_2$, 1:1 hexanes/EtOAc with 5% Et$_3$N) gave S074b as a white foam (1.25 g, 52%): Mixture of two diastereoisomers; R$_f$=0.2 and 0.3 (SiO$_2$, 1:2 hexanes/EtOAc); $^1$H NMR (400 MHz, CDCl$_3$) δ 1.04-1.26 (m, 12H), 1.72-1.84 (m, 2H), 1.90-2.09 (m, 4H), 2.30-2.47 (m, 2H), 2.59-2.74 (m, 6H), 2.85-2.93 (m, 2H), 3.39-3.60 (m, 4H), 3.61-3.89 (m, 1H), 3.77 (s, 6H), 3.91-4.16 (m, 2H), 4.17-4.22 (m, 1H), 4.40-4.49 (m, 1H), 6.18-6.22 (m, 1H), 6.81 (d, J=7.4 Hz, 4H), 7.18-7.29 (m, 7H), 7.7.39 (d, J=7.6 Hz, 2H), 8.27-8.29 (m, 0.5H), 8.34-8.35 (m, 0.5H); $^{13}$C NMR (100 MHz, CDCl$_3$) δ 23.3 (d, J$_{cp}$=2.2 Hz), 23.4 (d, J$_{cp}$=1.6 Hz), 24.85, 24.92, 24.98, 25.1, 25.7, 25.9, 26.1, 26.2, 27.5, 27.6, 28.7 (d, J$_{cp}$=13.0 Hz), 29.1 (d, J$_{cp}$=21.5 Hz), 41.2 (d, J$_{cp}$=5.7 Hz), 41.5, 43.1, 43.4, 43.5, 45.4, 45.5, 47.1 (d, J$_{cp}$=6.9 Hz), 47.7 (d, J$_{cp}$=8.3 Hz), 55.5, 61.9, 62.4, 64.7 (d, J$_{cp}$=19.9 Hz), 64.8 (d, J$_{cp}$=18.5 Hz), 65.8, 65.9, 71.4 (d, J$_{cp}$=9.3 Hz), 71.9 (d, J$_{cp}$=10.1 Hz), 85.2 (d, J$_{cp}$=7.3 Hz), 86.1, 87.0, 94.5, 113.4, 127.2, 128.1, 128.4, 130.2, 130.3, 135.5, 135.6, 135.7, 135.8, 144.3, 144.4, 144.9, 145.0, 151.9, 155.0, 158.7, 161.9, 162.0; $^{31}$P NMR (162 MHz, CDCl$_3$) δ 149.2, 149.5; HRMS (ESI) m/z calcd for C$_{47}$H$_{62}$N$_4$O$_9$PS$_4$ [M+H]$^+$ 985.3137, found 985.3130.

Example 19: Synthesis of S074c FIG. 6

Synthesized using a similar procedure for the synthesis of S074a from S059. Flash column chromatography (SiO$_2$, 1:1 hexanes/EtOAc with 5% Et$_3$N) gave S074c as a white foam (1.30 g, 68%): Mixture of two diastereoisomers; R$_f$=0.3 and 0.4 (SiO$_2$, 1:2 hexanes/EtOAc); $^1$H NMR (400 MHz, CDCl$_3$) δ 1.09-1.25 (m, 12H), 1.75-1.84 (m, 2H), 1.95-2.04 (m, 4H), 2.59-2.75 (m, 6H), 2.87-2.98 (m, 4H), 3.31-4.00 (m, 4H), 3.75 (s, 6H), 4.00 (t, J=6.5 Hz, 0.5H), 4.05-4.18 (m, 1.5H), 4.21-4.27 (m, 0.5H), 4.30-4.39 (m, 0.5H), 4.55 (d, J=7.1 Hz, 2H), 4.80-4.88 (m, 1H), 6.46 (t, J=6.5 Hz, 1H), 6.74-6.77 (m, 4H), 7.14-7.30 (m, 7H), 7.36 (d, J=11.9 Hz, 2H), 8.16 (s, 0.5H), 8.19 (s, 0.5H), 8.68 (s, 1H); $^{13}$C NMR (100 MHz, CDCl$_3$) δ 23.27 (d, J$_{cp}$=2.6 Hz), 23.33 (d, J$_{cp}$=2.0 Hz), 24.86, 24.92, 24.99, 25.8, 26.1, 27.6, 28.8 (d, J$_{cp}$=11.5 Hz), 29.1 (d, J$_{cp}$=14.5 Hz), 40.1 (d, J$_{cp}$=14.8 Hz), 43.3, 43.4, 43.5, 45.45, 45.51, 47.2 (d, J$_{cp}$=7.5 Hz), 47.7 (d, J$_{cp}$=7.6 Hz), 55.5, 63.4, 63.7, 64.7 (d, J$_{cp}$=13.8 Hz), 65.4 (d, J$_{cp}$=18.5 Hz), 65.6, 73.9 (d, J$_{cp}$=13.7 Hz), 74.0 (d, J$_{cp}$=15.3 Hz), 84.8, 85.1, 85.9, 86.4, 86.6, 86.7, 113.3, 122.6, 127.0, 128.0, 128.3, 130.2, 135.78, 135.85, 141.6, 141.7, 144.67, 144.72, 149.2, 150.5, 151.06, 151.12, 152.8, 158.6; $^{31}$P NMR (162 MHz, CDCl$_3$) δ 149.4, 149.6; HRMS (ESI) m/z calcd for C$_{48}$H$_{62}$N$_6$O$_8$PS$_4$[M+H]$^+$ 1009.3249, found 1009.3255.

Example 20: Synthesis of S074d FIG. 6

Synthesized using a similar procedure for the synthesis of S074a from S076. Flash column chromatography (SiO$_2$, 8:1:1 EtOAc/ACN/Et$_3$N) gave S074d as a white foam (1.30 g, 68%): Mixture of two diastereoisomers; R$_f$=0.2 and 0.3 (SiO$_2$, 8:1:1 EtOAc/ACN/Et$_3$N). $^1$H NMR (400 MHz, CDCl$_3$) δ 1.07-1.16 (m, 12H), 1.77-1.86 (m, 2H), 1.97-2.08 (m, 4H), 2.59-2.94 (m, 10H), 3.25-3.31 (m, 2H), 3.52-3.58 (m, 2H), 3.75 (s, 6H), 3.58-4.21 (m, 2.5H), 4.29-4.32 (m, 0.5H), 4.50 (d, J=3.5 Hz, 1H), 4.52 (d, J=3.4 Hz, 1H), 4.72-4.81 (m, 1H), 6.18-6.23 (m, 1H), 6.72-6.78 (m, 4H), 7.16-7.30 (m, 7H), 7.37 (d, J=7.0 Hz, 1H), 7.39 (d, J=7.8 Hz, 1H), 7.8 (s, 0.5H), 7.82 (s, 0.5H); $^{13}$C NMR (100 MHz, CDCl$_3$) δ 24.86, 24.91, 24.94, 24.98, 25.6, 26.1, 27.1, 28.88 (d, J$_{cp}$=11.1 Hz), 29.16 (d, J$_{cp}$=8.5 Hz), 39.9, 42.5, 43.4, 43.5, 47.2 (d, J$_{cp}$=6.9 Hz), 47.6 (d, J$_{cp}$=7.4 Hz), 55.5, 63.6, 63.9, 64.8 (d, J$_{cp}$=6.6 Hz), 65.0 (d, J$_{cp}$=6.5 Hz), 66.0, 73.9 (d, J$_{cp}$=11.1 Hz), 74.1 (d, J$_{cp}$=16.5 Hz), 84.3, 84.4, 85.7 (d, J$_{cp}$=6.6 Hz), 86.2 (d, J$_{cp}$=2.9 Hz), 86.6, 113.3, 121.6, 127.0, 128.0, 128.3, 128.4, 130.18, 130.24, 135.8, 135.9, 137.4, 137.5, 144.6, 144.7, 146.3, 148.30, 148.32, 153.11, 153.13, 155.7, 158.6; $^{31}$P NMR (162 MHz, CDCl$_3$) δ 148.9, 149.6; HRMS (ESI) m/z calcd for C$_{48}$H$_{62}$N$_6$O$_9$PS$_4$ [M+H]$^+$ 1025.3198, found 1025.3205.

Example 21: Synthesis of S077a-d FIG. 7

These compounds were synthesized using a similar procedure for the synthesis of S074a.

Example 22: Synthesis of 5084-087a-d FIG. 8

These compounds were synthesized using a similar procedure for the synthesis of S074a.

Example 23: Synthesis of S088a FIG. 9

To the solution of S090 (100 mg, 0.21 mmol), which was prepared from S089 [X Lin et al 2016 Org Lett 18:3870 doi:10.1021/acs.orglett.6b01878], in $CH_2Cl_2$ (2 mL) was added diisopropylammonium tetrazolide (54 mg, 0.32 mmol) and 2-cyanoethyl N,N,N',N'-tetraisopropylphosphorodiamidite (97 mg, 0.32 mmol), and the reaction mixture was stirred under nitrogen at rt for 2 h. The mixture was loaded onto a column ($SiO_2$) and eluted with the solvent mixture EtOAc/hexanes/$Et_3N$ (20:20:1). S088a [X Lin et al 2016 Org Lett 18:3870 doi:10.1021/acs.orglett.6b01878] was obtained as a pale yellow oil (130 mg, 82%): two diastereoisomers, $R_f$=0.50 (20:20:1 EtOAc/hexanes/$Et_3N$); $^1$H NMR (400 MHz, $CDCl_3$) δ 1.01-1.31 (m, 12H, H-1), 1.45-4.68 (m, 4H, H-2), 2.04 (t, J=6.7 Hz, 1H, H-3), 2.11 (t, J=6.7 Hz, 1H, H-3), 2.29 (s, 3H, H-4), 2.44 (t, J=6.3 Hz, 1H, H-5), 2.62 (t, J=6.2 Hz, 1H, H-5), 2.82 (t, J=7.1 Hz, 1H, H-6), 2.83 (t, J=7.1 Hz, 1H, H-6), 3.05-3.10 (m, 0.5H, H-7), 3.15-3.24 (m, 1H, H-7), 3.28-3.36 (m, 0.5H, H-7), 3.41-3.69 (m, 4H, H-7), 3.69-3.80 (m, 1H, H-8), 3.75 (s, 3H, H-9), 3.76 (s, 3H, H-9), 3.81-3.91 (m, 1H, H-8), 3.95-4.08 (m, 1H, H-10), 5.76 (t, J=5.6 Hz, 0.5H, NH), 6.05 (t, J=5.2 Hz, 0.5H, NH), 6.79 (d, J=7.6 Hz, 2H, H-11), 6.81 (d, J=5.6 Hz, 2H, H-11), 6.16-7.29 (m, 7H, H-12), 7.41-7.43 (m, 2H, H-12); $^{31}$P NMR (162 MHz, $CDCl_3$) δ 149.9, 150.3; HRMS (ESI) m/z calcd for $C_{40}H_{54}N_3O_7PSNa$ [M+Na]$^+$ 774.3318, found 774.3316.

Example 24: Synthesis of S088b FIG. 9

Synthesized using a similar procedure for the synthesis of S088a from S092 [S Shahsavari et al 2019 Beilstein J Org Chem 15:1116 doi:10.3762/bjoc.15.108]. After flash column chromatography ($SiO_2$, 2:1:0.15 hexanes/EtOAc/$Et_3N$) S088b was afforded as a colorless oil in 99% yield: Mixture of diastereoisomers; $R_f$=0.6 and 0.7 (1:1 hexanes/EtOAc); $^1$H NMR (400 MHz, $CDCl_3$): δ 1.05 (d, J=6.7 Hz, 4H), 1.14-1.26 (m, 22H), 1.54-1.63 (m, 2H), 2.24-2.29 (m, 2H), 2.35-2.39 (m, 1H), 2.59 (t, J=6.5 Hz, 2H), 2.92-2.99 (m, 1H), 3.09-3.18 (m, 2H), 3.50-3.65 (m, 3H), 3.76 (s, 6H), 3.91-3.99 (m, 1H), 4.11 (q, J=7.1 Hz, 2H), 6.80 (t, J=8.7 Hz, 4H), 7.15-7.20 (m, 2H), 7.23-7.27 (m, 2H), 7.32 (d, J=8.9 Hz, 4H), 7.45 (d, J=7.0 Hz, 2H); $^{13}$C NMR (100 MHz, $CDCl_3$): δ 14.4, 20.3, 20.6, 24.6, 24.7, 24.8, 24.9, 25.0, 25.2, 25.3, 29.3, 29.41, 29.44, 29.5, 29.7, 29.8, 33.6, 33.8, 34.5, 43.1, 43.3, 43.4, 55.3, 58.3, 58.6, 60.3, 66.2, 66.5, 73.6, 73.7, 74.4, 74.6, 86.0, 86.1, 117.9, 126.81, 126.87, 127.8, 128.4, 128.5, 130.2, 130.32, 130.36, 136.5, 145.3, 158.6, 174.0 ppm. $^{31}$P NMR (162 MHz, $CDCl_3$): δ149.1, 149.7; HRMS (ESI): m/z calcd for $C_{43}H_{61}N_2O_7PNa$ [M+Na]' 771.4114, found 771.4108.

Example 25: Synthesis of S088c FIG. 9

Synthesized using a similar procedure for the synthesis of S088a from S094 [X Lin et al 2016 Org Lett 18:3870 doi:10.1021/acs.orglett.6b01878]: white foam; yield 78%; two diastereoisomers, $R_f$=0.4 and 0.5 (2:1 EtOAc/hexanes); $^1$H NMR (400 MHz, $CDCl_3$) δ 1.11-1.24 (m, 12H, H-1), 2.41 (t, J=6.5 Hz, 1H, H-2), 2.63 (t, J=6.3 Hz, 1H, H-2), 3.05-3.09 (m, 0.5H, H-3), 3.19-3.28 (m, 1H, H-3), 3.33-3.45 (m, 0.5H, H-3), 3.50-3.68 (m, 4H, H-3), 3.50-3.78 (m, 1H, H-5), 3.76 (s, 3H, H-4), 3.77 (s, 3H, H-4), 3.84-3.94 (m, 1H, H-5), 3.96-4.15 (m, 3H, H-6, H-7), 6.70-6.83 (m, 4H, H-8), 7.17-7.48 (m, 9H, H-9); $^{31}$P NMR (162 MHz, $CDCl_3$) δ 149.90, 149.94; HRMS (ESI) m/z calcd for $C_{35}H_{45}ClN_3O_6PH$ [M+H]$^+$ 670.2813, found 670.2809.

Example 26: Synthesis of S088d FIG. 9

Synthesized using a similar procedure for the synthesis of S088a from S097 [B Halami et al 2018 ChemistrySelect 3:8857 doi:10.1002/slct.201801484]. Flash chromatography ($SiO_2$, hexanes/EtOAc/$Et_3N$ 50:10:2 to 5:30:3) gave S088d as a white foam (695 mg, 88%): two diastereomers; TLC $R_f$=0.57, 0.53 (hexanes/EtOAc 4:3); $^1$H NMR (400 MHz, $CDCl_3$) δ 8.77 (s, 1H), 8.19 and 8.18 (s, 1H), 7.39-7.35 (m, 2H), 7.28-7.15 (m, 7H), 6.78-6.74 (m, 4H), 6.49-6.45 (m, 1H), 4.80-4.72 (m, 1H), 4.13 (q, J=7.1 Hz, 2H), 3.86-3.80 (m, 1H), 3.76-3.75 (m, 6H), 3.67-3.57 (m, 4H), 3.52 (t, J=7.5 Hz, 2H), 3.40-3.28 (m, 3H), 2.98-2.92 (m, 2H), 2.62 (t, J=6.3 Hz, 1H), 2.47 (t, J=6.4 Hz, 1H), 1.22-1.09 (m, 15H); $^{13}$C NMR (100 MHz, $CDCl_3$) δ 172.6, 160.5, 158.5, 152.2, 144.5, 142.4, 135.6, 135.6, 133.2, 130.1, 130.0, 130.0, 128.1, 128.1, 127.8, 126.9, 126.9, 113.1, 86.5, 84.6, 84.6, 86.5, 84.6, 84.6, 63.6, 63.4, 60.6, 55.3, 55.3, 43.5, 43.3, 39.5, 31.7, 28.0, 24.8, 24.7, 24.7, 24.7, 14.4; $^{31}$P NMR (162 MHz, $CDCl_3$) δ 150.2, 150.0 ppm; HRMS (ESI): calcd for $C_{45}H_{55}N_6O_8PH$ [M+H]$^+$ 839.38972 found 839.38853, and $C_{45}H_{55}N_6O_8PNa$ [M+Na]$^+$ 861.37162 found 861.36923.

Example 27: Synthesis of S088e FIG. 9

Synthesized using a similar procedure for the synthesis of S088a from S099e [B Halami et al 2018 ChemistrySelect 3:8857 doi:10.1002/slct.201801484]. Flash chromatography ($SiO_2$, hexanes/EtOAc/$Et_3N$ 50:10:2 to 50:40:4) gave S088e as a white foam (510 mg, 80%): two diastereomers; TLC $R_f$=0.45, 0.43 (hexanes/EtOAc 4:3); $^1$H NMR (400 MHz, $CDCl_3$) δ 8.76 (s, 1H), 8.17 (s, 1H), 7.37-7.34 (m, 2H), 7.29-7.14 (m, 7H), 6.77-6.74 (m, 4H), 6.49 (t, J=7.3 Hz, 1H), 4.71-4.76 (m, 1H), 4.31-4.27 (m, 1H), 4.23-4.19 (m, 2H), 3.88-3.78 (m, 2H), 3.75 (s, 6H), 3.57-3.49 (m, 5H), 3.36-3.30 (m, 4H), 3.02 (t, J=7.4 Hz, 2H), 2.93-2.87 (m, 1H), 2.75-2.71 (m, 1H), 2.61 (t, J=6.3 Hz, 2H), 2.46 (t, J=6.4 Hz, 1H), 1.28-1.22 (m, 3H), 1.18-1.14 (m, 6H), 1.11-1.09 (m, 3H); $^{13}$C NMR (100 MHz, $CDCl_3$) δ 172.6, 160.4, 158.5, 152.1, 150.2, 144.5, 142.4, 135.6, 135.6, 133.2, 130.0, 128.1, 128.1, 127.8, 126.9, 117.5, 113.1, 86.5, 85.9, 84.6, 70.5, 63.7, 63.6, 59.1, 58.5, 58.3, 55.3, 43.5, 43.3, 39.5, 31.5, 27.9, 24.8, 24.7, 24.6, 23.09, 20.58; $^{31}$P NMR (162 MHz, $CDCl_3$) δ 150.2, 150.1; HRMS (ESI): calcd for $C_{46}H_{57}N_6O_9PH$ [M+H]$^+$ 869.40029 found 869.40006, and $C_{46}H_{57}N_6O_9PNa$ [M+Na]$^+$ 891.382223 found 891.37988.

Example 28: Synthesis of S088f-h FIG. 9

These compounds were synthesized using a similar procedure for the synthesis of S088a [B Halami et al 2018 ChemistrySelect 3:8857 doi:10.1002/slct.201801484].

Example 29: Synthesis of S088i FIG. 9

To a suspension of lithium aluminum hydride (1.15 g, 30.29 mmol, 5 eq.) in dry THF (25 mL) was added a solution of S092 (3.15 g, 6.06 mmol, 1 eq.) in dry THF (50 mL) dropwise via cannula at 0° C. under nitrogen. The reaction mixture was stirred for 3 h, and then quenched by dropwise addition of $H_2O$ (1.15 mL), 15% NaOH (1.15 mL), and $H_2O$ (3.45 mL), sequentially. The white precipitate was removed by filtration over Celite. The filtrate was concentrated to dryness. Flash column chromatography ($SiO_2$, 1:1 hexanes/EtOAc with 5% $Et_3N$) gave the intermediate alcohol as a colorless oil (2.45 g, 80%): $R_f$=0.2 ($SiO_2$, 1:1 hexanes/EtOAc); $^1H$ NMR (400 MHz, $CDCl_3$) δ 1.20-1.42 (m, 14H), 1.53 (p, J=5.8 Hz, 2H), 1.65 (brs, 1H), 2.45 (brs, 1H), 3.02 (dd, J=9.3, 7.6 Hz, 1H), 3.16 (dd, J=9.6, 3.6 Hz, 1H), 3.59 (t, J=6.6 Hz, 2H), 3.73-3.75 (m, 1H), 3.76 (s, 6H), 6.82 (d, J=8.9 Hz, 4H), 7.20 (tt, J=7.4, 1.2 Hz, 1H), 7.28 (t, J=7.2 Hz, 2H), 7.32 (d, J=9.9 Hz, 2H), 7.43 (d, J=9.6 Hz, 2H); $^{13}C$ NMR (100 MHz, $CDCl_3$) 525.8, 26.1, 29.72, 29.78, 29.8, 29.9, 33.0, 33.7, 55.5, 63.2, 67.9, 71.2, 86.2, 113.3, 126.9, 127.9, 128.3, 130.2, 136.2, 145.0, 158.5; HRMS (ESI) m/z calcd for $C_{32}H_{43}O$ $[M+H]^+$ 507.3110, found 507.3122.

To the solution of the intermediate alcohol (2.06 g, 4.07 mmol, 1 eq.) in freshly distilled pyridine (50 mL) was added TsCl (0.814 g, 1.05 eq.) at 0° C. under nitrogen. The mixture was stirred at the same temperature for 8 h. The majority of pyridine was evaporated on a rotary evaporator under vacuum generated by an oil pump. The remaining content was poured into a separatory funnel containing 5% $NaHCO_3$ (100 mL) and extracted with EtOAc (50 mL×3). The extracts were dried over anhydrous $Na_2SO_4$, filtered, and concentrated. Flash column chromatography ($SiO_2$, 2:1 hexanes/EtOAc with 5% $Et_3N$) gave the intermediate tosylate as a pale-yellow oil (1.37 g, 51%): $R_f$=0.4 ($SiO_2$, 1:1 hexanes/EtOAc); $^1H$ NMR (400 MHz, $CDCl_3$) δ 1.12-1.41 (m, 14H), 1.61 (p, J=6.7 Hz, 2H), 2.42 (s, 3H), 3.01 (t, J=9.2 Hz, 1H), 3.16 (dd, J=9.4, 3.3 Hz, 1H), 3.70-3.74 (m, 1H), 3.76 (s, 6H), 4.00 (t, J=6.5 Hz, 2H), 6.81 (d, J=8.8 Hz, 4H), 7.20 (t, J=7.1 Hz, 1H), 7.26 (t, J=4.8 Hz, 2H), 7.31 (d, J=8.8 Hz, 6H), 7.43 (d, J=7.3 Hz, 2H), 7.77 (d, J=8.3 Hz, 2H); $^{13}C$ NMR (100 MHz, $CDCl_3$) δ 21.9, 25.6, 25.7, 29.1, 29.2, 29.60, 29.67, 29.8, 33.6, 55.5, 67.8, 70.9, 71.2, 86.2, 113.3, 126.9, 127.9, 128.3, 129.9, 130.2, 133.4, 136.2, 144.7, 145.0, 158.5; HRMS (ESI) m/z calcd for $C_{39}H_{49}O_7S$ $[M+H]^+$ 661.3199, found 661.3204.

To the solution of the intermediate tosylate (6.78 g, 10.28 mmol, 1 eq.) in dry DMSO (25 mL) was added KCN (0.802 g, 12.34 mmol, 1.2 eq.) at rt under nitrogen. The reaction mixture was stirred at 60° C. overnight. After cooling to rt, EtOAc (100 mL) was added, and the organic phase was washed with brine (100 ml), dried over anhydrous $Na_2SO_4$, filtered, and concentrated. Flash column chromatography ($SiO_2$, 4:1 hexanes/EtOAc with 5% $Et_3N$) gave the intermediate cyanate as a colorless oil (4.20 g, 79%): $R_f$=0.2 ($SiO_2$, 4:1 hexanes/EtOAc); $^1H$ NMR (400 MHz, $CDCl_3$) δ 1.22-1.26 (m, 10H), 1.37-1.42 (m, 4H), 1.61 (p, d=7.1 Hz, 2H), 2.27 (t, J=7.1 Hz, 2H), 2.41 (brs, 1H), 3.02 (dd, J=9.2, 7.5 Hz, 1H), 3.16 (dd, J=9.3, 3.3 Hz, 1H), 3.76 (s, 6H), 6.81 (d, J=8.9 Hz, 4H), 7.20 (t, J=7.4 Hz, 1H), 7.28 (t, J=7.8 Hz, 2H), 7.32 (d, J=8.5 Hz), 7.43 (d, J=8.2 Hz); $^{13}C$ NMR (100 MHz, $CDCl_3$) δ 17.4, 25.7, 25.8, 28.9, 29.0, 29.5, 29.7, 29.9, 33.7, 55.5, 67.9, 71.2, 86.3, 113.3, 120.0, 126.9, 127.95, 127.98, 128.3, 130.2, 136.3, 145.0, 158.6; HRMS (ESI) m/z calcd for $C_{33}H_{42}NO_4$ $[M+H]^+$ 516.3113, found 516.3120.

To a suspension of lithium aluminum hydride (1.55 g, 40.8 mmol, 5 eq.) in dry THF (50 mL) was added the solution of the intermediate cyanate (4.20 g, 8.16 mmol, 1 eq.) in dry THF (50 mL) dropwise via cannula at 0° C. under nitrogen. The mixture was stirred overnight while warming to rt gradually. The reaction was then quenched by dropwise addition of $H_2O$ (1.55 mL), 15% aq. NaOH (1.55 mL), and $H_2O$ (4.65 mL), sequentially. The white precipitate was removed by filtration over Celite and the filtrate was concentrated to dryness. Flash column chromatography ($SiO_2$, 8:1:1 EtOAc/MeOH/$Et_3N$) gave S101 as a pale-yellow oil (2.50 g, 60%): $R_f$=0.2 ($SiO_2$, 8:1:1 EtOAc/MeOH/$Et_3N$); $^1H$ NMR (400 MHz, $CDCl_3$) δ 1.15-1.49 (m, 18H), 2.11 (brs, 2H), 2.67 (t, J=7.1 Hz, 2H), 2.99 (dd, J=9.1, 7.7 Hz, 1H), 3.14 (dd, J=9.3, 3.1 Hz, 1H), 3.70-3.73 (m, 1H), 3.77 (s, 6H), 6.81 (d, J=8.8 Hz, 4H), 7.19 (t, J=6.6 Hz, 1H), 7.27 (t, J=7.2 Hz, 2H), 7.30 (d, J=8.6 Hz, 4H), 7.41 (d, J=7.4 Hz, 2H); $^{13}C$ NMR (100 MHz, $CDCl_3$) 525.8, 27.2, 29.7, 29.82 (2C), 29.88, 29.9, 33.7 (2C), 42.4, 55.5, 67.9, 71.2, 86.3, 113.3, 126.9, 128.0, 128.3, 130.2, 136.2, 145.0, 158.6; HRMS (ESI) m/z calcd for $C_{33}H_{46}NO_4$ $[M+H]^+$ 520.3426, found 520.3429.

To the solution of S101 (220 mg, 0.423 mmol, 1 eq.) and triethylamine (88 µL, 0.635 mmol, 1.5 eq.) in dry DCM (15 mL) was added 6-chlorohexanoyl chloride (0.051 mL, 0.423 mmol, 1 eq.) at −78° C. under nitrogen. The mixture was stirred for 1 h while warming to rt slowly. Water (15 mL) was added and the organic contents were extracted with DCM (15 mL×3). The extracts were combined and dried over anhydrous $Na_2SO_4$, filtered, and concentrated. Flash column chromatography ($SiO_2$, 2:1 hexanes/EtOAc with 5% $Et_3N$) gave the intermediate alkyl chloride as a pale-yellow oil (0.134 g, 49%): $R_f$=0.5 ($SiO_2$, 1:1 hexanes/EtOAc); $^1H$ NMR (400 MHz, $CDCl_3$) δ 1.19-1.51 (m, 20H), 1.64 (p, J=8.8 Hz, 2H), 1.75 (p, J=6.7 Hz, 2H), 2.14 (t, J=7.4 Hz, 2H), 2.35 (brs, 1H), 3.00 (dd, J=9.3, 7.6 Hz, 1H), 3.14 (dd, J=9.3, 3.3 Hz, 1H), 3.20 (q, J=7.1 Hz, 2H), 3.50 (t, J=6.6 Hz, 2H), 3.70-3.74 (m, 1H), 3.76 (s, 6H), 5.49 (brs, 1H), 6.80 (d, J=8.9 Hz, 4H), 7.19 (tt, J=7.2, 2.1 Hz, 1H), 7.26 (t, J=7.8 Hz, 2H), 7.30 (d, J=8.8 Hz, 4H), 7.41 (d, J=8.7 Hz, 2H); $^{13}C$ NMR (100 MHz, $CDCl_3$) δ 25.3, 25.8, 26.8, 27.2, 29.6, 29.77, 29.79 (2C), 29.89, 29.97, 32.6, 33.7, 36.9, 39.8, 45.1, 55.5, 67.9, 71.2, 86.3, 113.3, 126.9, 127.9, 128.3, 130.2, 136.3, 145.0, 158.6, 172.6; HRMS (ESI) m/z calcd for $C_{39}H_{55}ClNO_5$ $[M+H]^+$ 652.3768, found 652.3770.

S088i was synthesized using a similar procedure for the synthesis of S088a from the intermediate alkyl chloride. Flash column chromatography ($SiO_2$, 1:1 hexanes/EtOAc with 5% $Et_3N$) gave S088i as a pale-yellow oil (294 mg, 86%): Mixture of two diastereoisomers; $R_f$=0.2 and 0.3 ($SiO_2$, 1:1 hexanes/EtOAc); $^1H$ NMR (400 MHz, $CDCl_3$) δ 1.03 (d, J=6.8 Hz, 2H), 1.10-1.35 (m, 22H), 1.40-1.51 (m, 4H), 1.56-1.69 (m, 4H), 1.77 (p, J=7.1 Hz), 1.81-1.94 (m, 1H), 1.95-2.10 (m, 3H), 2.15 (t, J=7.4 Hz, 2H), 2.56-3.15 (m, 6H), 3.21 (t, J=6.8 Hz, 1H), 3.22 (t, J=6.5 Hz, 1H), 3.52 (t, J=6.6 Hz, 2H), 3.55-4.18 (m, 4H), 3.76 (s, 1H), 3.77 (s, 3H), 4.35-4.57 (m, 2H), 5.47 (brs, 1H), 6.78 (d, J=8.8 Hz, 2H), 6.80 (d, J=7.3 Hz, 2H), 7.13-7.21 (m, 1H), 7.21-7.28 (m, 2H), 7.32 (dd, J=6.5, 2.6 Hz, 2H), 7.34 (dd, J=8.4, 1.7 Hz, 2H), 7.44 (dd, J=5.4, 1.6 Hz, 1H), 7.46 (dd, J=7.2, 1.6 Hz); $^{13}C$ NMR (100 MHz, $CDCl_3$) δ 24.84, 24.86, 24.90, 24.94, 25.00, 25.07, 25.11, 25.17, 25.28, 25.38, 25.6, 25.9, 26.1, 26.30, 26.34, 26.7, 26.8, 27.0, 27.2, 27.3, 28.6, 28.7, 28.85, 28.88, 29.6, 29.81, 29.85, 29.88, 29.93, 29.99, 30.03, 32.6, 33.79 (d, $J_{cp}$=3.0 Hz), 33.86 (d, $J_{cp}$=5.2 Hz), 36.9, 39.8, 43.2, 43.4, 45.1, 46.93 (d, $J_{cp}$=7.1 Hz), 47.29 (d, $J_{cp}$=7.3 Hz), 55.5, 64.9 (d, $J_{cp}$=17.4 Hz), 66.3 (d, $J_{cp}$=6.8 Hz), 74.4, 85.9, 113.2, 126.7, 127.8, 128.45, 128.53, 130.3, 136.6, 136.7, 145.3, 145.4, 158.4, 172.6; $^{31}P$ NMR (162 MHz, $CDCl_3$) δ 149.0, 149.2; HRMS (ESI) m/z calcd for $C_{50}H_{77}ClN_2O_6PS_2$ $[M+H]^+$ 931.4649, found 931.4650.

Example 30: Synthesis of S088j FIG. 9

Synthesized using a similar procedure for the synthesis of S088a from S092. Flash column chromatography ($SiO_2$, 9:1 hexanes/EtOAc with 5% Et$_3$N) gave S088i as a colorless oil (412 mg, 79%): Mixture of two diastereoisomers; R$_f$=0.6 and 0.7 (SiO$_2$, 3:1 hexanes/EtOAc); $^1$H NMR (400 MHz, CDCl$_3$) δ 1.05 (d, J=6.8 Hz, 3H), 1.11-1.35 (m, 23H), 1.45-1.79 (m, 3H), 1.79-1.95 (m, 1H), 1.95-2.12 (m, 1H), 2.259 (t, J=7.7 Hz, 1H), 2.263 (t, J=7.5 Hz, 1H), 2.57-2.68 (m, 1H), 2.69-2.89 (m, 3H), 2.96 (q, J=2.9 Hz, 1H), 3.06 (q, J=5.8 Hz, 1H), 3.22 (q, J=5.2 Hz, 1H), 3.22 (q, J=5.0 Hz), 3.47-3.65 (m, 2H), 3.65-3.80 (m, 1H), 3.766 (s, 3H), 3.773 (s, 3H), 3.84-3.92 (m, 1H), 3.92-4.05 (m, 1H), 4.11 (q, J=7.1 Hz, 2H), 4.10-4.21 (m, 1H), 6.78 (d, J=11.7 Hz, 2H), 6.81 (d, J=7.5 Hz, 2H), 7.13-7.21 (m, 1H), 7.24 (t, J=7.9 Hz, 1H), 7.26 (t, J=7.2 Hz, 1H), 7.33 (d, J=8.6 Hz, 2H), 7.35 (dd, J=8.0, 1.6 Hz, 2H), 7.45 (d, J=5.1 Hz, 1H), 7.46 (d, J=5.2 Hz, 1H); $^{13}$C NMR (100 MHz, CDCl$_3$) δ 14.6, 24.84, 24.86, 24.91, 24.94, 25.00, 25.04, 25.07, 25.11, 25.17, 25.31, 25.34, 25.39, 26.30, 26.34, 28.6 (d, J$_{cp}$=7.0 Hz), 28.9 (d, J$_{cp}$=9.0 Hz), 29.47, 29.51, 29.59, 29.72, 29.76, 29.91, 30.02, 33.76, 33.9 (d, J$_{cp}$=6.3 Hz), 34.7, 43.2 (d, J$_{cp}$=4.2 Hz), 43.4 (d, J$_{cp}$=4.0 Hz), 46.9 (d, J$_{cp}$=5.5 Hz), 47.3 (d, J$_{cp}$=7.0 Hz), 55.5, 60.4, 64.9 (d, J$_{cp}$=7.4 Hz), 65.1 (d, J$_{cp}$=18.5 Hz), 66.3 (d, J$_{cp}$=1.8 Hz), 66.4 (d, J$_{cp}$=3.3 Hz), 73.7 (d, J$_{cp}$=15.0 Hz), 74.3 (d, J$_{cp}$=18.7 Hz), 85.9, 113.1, 126.7, 127.8, 128.45, 128.53, 130.30, 130.37, 136.6, 136.7, 145.3, 145.4, 158.4, 174.0; $^{31}$P NMR (162 MHz, CDCl$_3$) δ 149.0, 149.2; HRMS (ESI) m/z calcd for C$_{45}$H$_{67}$NO$_7$PS$_2$ [M+H]$^+$ 828.4096, found 828.4099.

Example 31: Synthesis of S124a FIG. 19

Synthesized using a similar procedure for the synthesis of S074a from 5'-O-(triphenylmethyl)-thymidine [JP Horwitz et al 1962 *J Org Chem* 27:3300 doi:10.1021/jo01056a502]. Flash column chromatography (SiO$_2$, 1:1 hexanes/EtOAc with 5% Et$_3$N) gave S124a as a white foam (233 mg, 87%): Mixture of two diastereoisomers; R$_f$=0.2 and 0.3 (SiO$_2$, 1:1 hexanes/EtOAc); $^1$H NMR (400 MHz, CDCl$_3$) δ 1.04-1.27 (m, 12H), 1.40 (s, 3H), 1.78-1.86 (m, 1H), 1.96-2.05 (m, 1H), 2.29-2.98 (m, 8H), 3.30-3.99 (m, 5H), 4.05-4.25 (m, 1H), 4.74-4.81 (m, 1H), 6.38 (t, J=7.1 Hz, 1H), 7.18-7.35 (m, 9H), 7.36-7.45 (m, 6H), 7.56 (s, 0.5H), 7.60 (s, 0.5H), 9.11 (brs, 1H); $^{13}$C NMR (100 MHz, CDCl$_3$) δ 12.1, 24.84, 24.88, 24.91, 24.95, 25.01, 26.1, 26.2, 28.8 (d, J$_{cp}$=8.4 Hz), 29.0 (d, J$_{cp}$=17.3 Hz), 40.4 (d, J$_{cp}$=5.1 Hz), 40.6, 43.4, 43.5, 47.0 (d, J$_{cp}$=7.2 Hz), 47.5 (d, J$_{cp}$=7.4 Hz), 63.5, 63.9, 64.8 (d, J$_{cp}$=17.9 Hz), 65.0 (d, J$_{cp}$=18.4 Hz), 73.6 (d, J$_{cp}$=15.3 Hz), 73.9 (d, J$_{cp}$=14.4 Hz), 84.8, 85.0, 85.3 (d, J$_{ap}$=6.7 Hz), 85.9, 87.55, 87.61, 111.1, 111.2, 127.5, 128.1, 128.9, 135.9, 136.0, 143.5, 143.6, 150.5, 164.1; $^{31}$P NMR (162 MHz, CDCl$_3$) δ 149.4, 149.7; HRMS (ESI) m/z calcd C$_{40}$H$_{51}$N$_3$O$_6$PS$_2$ [M+H]$^+$ 764.2956, found 764.2960.

Figure 21:
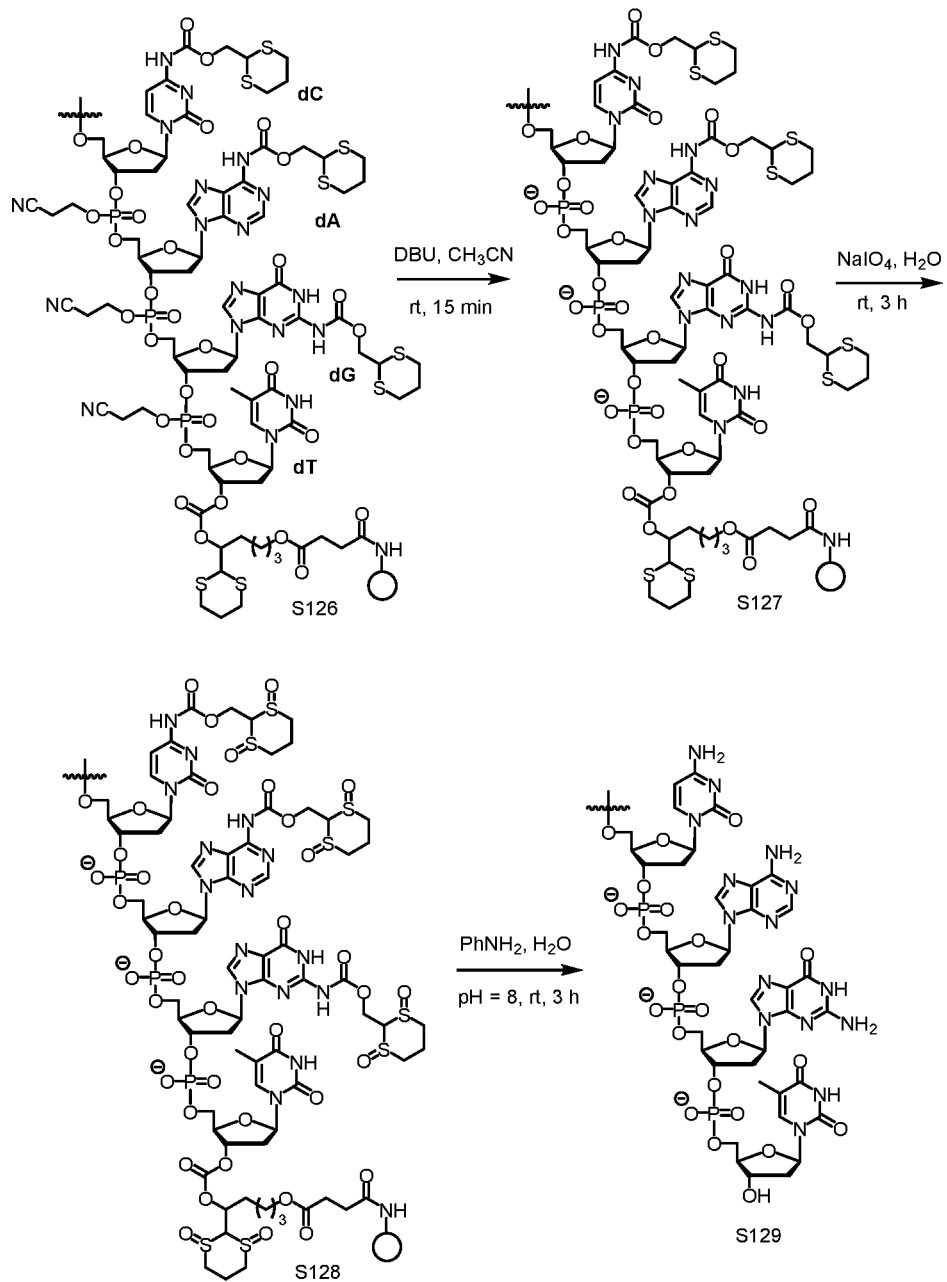
FIG. 21. Deprotection and cleavage of oligonucleotides assembled with Dmoc-CE-phosphoramidites.
Figure 25:
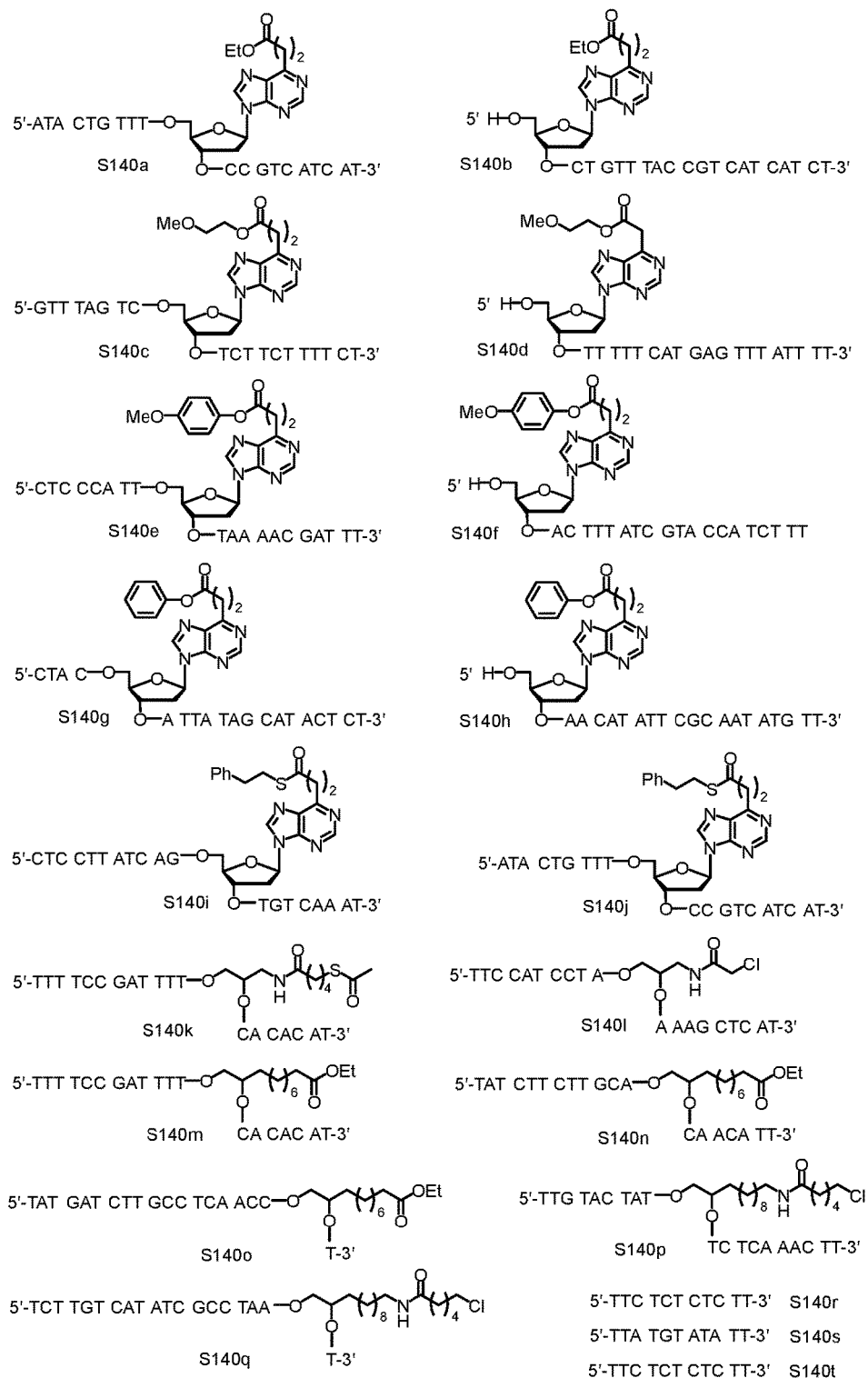
FIG. 25. Example oligonucleotide sequences including those containing sensitive groups that have been synthesized.

Example 32: Oligonucleotide Synthesis, Deprotection, Cleavage and Analysis—Procedure for the Embodiments Comprising the Use of Dmoc-CE-Phosphoramidites Such as 5047a-c Example oligonucleotides were synthesized on a MerMade 6 automated synthesizer. S041 with support being solid CPG (pore size 497 Å, loading 26 µmol/g, ~20 mg, ~0.52 µmop was used as the solid support. Detritylation: 2% DCA in DCM, 90 sec×2. Coupling: 0.1 M solutions of Dmoc-CE-phosphoramidites S047a-c, commercial 2-cyanoethyl 5'-DMTr-dT, and S088a-j in acetonitrile, 100 sec×3. Capping: cap A, 5% phenoxyacetic anhydride in THF/pyridine, cap B, 16% methylimidazole in THF, 50 sec. Oxidation: 0.02 M I$_2$ in THF/pyridine/H$_2$O, 60 sec. At the end of the synthesis, 5'-DMTr was removed. The procedure for deprotection and cleavage is shown in FIG. 21. To a portion of the CPG (represented by S126) in a 2 mL centrifuge tube was added DBU (10% in MeCN, 1.0 mL). The tube was gently shaken at rt for 15 min and then centrifuged at 2.5 k rpm for 30 sec. The supernatant was removed with a pipette. The CPG was washed with MeCN (200 µL×3). This converted the CPG represented by S126 to S127. To the CPG (S127) was added 0.4 M NaIO$_4$ (1.0 mL). After gently shaken at rt for 3 h, the tube was centrifuged, and supernatant was removed. The oxidation was repeated under the same conditions for 1 h. This converted the CPG represented by S127 to S128. The CPG (S128) was washed with H$_2$O (200 µL×3). Aniline solution (3%, 1.0 mL, in some cases, 0.5% 4-aminobenzyl alcohol was used) was added. After gently shaken at rt for 1 h, the tube was centrifuged, and the supernatant was transferred to another 2.0 mL centrifuge tube. This converted S128 to S129. The CPG was washed with H$_2$O (200 µL×2). The supernatant and the washes were combined, and the volume was reduced to ~50 µL in a centrifugal vacuum concentrator. To the tube was added 1-butanol (500 µL). The tube was vortexed (1 min) and centrifuged (14.5K rpm, 15 min). The supernatant was removed with a pipette carefully without sucking away the oligonucleotide precipitate. The oligonucleotide (S129) was dissolved in H$_2$O (20 µL) and injected into RP HPLC to generate the profile of crude oligonucleotide. The fraction of the peak corresponding to the oligonucleotide was collected, concentrated, dissolved in H$_2$O and re-injected into HPLC to generate the profile of pure oligonucleotide. The pure oligonucleotide was analyzed with MALDI-TOF MS. Using the procedure, example oligonucleotides S140a-j (FIG. 25) were synthesized. The crude and pure HPLC profiles, and MALDI-TOF MS of oligonucleotide S140a are provided in FIG. 26-28, respectively. Data for all the oligonucleotides can be found in reference [B Halami et al 2018 *Chemistry-Select* 3:8857 doi:10.1002/slct.201801484].

Figure 22:
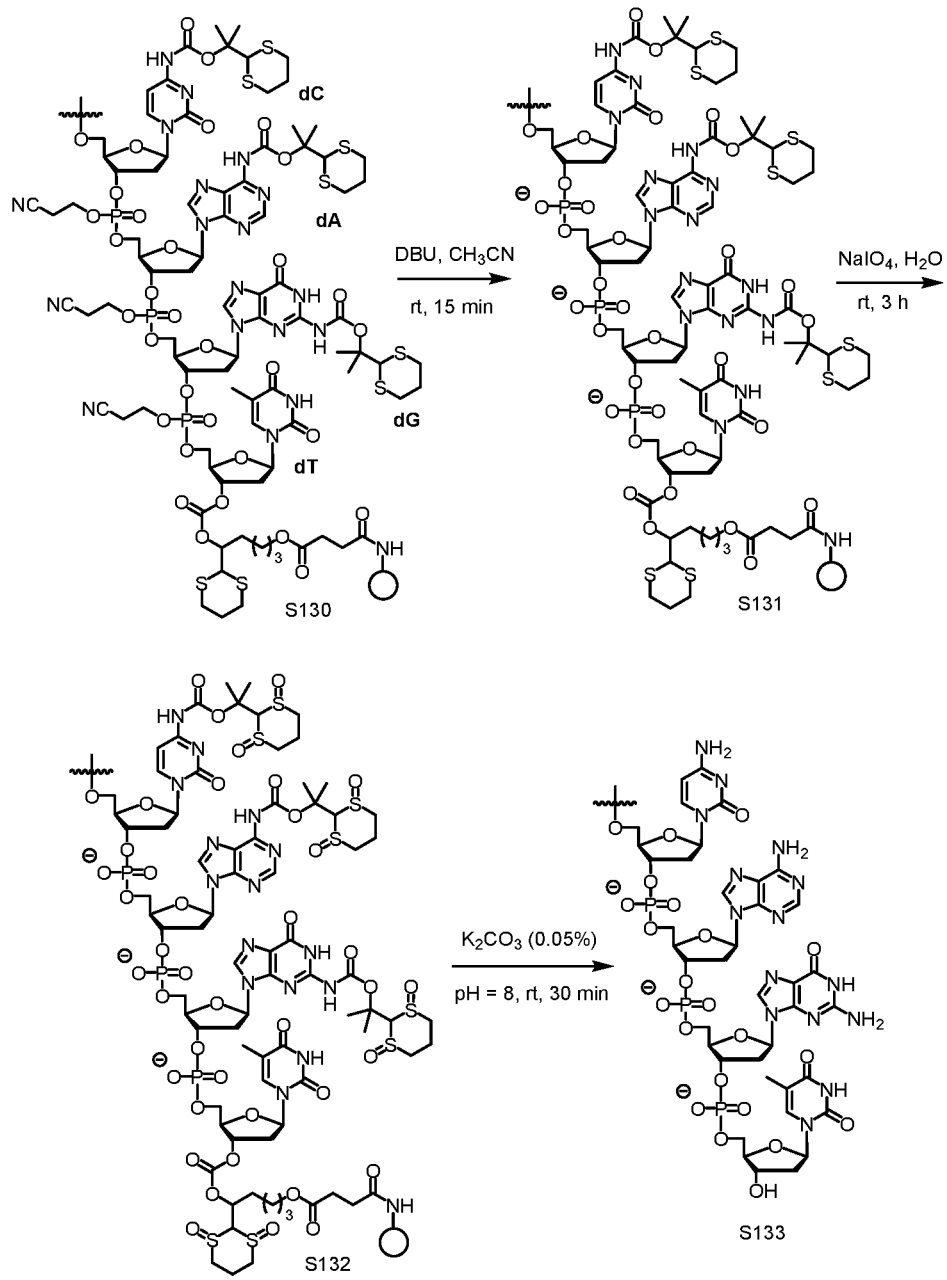
FIG. 22. Deprotection and cleavage of oligonucleotides assembled with dM-Dmoc-CE-phosphoramidites.

Example 33: Oligonucleotide Synthesis, Deprotection, Cleavage and Analysis—Procedure for the Embodiments Comprising the Use of dM-Dmoc-CE-Phosphoramidites Such as S060a-c Example oligonucleotides were synthesized on S041 with the support being CPG (26 µmol/g loading, 20 mg, 0.52 µmop using a MerMade 6 Synthesizer. dM-Dmoc-CE-phosphoramidites S060a-c and the commercial 5'-DMTr-CE dT phosphoramidite were used as monomers. The conditions suggested by synthesizer manufacturer for 1 µmol synthesis were used except that coupling was optionally increased from 2 to 3 times and capping was achieved using S125c instead of acetic anhydride. Briefly, detritylation: DCA (3%, DCM), 90 sec×2; coupling: phosphoramidite (0.1 M, MeCN), 5-(ethylthio)-1H-tetrazole (0.25 M, MeCN), 60 sec×3 (or 2); capping: S125c (0.1 M, MeCN) and 5-(ethylthio)-1H-tetrazole (0.25 M, MeCN), 60 sec×3; oxidation: I$_2$ (0.02 M, THF/pyridine/H$_2$O, 70/20/10, v/v/v), 40 sec. For incorporating the last nucleoside monomer, a 5'-trityl 2-cyanoethyl deoxynucleoside phosphoramidite (e.g. S124a) instead of the 5'-DMTr counterpart was used. At the end of synthesis, the 5'-trityl group was kept. The procedure for deprotection and cleavage is shown in FIG. 22. The CPG, represented by S130 was divided into 10 equal portions. One portion was gently shaken in a solution of DBU/CH$_3$CN (1:9, v/v, 1 mL) at rt for 15 min. The supernatant was removed with a pipette, and the CPG was washed with CH$_3$CN (1 mL×5). This removed the 2-cyanoethyl groups on the phosphate groups, and converted the CPG represented by S130 to S131. To the CPG (S131), aqueous NaIO$_4$ (0.4 M, 1 mL) was added and the mixture was shaken at rt for 3 h. The supernatant was removed with a pipette, and the CPG was rinsed briefly with water (1 mL×4). Alternatively, oxidation was achieved with 0.1 M NaIO$_4$ (1 mL, rt, 1 h x 3). The CPG was then washed with H$_2$O (1 mL×4). This oxidized the dithioketals in the dM-Dmoc and Dmoc groups, and converted the CPG represented by S131 to S132. HPLC analysis of the supernatant and washes indicated that the oligonucleotide was not cleaved from CPG at this time. To the CPG (S132) was added aqueous K$_2$CO$_3$ (0.05%, pH 8, 500 µL), and the mixture was shaken at rt for 30 min. The supernatant was transferred into a centrifugal tube. The process was repeated one time. This converted S132 to S133. The combined supernatant was concentrated to ~100 µL and injected into RP HPLC to generate crude oligonucleotide trace [In some trials, before HPLC the combined supernatant (1 mL) was loaded on a polyacrylamide desalting column (10 mL) and eluted with H$_2$O to remove the salts from the oligonucleotide]. Fractions of the major oligonucleotide peak at ~39 min were collected, concentrated to ~100 µL, and injected into HPLC to give the profile of purified trityl-tagged oligonucleotide. To the dried trityl-tagged oligonucleotide was added 1 mL of 80% AcOH, and the mixture was shaken gently at rt for 3 h. Volatiles were evaporated. The residue was dissolved in ~100 µL water, and injected into RP HPLC. The major peak of de-tritylated oligonucleotide at ~21 min was collected and concentrated to dryness. The residue was the pure de-tritylated oligonucleotide, which was dissolved in 100 µL water and injected into HPLC to generate the profile of pure de-tritylated oligonucleotide. The pure oligonucleotide was analyzed with MALDI-TOF MS. Using the procedure, example oligonucleotides S140k-m (FIG. 25) were synthesized. The crude trityl-on, pure trityl-on, crude trityl-off and pure trityl-off RP HPLC profiles, pure trityl-on and pure trityl-off MALDI-TOF MS of S140k are provided in FIG. 29-34, respectively. Data for all the oligonucleotides can be found in reference [S Shahsavari et al 2019 *Beilstein J Org Chem* 15:1116 doi:10.3762/bjoc.15.108].

Example 34: Oligonucleotide Synthesis, Deprotection, Cleavage and Analysis—Procedure for the Embodiments Comprising the Use of Dmoc-Dim-Phosphoramidites Such as S074a-d Example oligonucleotides were synthesized on S041 with the support being CPG (26 µmol/g loading, 20 mg, 0.52 µmol) using a MerMade 6 Synthesizer. Dmoc-Dim phosphoramidites were used as monomers. The conditions suggested by synthesizer manufacturer for 1 µmol synthesis were used except that coupling was optionally increased from 2 to 3 times and capping was achieved using S125a instead of acetic anhydride. Briefly, detritylation: DCA (3%, DCM), 90 sec×2; coupling: phosphoramidites S074a-d (0.1 M, MeCN), 5-(ethylthio)-1H-tetrazole (0.25 M, MeCN), 60 sec×2 (or 3); capping: S125a (0.1 M, MeCN) and 5-(ethylthio)-1H-tetrazole (0.25 M, MeCN), 60 sec×3; oxidation: I$_2$ (0.02 M, THF/pyridine/H$_2$O, 70/20/10, v/v/v), 40 sec. For incorporating the last nucleoside, 5'-Tr phosphoramidites such as S124b instead of 5'-DMTr phosphoramidites such as S074a-d was used. At the end of synthesis, the 5'-trityl group was kept on. The procedure for deprotection and cleavage is shown in FIG. 23. The CPG represented by S134 was divided into 5 equal portions. One portion was gently shaken in a solution of aqueous NaIO$_4$ (0.4 M, 1 mL) at rt for 3 h. The supernatant was removed with a pipette, and the CPG was rinsed briefly with water (1 mL×4). This converted the CPG represented by S134 to S135. To the CPG was added aqueous aniline solution (3%, 1 mL) and the mixture was shaken at rt for 3 h. The supernatant was transferred into a centrifugal tube, which was concentrated to ~100 µL. To the tube was added 1-butanol (900 µL). The tube was vortexed briefly and centrifuged (14.5 k rpm, 5 min). The supernatant was removed with a pipette carefully without sucking the oligonucleotide precipitate. This converted S135 to S136. The oligonucleotide was dissolved in H$_2$O (100 µL) and ~35 µL was injected into RP HPLC to generate the crude oligonucleotide. Fractions of the major oligonucleotide peak at ~39 min were collected, concentrated to ~100 µL, and injected into HPLC to give the profile of purified trityl-tagged oligonucleotide. To the dried trityl-tagged oligonucleotide was added 1 mL of 80% AcOH, and the mixture was shaken gently at rt for 3 h. Volatiles were evaporated. The residue was dissolved in ~100 µL water and injected into RP HPLC. The major peak of de-tritylated oligonucleotide at ~21 min was collected and concentrated to dryness. The residue was the pure de-tritylated oligonucleotide, which was dissolved in 100 µL water and injected into HPLC to generate the profile of pure de-tritylated oligonucleotide. The pure oligonucleotide was analyzed with MALDI-TOF MS. Using the procedure, oligonucleotides S140n-q were synthesized. The crude trityl-on, pure trityl-on, crude trityl-off and pure trityl-off RP HPLC profiles, pure trityl-on and pure trityl-off MALDI-TOF MS of S140p are provided in FIG. 35-40, respectively. Data for all the oligonucleotides can be found in reference [S Shahsavari et al 2019 *J Org Chem* 84:13374 doi:10.1021/acs.joc.9b01527].

Example 35: Oligonucleotide Synthesis, Deprotection, Cleavage and Analysis—Procedure for the Embodiments Comprising the Use of MeDmoc-MeDim- or Other AlkylDmoc-AlkylDim-Phosphoramidites and Dmoc Linkers Such as S041, S077a-d, 084-087a-d, S108a-e, S111a-e, 117a-e, S121a-e, S122a-e and S123a-e Example oligonucleotides were synthesized on S041 with the support being CPG (26 µmol/g loading, 20 mg, 0.52 µmol) using a MerMade 6 Synthesizer. PnDmoc-PnDim-phosphoramidites S087a-d were used as monomers. Other monomers and supports such as 121-123a-e can also be used with slight modification that is obvious to individuals of ordinary skill in the art. For example, when monomers with relatively bulky groups such as S108a-d are used, longer coupling time is preferred to achieve satisfactory yields. In the current examples, the conditions suggested by synthesizer manufacturer for 1 µmol synthesis were used except that coupling was optionally increased from 2 to 3 times and capping was achieved using S125a, S125b or S125c instead of acetic anhydride. Briefly, detritylation: DCA (3%, DCM), 90 sec×5; coupling: phosphoramidites S087a-d (0.1 M, MeCN), 5-(ethylthio)-1H-tetrazole (0.25 M, MeCN), 60 sec×2 (or 3); capping: S125a-b or S125c (0.1 M, MeCN) and 5-(ethylthio)-1H-tetrazole (0.25 M, MeCN), 60 sec×3; oxidation: I$_2$ (0.02 M, THF/pyridine/H$_2$O, 70/20/10, v/v/v), 40 sec. For incorporating the last nucleoside, S124c instead of S087c was used. At the end of synthesis, the 5'-trityl group was kept on. The procedure for deprotection and cleavage is shown in FIG. 24. The CPG represented by S137 was divided into 5 equal portions. For deprotection and cleavage, one portion was gently shaken in a solution of aqueous NaIO$_4$ (0.4 M, 1 mL) at rt for 3 h. The supernatant was removed with a pipette, and the CPG was rinsed briefly with water (1 mL×4). This converted the CPG represented by S137 to S138. To the CPG was added aqueous K$_2$CO$_3$ (0.05%, pH=8, 1 mL) and the mixture was shaken at rt for 1 h. The supernatant was transferred into a centrifugal tube, which was concentrated to ~100 μL. To the tube was added 1-butanol (900 μL). The tube was vortexed briefly and centrifuged (14.5 k rpm, 5 min). The supernatant was removed with a pipette carefully without sucking the oligonucleotide precipitate. This converted the oligonucleotides S138 to S139. In the cases that the 2'-position of the oligonucleotides has a —F, —OMe or similar groups, the procedure for deprotection and cleavage is the same as described here. In the cases that the 2'-position has a —O-Tom or —O-TBDS group, these groups can be removed either before or after the removal of the sulfur-based protection groups using conditions well-known to skilled individuals. In the cases that the 2'-position has a sulfur-based protecting groups such as —O-Dim or —O-PrDim, these groups will be removed at the same time as other sulfur-based protecting groups, and no additional steps are needed for deprotection and cleavage. In the particular cases in the current examples, the oligonucleotide was dissolved in H$_2$O (100 μL) and ~35 μL was injected into RP HPLC to generate the crude oligonucleotide. Fractions of the major oligonucleotide peak at ~39 min were collected, concentrated to ~100 μL, and injected into HPLC to give the profile of purified trityl-tagged oligonucleotide. To the dried trityl-tagged oligonucleotide was added 1 mL of 80% AcOH, and the mixture was shaken gently at rt for 3 h. Volatiles were evaporated. The residue was dissolved in ~100 μL water and injected into RP HPLC. The major peak of de-tritylated oligonucleotide at ~21 min was collected and concentrated to dryness. The residue was the pure de-tritylated oligonucleotide, which was dissolved in 100 μL water and injected into HPLC to generate the profile of pure de-tritylated oligonucleotide. The pure oligonucleotide was analyzed with MALDI-TOF MS. The crude trityl-on and crude trityl-off RP HPLC profiles, trityl-on and trityl-off MALDI-TOF MS of S140r-t are provided in FIG. 41-52.

The invention claimed is:
1. Derivatized nucleoside phosphoramidites having the general formula (I), wherein at least one of the R$^1$, R$^3$ and R$^8$ groups contain a sulfur-based protecting group as defined below for said groups:

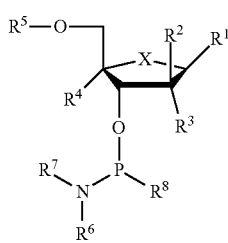

(I)

Wherein, R$^1$, independent from R$^2$-R$^8$, is selected from formulas (II-XI):

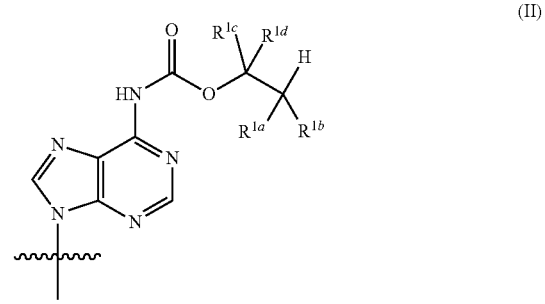

(II)

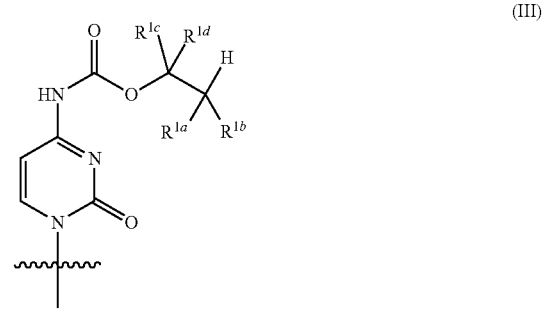

(III)

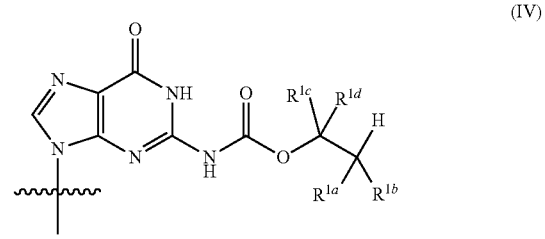

(IV)

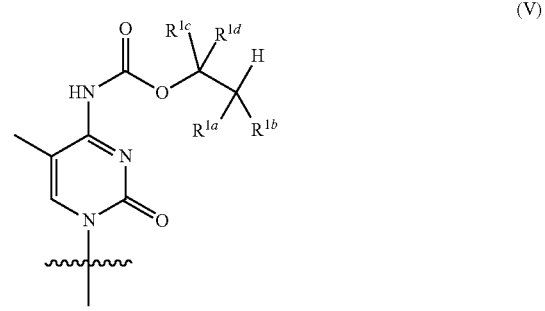

(V)

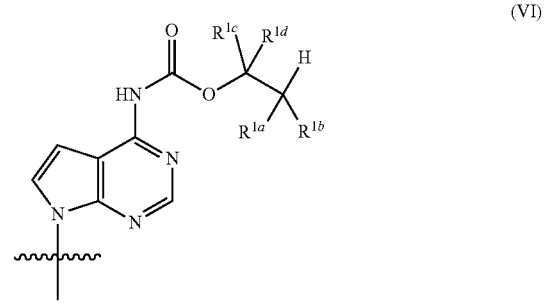

(VI)

-continued

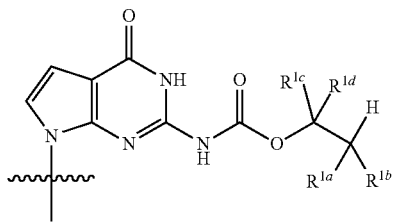
(VII)

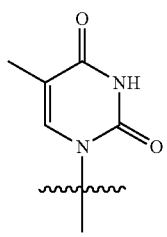
(VIII)

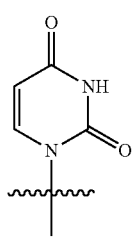
(IX)

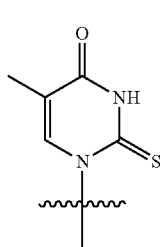
(X)

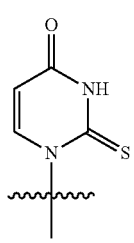
(XI)

Wherein $R^{1a}$ is —$SR^{1a1}$ with $R^{1a1}$ being independently an alkyl group, derivatized alkyl group, aryl group or derivatized aryl group; and $R^{1b}$ is independently H, alkyl group, derivatized alkyl group, aryl group, derivatized aryl group, or —$SR^{1b1}$ with $R^{1b1}$ being independently an alkyl group, derivatized alkyl group, aryl group or derivatized aryl group; or $R^{1a}$-$R^{1b}$=—$S[C(R^{1a2})R^{1a3}]_nS$—, —$S\{[C(R^{1a2})R^{1a3}]_nO[C(R^{1a2})R^{1a3}]_m\}_pS$—, or —$S\{[C(R^{1a2})R^{1a3}]_nS[C(R^{1a2})R^{1a3}]_m\}_pS$— wherein independently $R^{1a2}$ and $R^{1a3}$ are H or alkyl groups, m and n are independently integers larger than 1, and p is a positive integer;

$R^{1c}$ and $R^{1d}$ are independently H, alkyl group, derivatized alkyl group, aryl group, or derivatized aryl group including instances wherein $R^{1c}$ and $R^{1d}$ are connected to form a cycle;

$R^2$=H;

$R^3$ is selected from (XII-XIX)

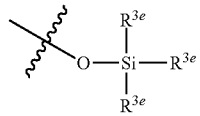
(XII)

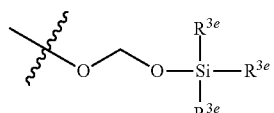
(XIII)

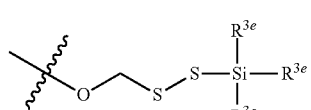
(XIV)

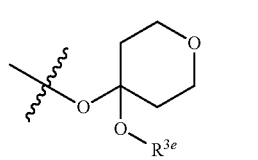
(XV)

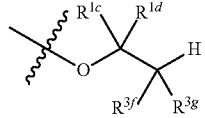
(XVI)

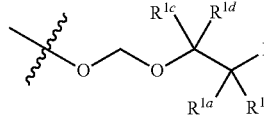
(XVII)

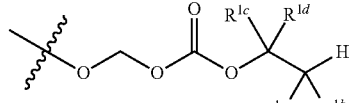
(XVIII)

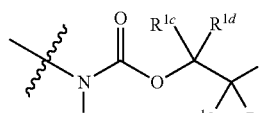
(XIX)

Wherein $R^{1a}$, $R^{1b}$, $R^{1c}$ and $R^{1d}$ are defined as in (I) for $R^1$;

$R^{3e}$ are independently alkyl, derivatized alkyl, aryl or derivatized aryl groups;

$R^{3f}$=$R^{1a}$ and $R^{3g}$=$R^{1b}$ when $R^1$ is (II-VII);

$R^{3f}$ and $R^{3g}$, when $R^1$ is (VIII-XI), are independently —$SR^{3f1}$ with $R^{3f1}$ being an alkyl, derivatized alkyl, aryl or derivatized aryl group; or $R^{3f}$-$R^{3g}$=—$S[C(R^{3f2})R^{3f3}]_nS$—, —$S\{[C(R^{3f2})R^{3f3}]_nO[C(R^{3f2})R^{3f3}]_m\}_pS$—, or —$S\{[C(R^{3f2})R^{3f3}]_nS[C(R^{3f2})R^{3f3}]_m\}_pS$— wherein independently $R^{3f2}$ and $R^{3f3}$ are H or alkyl groups m and n are independently integers larger than 1, and p is a positive integer;

$R^{3h}$ is H, alkyl group, or derivatized alkyl group;

$R^4$=H;

$R^5$ is defined by (XX), (XXI) or (XXII):

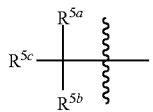
(XX)

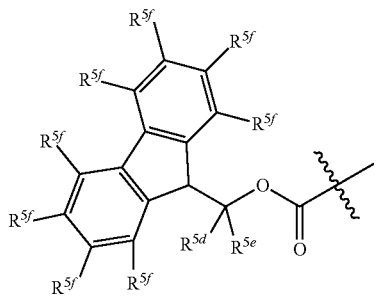
(XXI)

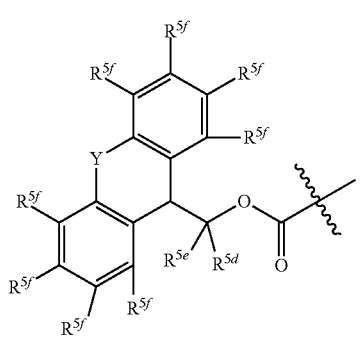
(XXII)

Wherein $R^{5a}$, $R^{5b}$ and $R^{5c}$ are independently H, alkyl groups, derivatized alkyl groups, alkoxyl groups, aryl groups and derivatized aryl groups; $R^{5d}$ and $R^{5e}$ are independently H, alkyl groups and derivatized alkyl groups including groups with the two groups connected to form a cycle; $R^{5f}$ are independently H, halogens, alkyl groups, derivatized alkyl groups, alkoxyl groups, amino groups, substituted amino groups, acylated amino groups, aryl groups and derivatized aryl groups; and Y is a hydrocarbon linkage, —O—, —S—, or —N[($Y^1$)$Y^2$]—, where $Y^1$ and $Y^2$ are independently H, alkyl, and acyl groups;

$R^6$ and $R^7$ are independently alkyl groups or derivatized alkyl groups including those with the two groups linked together to form a nitrogen-containing cycle;

$R^8$ is defined as any of the following groups:

$R^8$=(XXIII) when $R^1$ is any of (II-XI), wherein (XXIII) is:

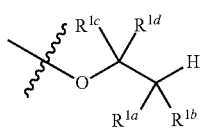
(XXIII)

Wherein $R^{1a}$, $R^{1b}$, $R^{1c}$ and $R^{1d}$ are defined as in (I) for $R^1$;
or $R^8$=alkyl group, derivatized alkyl group or alkoxyl group when $R^1$ is defined by (II-VII), or when $R^1$ is defined by (VIII-XI) and $R^3$ is defined by (XVI-XIX);
or $R^8$=—O[C($R^{8a}$)$R^{8b}$C(H)$R^{8c}$]CN, wherein $R^{8a}$, $R^{8b}$, and $R^{8c}$ are independently H or alkyl groups, when $R^1$ is defined by (II-VII), or when $R^1$ is defined by (VIII-XI) and $R^3$ is defined by (XVI-XIX);

X=—O—, —S—, —CH$_2$— or (XXIV):

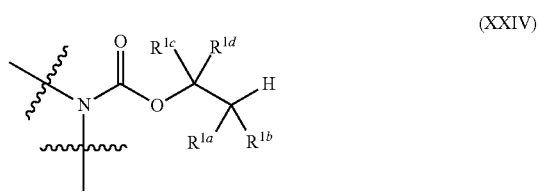
(XXIV)

Wherein $R^{1a}$, $R^{1b}$, $R^{1c}$ and $R^{1d}$ are defined as in (I) for $R^1$.

2. Derivatized nucleoside phosphoramidites of claim 1 wherein $R^{1a}$ is —s$R^{1a1}$, $R^{1b}$ is —SR$^{1b1}$ with $R^{1a1}$ and $R^{1b1}$ being independently alkyl, derivatized alkyl, aryl and derivatized aryl; or $R^{1a}$-$R^{1b}$=—S[C($R^{1a2}$)$R^{1a3}$]$_n$S—, —S{[C($R^{1a2}$)$R^{1a3}$]$_n$O[C($R^{1a2}$)$R^{1a3}$]$_m$}$_p$S—, or —S{[C(($R^{1a2}$)$R^{1a3}$]$_n$S[C($R^{1a2}$)$R^{1a3}$]$_m$}$_p$S— wherein $R^{1a2}$ and $R^{1a3}$ are independently H or alkyl groups, m and n are independently integers lamer than 1, and p is a positive integer.

3. Derivatized nucleoside phosphoramidites of claim 1 wherein $R^1$ is selected from (II-IV); $R^{1a}$-$R^{1b}$=—S[C($R^{1a2}$)$R^{1a3}$]$_n$S—, —S{[C($R^{1a2}$)$R^{1a3}$]$_n$O[C($R^{1a2}$)$R^{1a3}$]$_m$}$_p$S—, or —S{[C(($R^{1a2}$)$R^{1a3}$]$_n$S[C($R^{1a2}$)$R^{1a3}$]$_m$}$_p$S— wherein independently $R^{1a2}$ and $R^{1a3}$ are H or alkyl groups, m and n are independently integers lamer than 1, and p is a positive integer; and $R^{1c}$ is an alkyl group with less than six carbons, and $R^{1d}$=H.

4. Derivatized nucleoside phosphoramidites of claim 1 wherein $R^1$ is selected from (II-IV); $R^{1a}$-$R^{1b}$=—S[C($R^{1a2}$)$R^{1a3}$]$_n$S wherein independently $R^{1a2}$ and $R^{1a3}$ are H or alkyl groups, n is an integers larger than 1; and $R^{1c}$ is an alkyl group with less than six carbons; $R^{1d}$ [[=$R^2$=$R^3$=$R^4$]]=H.

5. Derivatized nucleoside phosphoramidites of claim 1 wherein $R^3$ is defined by (XVI), in which $R^{3f}$ and $R^{3g}$ are independently —SR$^{3f1}$ with $R^{3f1}$ being an alkyl, derivatized alkyl, aryl or derivatized aryl group; or $R^{3f}$-$R^{3g}$=—S[C($R^{3f2}$)$R^{3f3}$]$_n$S—, —S{[C($R^{3f2}$)$R^{3f3}$]$_n$O[C($R^{3f2}$)$R^{3f3}$]m}$_p$S—, or —S{[C($R^{3f2}$)$R^{3f3}$]$_n$S[C($R^{3f2}$)$R^{3f3}$]m}$_p$S— wherein independently $R^{3f2}$ and $R^{3f3}$ are H or alkyl groups, m and n are independently integers larger than 1, and p is a positive integer; and $R^{1c}$ and $R^{1d}$ are defined as in (I) for $R^1$.

6. Derivatized nucleoside phosphoramidites of claim 1 wherein $R^8$ is defined by (XXIII), wherein $R^{1a}$ and $R^{1b}$ are independently —sR$^{1a1}$ with $R^{1a1}$ being an alkyl, derivatized alkyl, aryl or derivatized aryl group; or $R^{1a}$-$R^{1b}$=—S[C($R^{1a2}$)$R^{1a3}$], S—, —S{[C($R^{1a2}$)$R^{1a3}$]$_n$O[C($R^{1a2}$)$R^{1a3}$]$_m$}$_p$S—, or —S{[C(($R^{1a2}$)$R^{1a3}$]$_n$S[C($R^{1a2}$)$R^{1a3}$]$_m$}$_p$S— wherein independently $R^{1a2}$ and $R^{1a3}$ are H or alkyl groups, m and n are independently integers larger than 1, and p is a positive integer.

7. Derivatized nucleoside phosphoramidites of claim 1 wherein $R^3$ is defined by (XVII).

8. Derivatized nucleoside phosphoramidites of claim 1 wherein independently $R^{1a}$-$R^{1b}$=—S(CH$_2$)$_2$S—, —S(CH$_2$)$_3$S—, or —S(CH$_2$)$_4$S—; and $R^{1c}$=$R^{1d}$=H.

9. Derivatized nucleoside phosphoramidites of claim 1 wherein independently $R^{1a}\text{-}R^{1b}$=—S(CH$_2$)$_2$S—, —S(CH$_2$)$_3$S—, or —S(CH$_2$)$_4$S—; $R^{1c}$=H; and $R^{1d}$=Me, Et, Pr, Bu, or Pn.

10. Derivatized nucleoside phosphoramidites of claim 1 wherein independently $R^{1a}\text{-}R^{1b}$=—S(CH$_2$)$_2$S—, —S(CH$_2$)$_3$S—, or —S(CH$_2$)$_4$S—; $R^{1c}$=$R^{1d}$=H; and $R^3$= (XII), (XIII), (XVI) or (XVII).

11. Derivatized nucleoside phosphoramidites of claim 1 wherein independently $R^{1a}\text{-}R^{1b}$=—S(CH$_2$)$_2$S—, —S(CH$_2$)$_3$S— or —S(CH$_2$)$_4$S—; $R^{1c}$=H; and $R^{1d}$=Me, Et, Pr, Bu or Pn; and $R^3$=(XII), (XIII), (XVI) or (XVII).

12. Derivatized nucleoside phosphoramidites of claim 1 wherein formula (I) is (I$_8$-I$_{10}$):

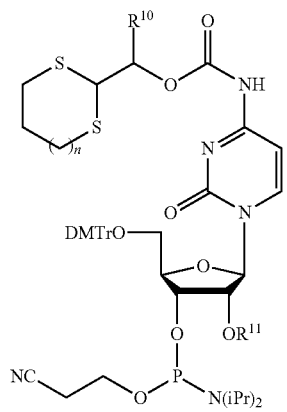
(I$_8$)

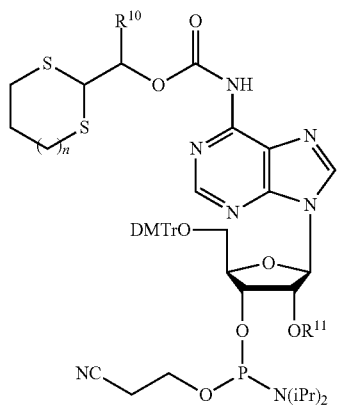
(I$_9$)

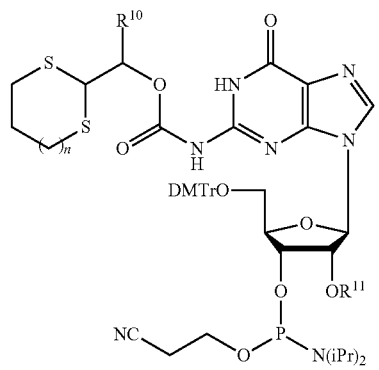
(I$_{10}$)

Wherein $R^{10}$ is H or an alkyl group with less than six carbons, $R^{11}$=[(triisopropylsilyl)oxy]methyl (Tom) or tert-butyldimethylsilyl (TBDS); and n is an integer selected from 0-5.

13. Derivatized nucleoside phosphoramidites of claim 1 wherein formula (I) is (I$_{11}$-I$_{14}$):

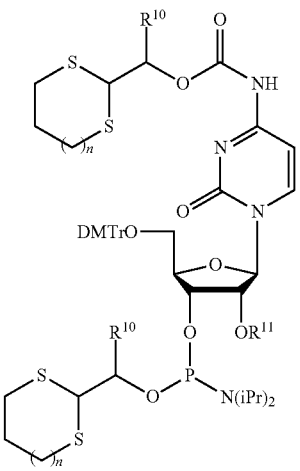
(I$_{11}$)

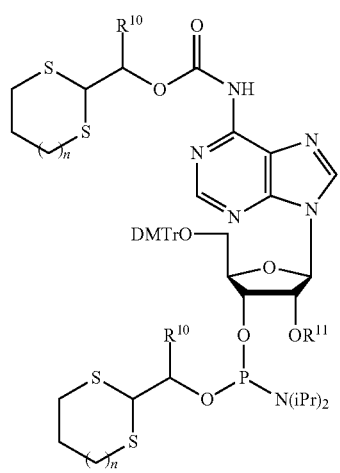
(I$_{12}$)

-continued (I₁₃)

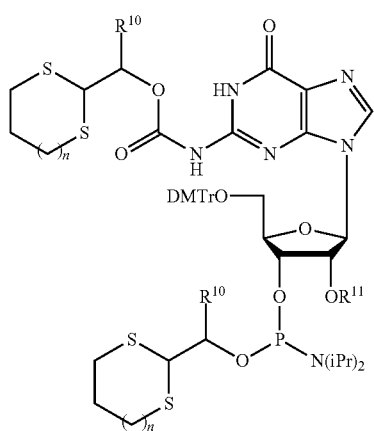

(I₁₄)

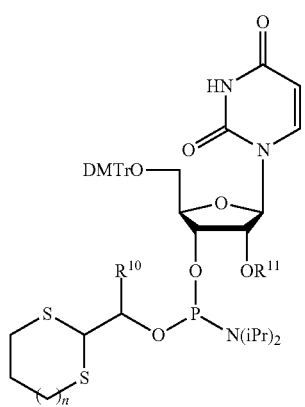

Wherein R¹⁰ are independently H or an alkyl group with less than six carbons; R¹¹=[(triisopropylsilyl)oxy] methyl (Tom) or tert-butyldimethylsilyl (TBDS); and n are independently integers selected from 0-5.

14. Derivatized nucleoside phosphoramidites of claim 1 wherein formula (I) is (I₁₅-I₁₈):

(I₁₅)

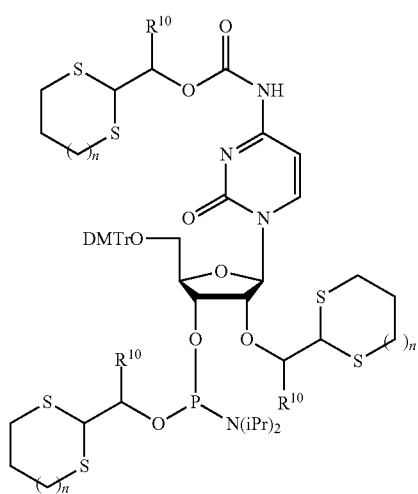

-continued (I₁₆)

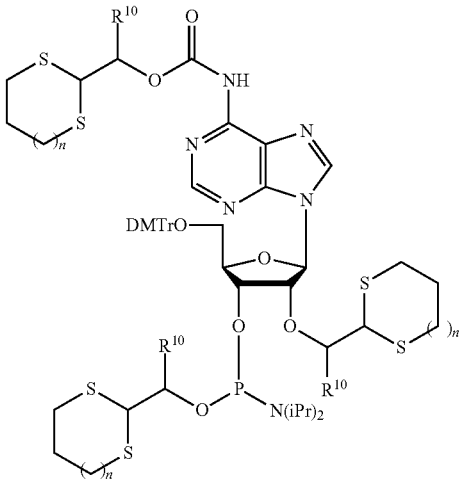

(I₁₇)

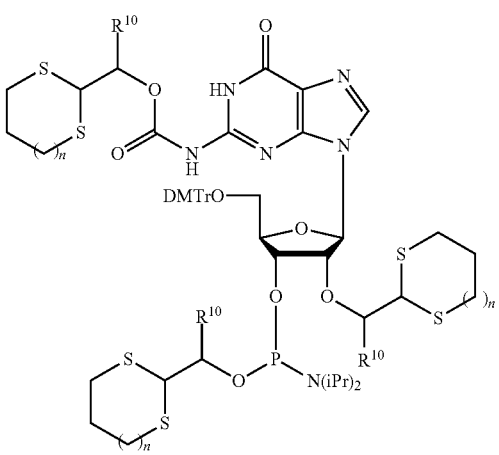

(I₁₈)

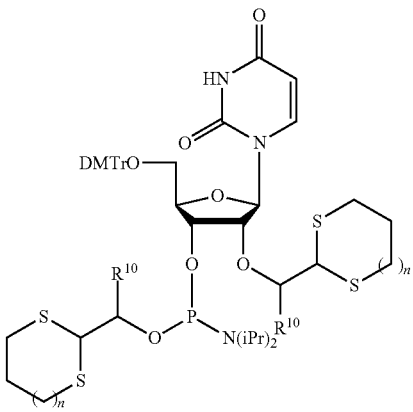

Wherein R¹⁰ are independently H or an alkyl group with less than six carbons;

and n are independently integers selected from 0-5.

15. Derivatized nucleoside phosphoramidites of claim 1 wherein formula (I) is ($I_{19}$-$I_{22}$):
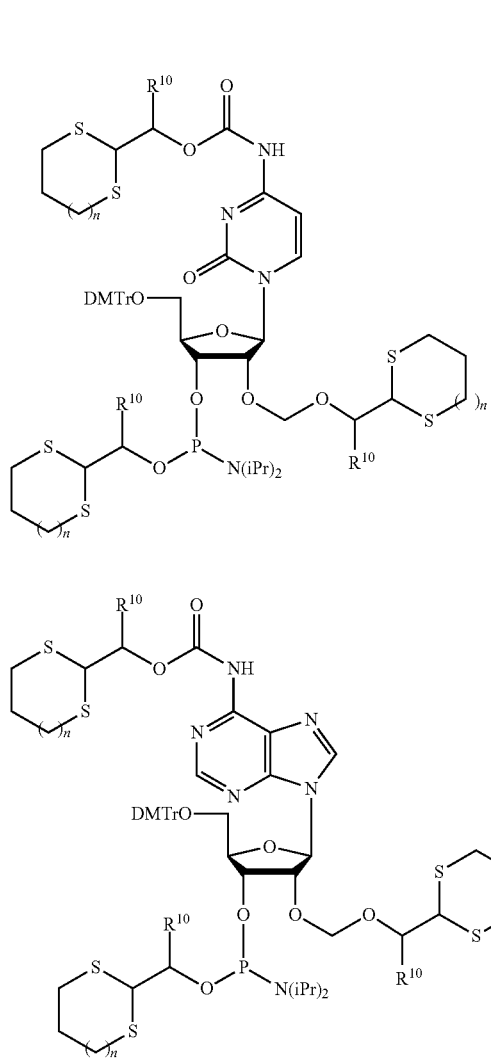
($I_{19}$)
($I_{20}$)
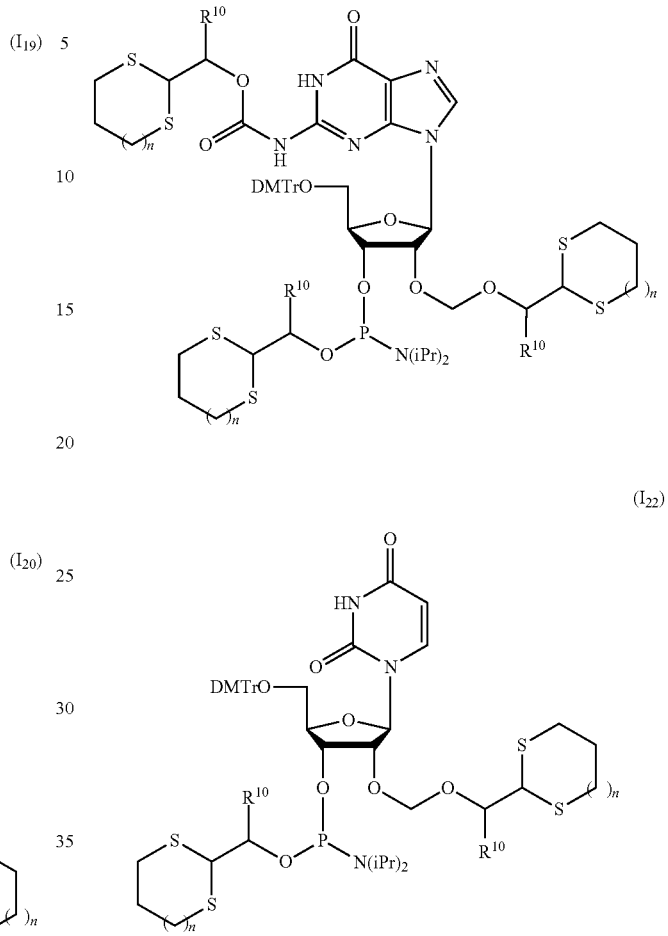
($I_{21}$)
($I_{22}$)
Wherein $R^{10}$ are independently H or an alkyl group with less than six carbons;
and n are independently integers selected from 0-5.
* * * * *